United States Patent

Quinn et al.

(10) Patent No.: US 8,740,856 B2
(45) Date of Patent: Jun. 3, 2014

(54) STOPPERS USED IN PRE-FILLED SYRINGES

(75) Inventors: Michael Vincent Quinn, East Hanover, NJ (US); Eric Schiller, Westfield, NJ (US); Gang Ju, Fair Lawn, NJ (US); E Guan, Doylestown, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 926 days.

(21) Appl. No.: 12/754,101

(22) Filed: Apr. 5, 2010

(65) Prior Publication Data

US 2011/0034882 A1    Feb. 10, 2011

Related U.S. Application Data

(63) Continuation-in-part of application No. 12/133,041, filed on Jun. 4, 2008, and a continuation-in-part of application No. 12/133,076, filed on Jun. 4, 2008.

(60) Provisional application No. 60/941,851, filed on Jun. 4, 2007, provisional application No. 60/950,741, filed on Jul. 19, 2007.

(51) Int. Cl.
*A61M 5/315* (2006.01)

(52) U.S. Cl.
USPC ........... 604/228; 604/218; 604/222; 604/229; 604/230

(58) Field of Classification Search
USPC .......................... 604/218, 222, 230, 228, 229
See application file for complete search history.

(56) References Cited

U.S. PATENT DOCUMENTS

| | | | |
|---|---|---|---|
| 2,895,773 A | 7/1959 | McConnaughey | |
| 3,176,595 A | 4/1965 | Schwartz | |
| 3,809,082 A | 5/1974 | Hurschman | |
| 3,939,833 A * | 2/1976 | Hansson et al. | 604/202 |
| 4,215,701 A | 8/1980 | Raitto | |
| 4,266,557 A | 5/1981 | Merry | |
| 4,354,507 A | 10/1982 | Raitto | |
| 4,363,329 A | 12/1982 | Raitto | |
| 4,500,310 A | 2/1985 | Christinger | |
| 4,543,093 A | 9/1985 | Christinger | |
| 4,931,043 A | 6/1990 | Ray et al. | |
| 4,973,308 A | 11/1990 | Borras et al. | |
| 4,986,820 A | 1/1991 | Fischer | |
| 5,195,975 A | 3/1993 | Castagna | |

(Continued)

FOREIGN PATENT DOCUMENTS

| | | |
|---|---|---|
| DE | 2024117 | 9/1971 |
| EP | 0654280 A1 | 5/1995 |

(Continued)

*Primary Examiner* — Bhisma Mehta
*Assistant Examiner* — Larry R Wilson
(74) *Attorney, Agent, or Firm* — The Webb Law Firm

(57) ABSTRACT

A stopper adapted for attachment with a plunger rod for use within a syringe barrel is disclosed. The stopper includes a main body defining an open rearward end and a closed front end. The open rearward end is adapted to receive a front forward end attachment portion of the plunger rod. The stopper also includes a core member integrally formed with the main body adjacent the closed front end. The core member includes a nose portion having a conical tip configured for entering an outlet opening of the syringe barrel. The closed front end of the stopper has a profile configured to cooperate with an internal surface of the syringe barrel wall to prevent reflux and reduce dead space within the barrel.

23 Claims, 40 Drawing Sheets

(56) References Cited

U.S. PATENT DOCUMENTS

| | | | |
|---|---|---|---|
| 5,201,709 A | 4/1993 | Capra et al. | |
| 5,246,423 A | 9/1993 | Farkas | |
| 5,314,416 A | 5/1994 | Lewis et al. | |
| 5,395,345 A | 3/1995 | Gross | |
| 5,397,313 A | 3/1995 | Gross | |
| 5,411,488 A | 5/1995 | Pagay et al. | |
| 5,411,489 A | 5/1995 | Pagay et al. | |
| 5,496,285 A | 3/1996 | Schumacher et al. | |
| 5,624,405 A | 4/1997 | Futagawa et al. | |
| 5,688,252 A | 11/1997 | Matsuda et al. | |
| 5,713,857 A | 2/1998 | Grimard et al. | |
| 5,722,951 A | 3/1998 | Marano | |
| 5,735,825 A * | 4/1998 | Stevens et al. | 604/218 |
| 5,795,337 A * | 8/1998 | Grimard | 604/222 |
| 5,899,881 A | 5/1999 | Grimard et al. | |
| 6,017,330 A | 1/2000 | Hitchins et al. | |
| 6,053,894 A | 4/2000 | Shadd, Jr. | |
| 6,171,286 B1 | 1/2001 | Gross | |
| 6,361,524 B1 | 3/2002 | Odell et al. | |
| 6,575,938 B2 | 6/2003 | Sayama et al. | |
| 6,743,216 B2 | 6/2004 | Odell et al. | |
| 6,872,191 B2 | 3/2005 | Lo | |
| 6,991,618 B2 | 1/2006 | Lau et al. | |
| 7,056,301 B2 | 6/2006 | Liu | |
| 7,081,107 B2 | 7/2006 | Kito et al. | |
| 7,111,848 B2 | 9/2006 | Tachikawa et al. | |
| 7,534,233 B2 | 5/2009 | Schiller et al. | |
| 2002/0022806 A1 | 2/2002 | Witowski | |
| 2004/0010235 A1 | 1/2004 | Weilbacher et al. | |
| 2004/0127859 A1 | 7/2004 | Ward | |
| 2005/0054979 A1 | 3/2005 | Liu | |
| 2005/0154353 A1 * | 7/2005 | Alheidt | 604/218 |
| 2007/0088270 A1 | 4/2007 | Cude | |

FOREIGN PATENT DOCUMENTS

| | | |
|---|---|---|
| FR | 1500009 | 1/1968 |
| WO | 2005002652 A2 | 1/2005 |
| WO | 2005/061030 A1 | 7/2005 |
| WO | 2005070485 A1 | 8/2005 |

* cited by examiner

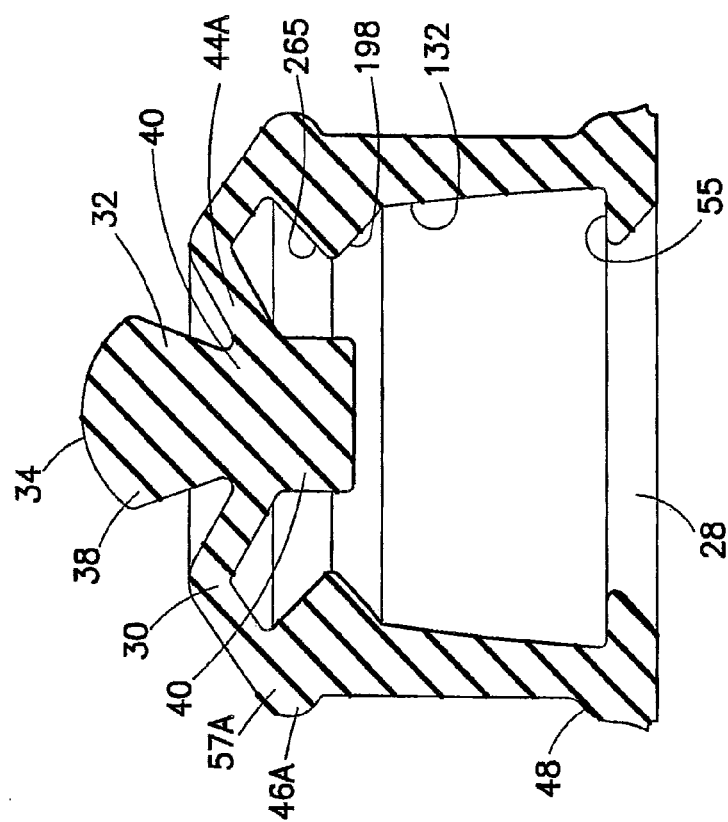
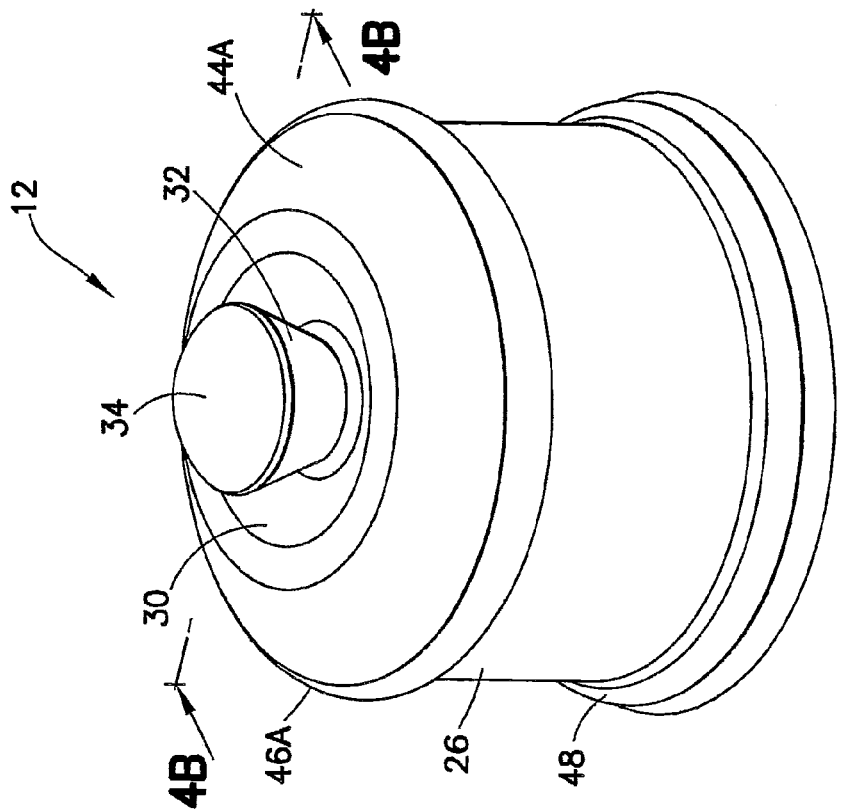
FIG.4B
FIG.4A

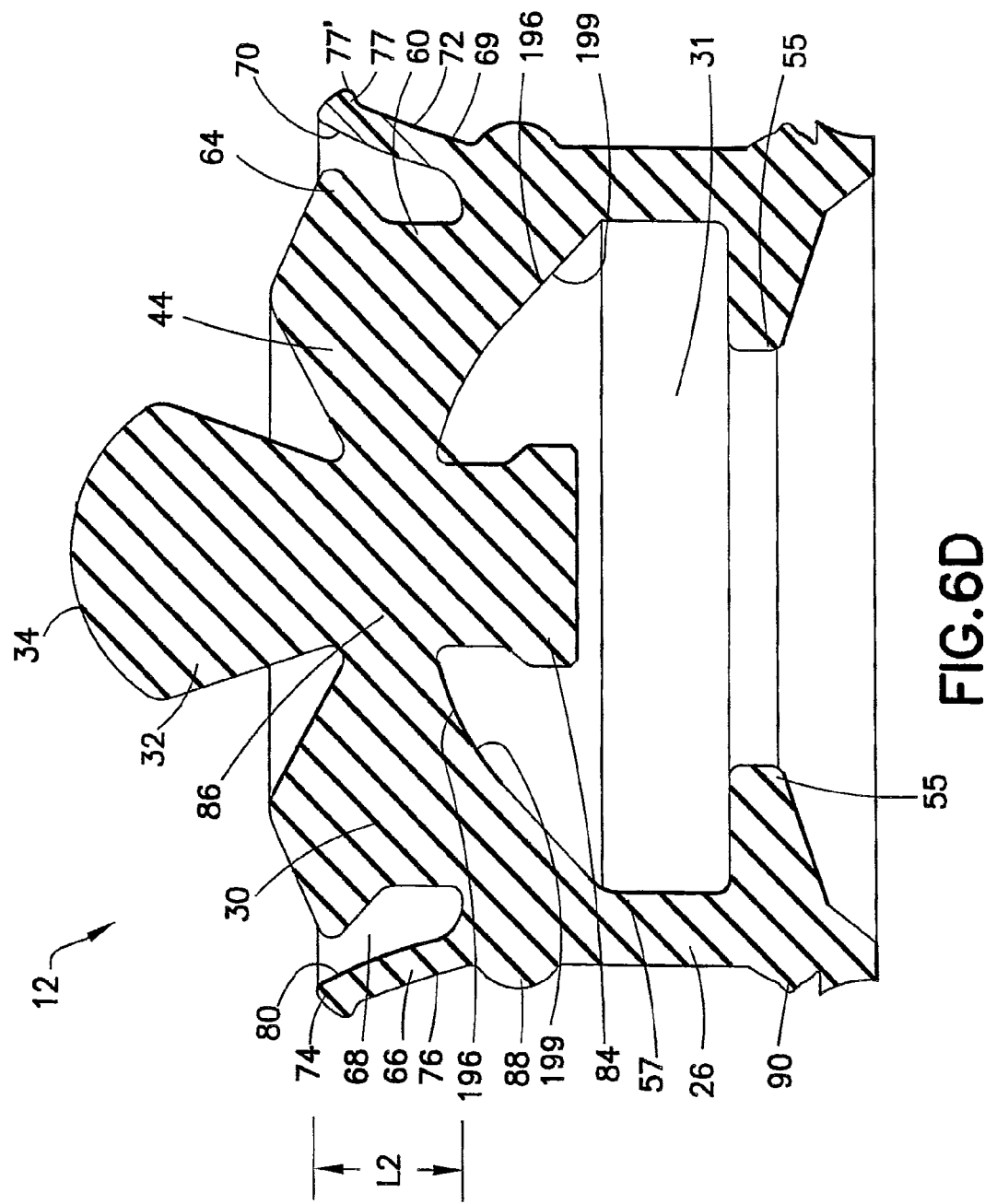

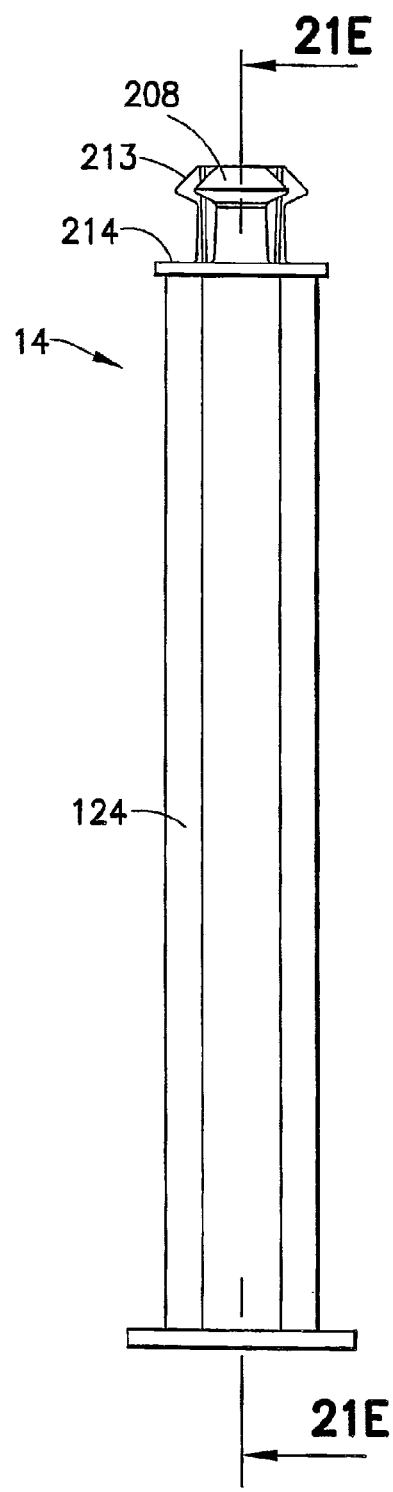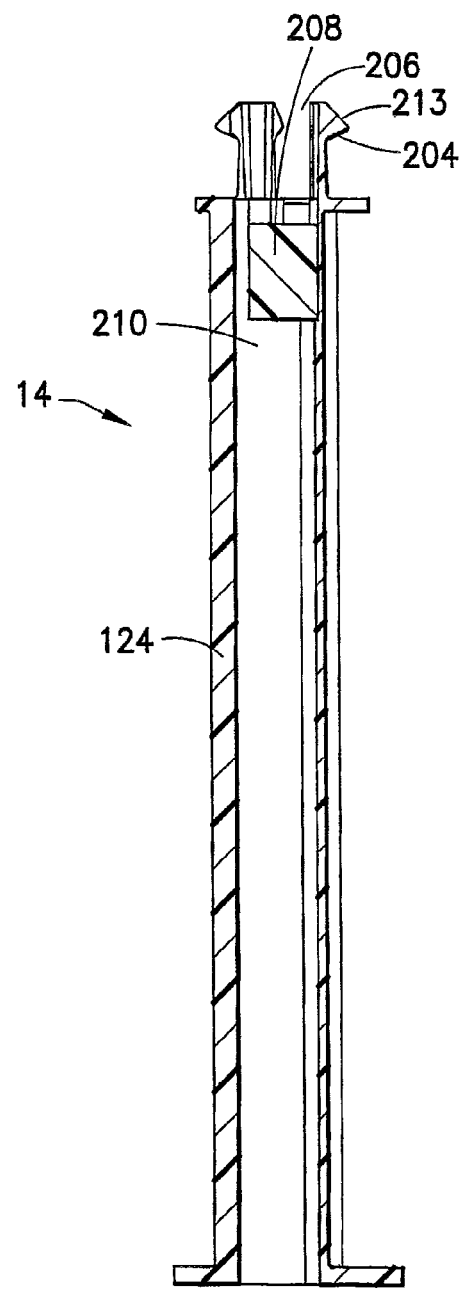
FIG.21C
FIG.21D

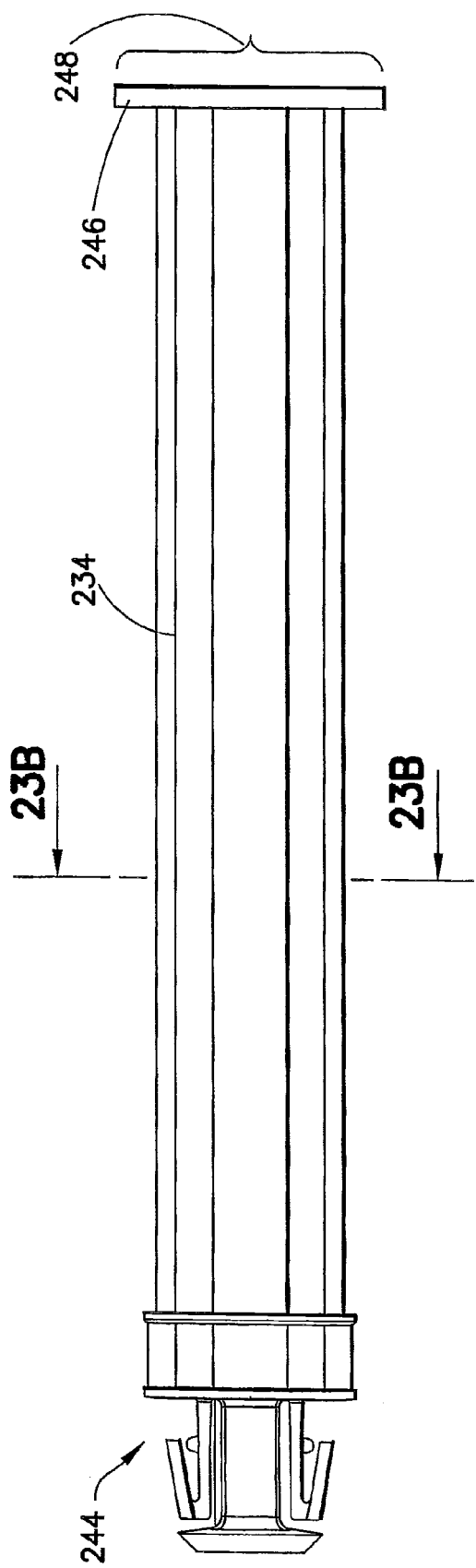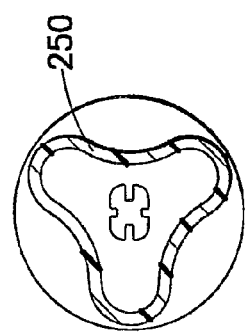
FIG. 23A
FIG. 23B

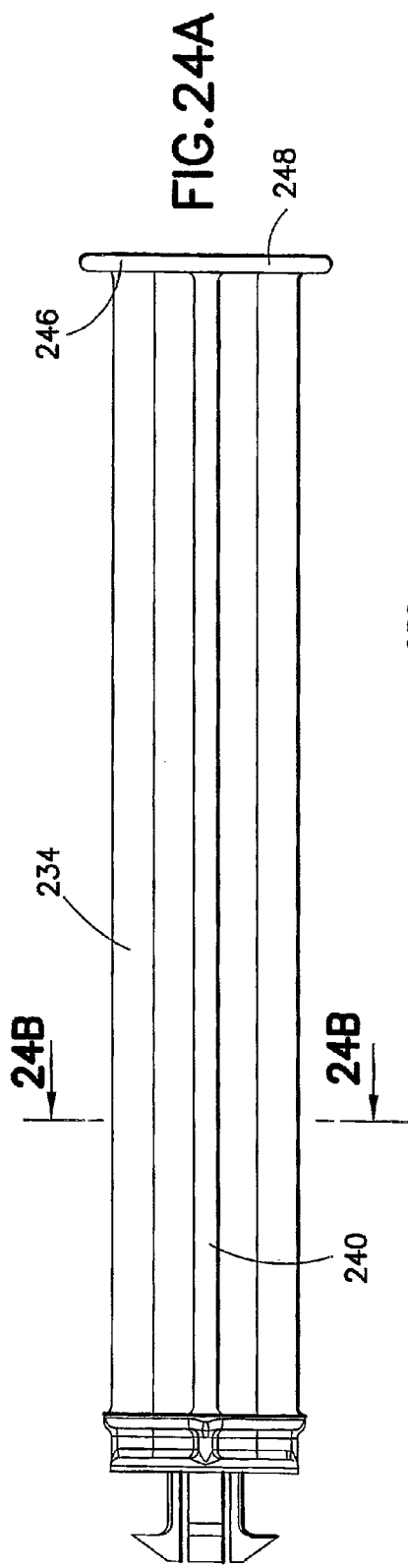
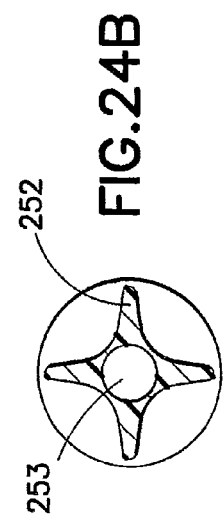
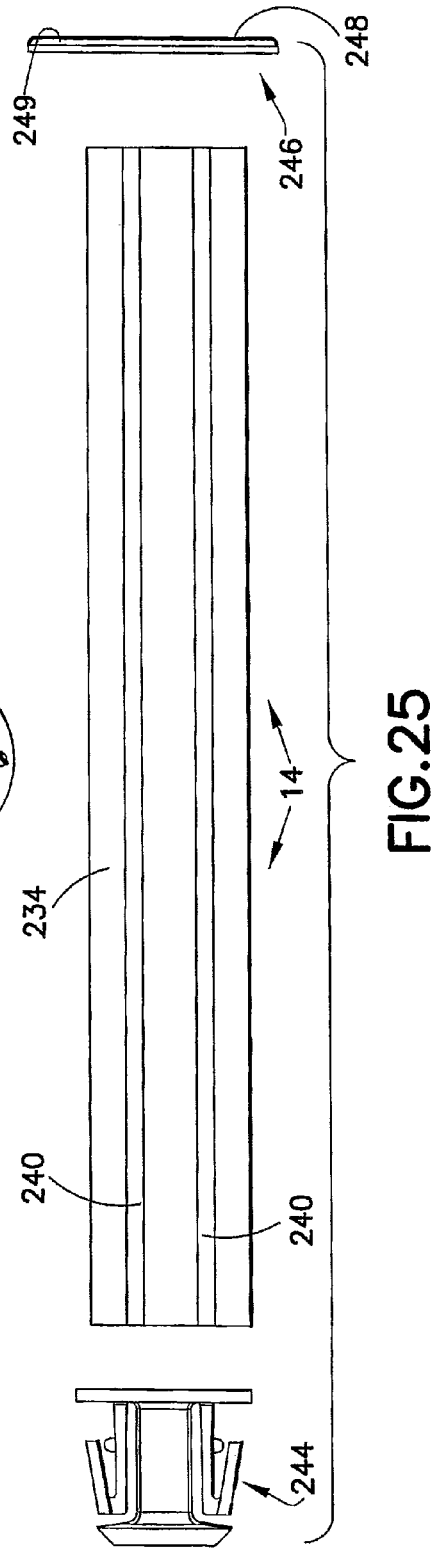

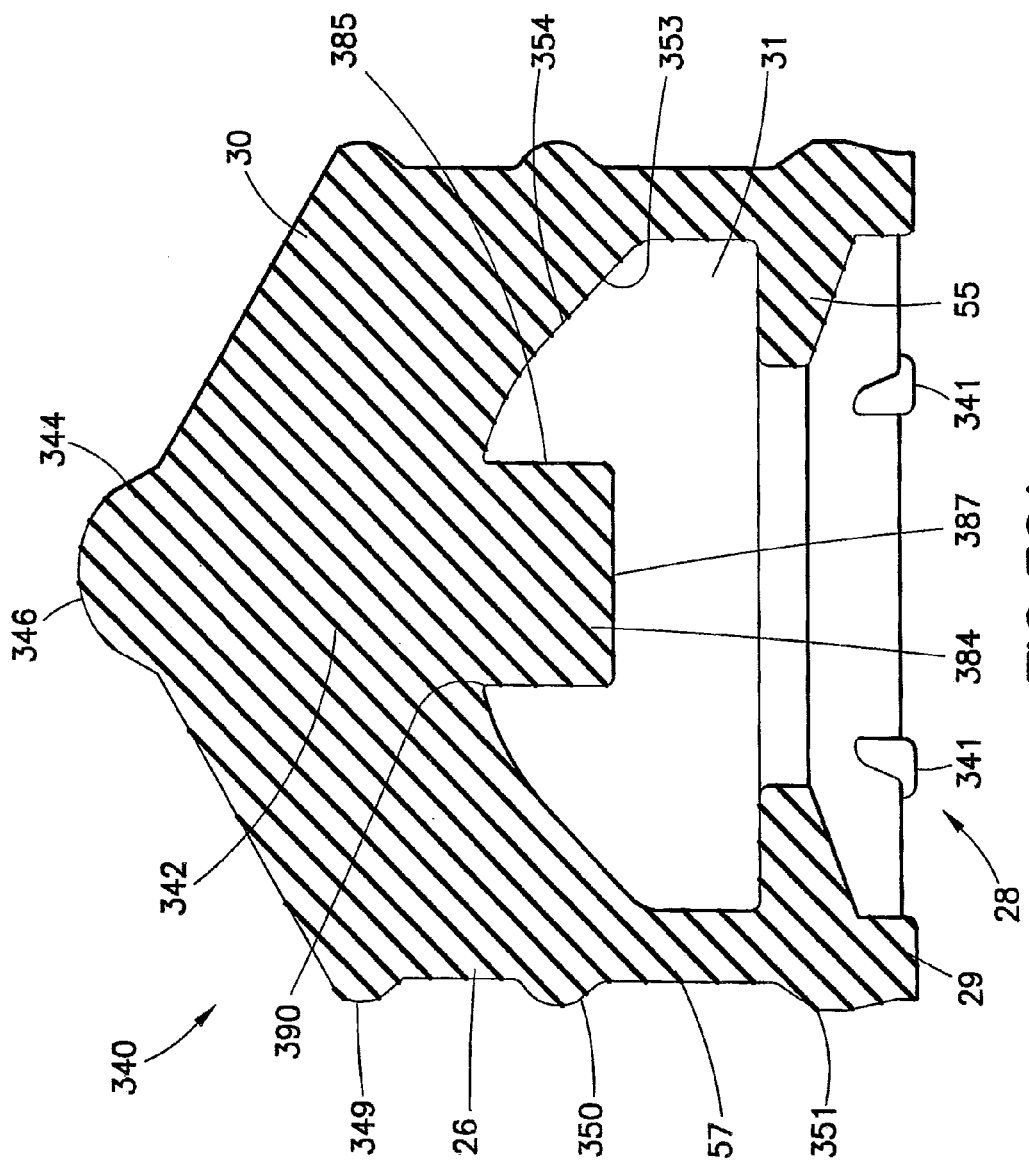

STOPPERS USED IN PRE-FILLED SYRINGES

CROSS REFERENCE TO RELATED APPLICATIONS

This application is a continuation-in-part of U.S. patent application Ser. Nos. 12/133,041 and 12/133,076, both filed Jun. 4, 2008, which claim priority to U.S. Provisional Patent Application No. 60/941,851, filed Jun. 4, 2007, entitled "Stopper and Plunger Rod for a Pre-Filled Syringe", and to U.S. Provisional Patent Application No. 60/950,741, filed Jul. 19, 2007, entitled "Positive Displacement Stopper for a Pre-Filled Syringe", the entire disclosures of all of which are hereby incorporated by reference in their entirety.

BACKGROUND OF THE INVENTION

1. Field of the Invention

The invention relates in general to a stopper assembly for use with a syringe and, more particularly, to a stopper assembly having low dead space and essentially zero reflux for use with a pre-filled syringe such as those used in flush applications. The invention also relates to a plunger rod and an attachment member adapted for attachment with a stopper assembly.

2. Description of Related Art

Pre-filled syringes, such as those used in flush applications, are typically filled with a saline solution and are used to flush catheters. Examples of pre-filled syringes are shown in U.S. Pat. Nos. 6,361,524 and 6,743,216, which are incorporated herein by reference and which are directed to syringe assemblies for flush applications. During use, the nurse or technician "bottoms out" the stopper in the syringe barrel at the end of the flushing procedure. The process of bottoming out the stopper in the barrel can cause a phenomenon known as reflux. Reflux is the reversal of fluid flow up through the catheter, usually due to the spring back of the stopper at the end of a flush injection. Reflux may occur when the stopper compresses to force out additional saline and subsequently springs back to shape, causing saline to be pulled back into the syringe. Reflux can also pull blood back into the catheter, clogging it. This phenomenon of reflux may be detrimental to the maintenance of the catheter line. Accordingly, it is desirable to reduce or eliminate reflux within the syringe.

Existing stopper designs typically include a constant diameter seal and a constant stopper-to-barrel interference to create a seal that will prevent fluid housed inside the barrel from leaking past the front seal of the stopper. The contact pressure of the seal is determined by the interference in these designs, and has to be sufficiently high such that the seal will not leak under the highest possible fluid pressure inside the barrel. The disadvantage of this traditional design is that higher contact pressures lead to higher static and dynamic frictional forces. Static friction is commonly referred to as "break loose" force. Additionally, existing stoppers typically include tip designs that are not self-centering. Because the tips are not self-centering, they do not form a positive seal with the inside back of the luer taper when subjected to axial forces.

Existing stopper designs have attempted to prevent the flow of fluid from the catheter back into the syringe by preventing spring back of the stopper which would create a vacuum to draw fluid back into the syringe. These designs, while effective in reducing reflux, do not consistently prevent all reflux from occurring. Further still, many of these designs include a significant amount of dead space volume. The ISO standard for dead space requirement for a 3 ml syringe is 70 μl, for a 5 ml syringe is 75 μl, and for a 10 ml syringe is 100 μl.

SUMMARY OF THE INVENTION

There is a need in the art for a stopper design that creates an active seal within a syringe barrel wherein the chance for slippage of the plunger rod past the stopper taper and lodging against a front wall of the stopper is reduced. There is also a need in the art for a stopper design which is relatively short while still achieving an active seal. There is a further need in the art for a stopper design that is easily molded. There is also a need in the art for a stopper design that achieves a "positively zero" or an essentially zero reflux which meets the ISO standard for dead space. The concept of an active seal involves an increase in pressure inside the syringe barrel which will cause the forward seal of the stopper to have a higher contact pressure with the inside walls of the barrel, maintaining a higher contact pressure than the internal fluid pressure, thereby preventing leakage at the stopper seal. There is yet another need in the art for a stopper design that includes a feature that allows for the capture and storage of potential energy prior to the release of the force from the plunger rod, effectively and consistently reducing and/or eliminating reflux of fluid back into the syringe upon this release of pressure on the plunger rod. There is also a need in the art for a plunger rod attachment design that can be easily inserted into the stopper of a pre-filled, sterilized syringe with the application of minimal force thereto and which is securely held within the stopper during use of the syringe. There is a further need in the art for a plunger rod design that uses a reduced amount of processing material, has a reduced molding cycle time, and has a high resistance to side loading.

The particularly disclosed stopper designs create a positive displacement of fluid out of the syringe (and therefore into any attached catheter, for example) after the stopper has been bottomed in the syringe barrel and force is released from the plunger rod so as to effectively and consistently reduce and/or eliminate reflux of fluid back into the syringe upon the release of pressure on the plunger rod. The stopper design also eliminates the possibility of "push through" of the plunger rod within the stopper, shortens the height of the stopper, and improves the moldability. One stopper design also meets the ISO standard for dead space while also achieving a "positively zero" (meaning close to zero) reflux. The stopper is adapted for attachment with a plunger rod for use within a syringe barrel.

According to one aspect, the invention is directed to a stopper adapted for attachment with a plunger rod for use within a syringe barrel. The stopper comprises a main body defining an open rearward end and a closed front end. The open rearward end is adapted to receive a front forward end attachment portion of a plunger rod. The stopper also includes a core member integrally formed with the main body adjacent the closed front end. The core member includes a nose portion having a profile adapted to create a positive seal with an outlet opening of the syringe barrel. The stopper includes at least one rib extending radially outward around a perimeter of the main body for forming an active seal with the syringe barrel. An inward shoulder portion is provided on an inner surface of the main body. This inward shoulder portion is adapted for contact with a taper on the forward end of the plunger rod, wherein contact of the inward shoulder portion with the taper causes the stopper to apply a radial force to the at least one rib and the syringe barrel upon the application of a forward force to the plunger rod and wherein the inward shoulder portion includes a first cylindrical wall portion extending from the closed front end of the main body. This first wall portion has a substantially flat surface profile. The inward shoulder portion further includes a second cylindrical wall portion extending toward the open rearward end of the main body. A sloped portion extends between the first wall and the second wall. The provision of a first wall having a substantially flat surface profile results in a shorter stopper having an active seal angle which is relatively shallow. The core member includes a front portion, a back portion, and a central portion positioned between the front and back portion wherein the front portion extends beyond the front end of the main body and the central portion is interconnected with the main body via a flexible membrane extending between the core member and the main body. The main body includes at least one forward extending skirt extending from a front end of the main body which is adapted for creating a positive pressure chamber therein. According to one embodiment, the core member can include a back portion and at least one of the back portions of the core and an inner surface of the closed front wall including at least one concentric groove formed therein. The at least one of the back portions of the core member and the inner surface of the closed front wall include stopper material adapted for contacting the front forward end attachment portion of the plunger rod upon an application of forward force to the plunger rod. This stopper material prevents the stopper from slipping forward and reduces the amount of pressure on the center of the stopper member.

According to another aspect, the invention is directed to a plunger rod and stopper assembly adapted for use with a syringe barrel. The assembly comprises a plunger rod having a front attachment end and a back end and extending along a longitudinal axis. The front attachment end includes a taper and a front flange extending therefrom. The assembly also includes a stopper having a main body defining an open rearward end, a closed front end, and a core member integrally formed with the main body adjacent the closed front end. The open rearward end is defined by an inside wall surface and is adapted for receiving the front attachment end of the plunger rod and locking the plunger rod within the stopper. At least one rib is provided on the stopper that extends radially outward around a perimeter of the main body for forming an active seal with the syringe barrel. A taper having a sloped surface is formed on an inner surface of the main body. This taper is adapted for contact with the taper on the forward end of the plunger rod. The contacting tapers form an active seal surface for cooperating together such that the stopper applies a radial force to the at least one rib and syringe barrel upon the application of a forward force to the plunger rod. An open space is defined in the stopper by the inner surface of the main body, a portion of the core member, and the taper on the inner surface of the main body. The front flange extending from the front attachment end of the plunger rod extends into this open space to limit the travel of the plunger rod relative to the stopper.

According to yet another aspect, the invention is directed to a stopper adapted for attachment with a plunger rod for use within a syringe barrel. The stopper comprises a main body defining an open rearward end and a closed front end. The open rearward end is adapted to receive a front forward end attachment portion of the plunger rod. The main body includes an inner surface. A core member is integrally formed with the main body adjacent the closed end. The core member includes a nose portion having a conical tip configured for entering an outlet opening of the syringe barrel. At least a first rib extends radially outward around a perimeter of the main body. At least a second rib extends radially outward around a perimeter of the main body. The second rib is adapted for forming an active seal with the syringe barrel. A taper is provided on the inner surface of the main body. The taper is adapted for contact with a corresponding taper on the front forward end attachment portion of the plunger rod. The contacting tapers cooperate together to cause the stopper to apply a radial force to the syringe barrel upon the application of a forward force to the plunger rod, wherein the main body includes a sidewall having a first diameter for containment within a syringe barrel having a first internal diameter wall portion; the conical tip has a second diameter for contacting the barrel outlet having a second internal diameter wall portion; and the closed front portion has a profile configured for cooperating with a tapered portion wall portion of an internal barrel wall extending between the first and second barrel internal diameter wall portions resulting in a reduction of dead space within the barrel. The main body can include at least a third rib and the first, second, or third rib extends radially outward around a perimeter of the main body and is axially spaced apart along this main body. The main body includes at least one undercut portion extending axially inward of the open rearward end. The undercut portion is adapted for locking the forward end of the plunger rod within the stopper. The taper of the inner surface of the main body can be a continuous contour from a side wall portion of the main body to the core member. The closed front portion has a first slope extending from the nose portion to the first rib which is slightly steeper than a second slope of the tapered wall portion of the syringe barrel extending from the outlet opening of the barrel to a top sidewall portion of the syringe barrel. Upon the application of a forward force to the stopper, the cooperation between the first and second slopes and radial pressure of the internal barrel wall with respect to the at least first rib causes longitudinal extension of the stopper such that the stopper nose extends into the barrel outlet to prevent reflux. According to one embodiment, an angle of the first slope can be approximately 1° less than the angle of the second slope and the longitudinal expansion of the stopper upon application of a forward force to the plunger rod results in an angle increase of approximately 2.8° of the first slope. According to a further embodiment, the open rearward end of the stopper can be defined by a perimetrical edge portion and an outer surface of this edge portion can include at least one protrusion, but preferably six protrusions, extending therefrom. According to yet a further embodiment, the core member includes a back core portion defined by a sidewall portion extending from a bottom core surface to an intersection point between the back core portion and a taper surface of the stopper, wherein this sidewall portion is essentially straight substantially along its entire length. This particular design results in a reduction in tooling costs for the stopper.

According to yet another aspect, the invention is directed to a syringe having low dead space and essentially zero reflux. The syringe comprises a cylindrical barrel including a proximal end, a distal end, and a sidewall having a first internal diameter extending between the proximal and distal end. The distal end terminates in an outlet opening having a second internal diameter which is less than the first internal diameter. The cylindrical barrel includes a second sloped or tapered surface extending between the outlet opening and the barrel sidewall. A plunger rod is extendable into the barrel through an opening in the proximal end of the barrel. This plunger rod includes a front forward attachment portion. The syringe further includes a stopper having a main body having an open rearward end, a closed front end, and a sidewall portion extending between the open rearward end and the closed front end. The open rearward end is adapted to receive the front forward end attachment portion of the plunger rod and a core member is integrally formed with the main body adjacent the closed end. The core member includes a nose portion having a conical tip configured for entering the outlet opening of the syringe barrel. The closed front end includes a first sloped surface extending from the conical tip to the stopper sidewall portion. The first sloped surface of the stopper is slightly steeper than the second sloped surface of the cylindrical barrel such that an application of a forward force to the plunger rod causes the conical tip of the stopper to enter into the outlet opening resulting in a "positively zero" reflux while the first and second slopes cooperate together to reduce dead space within the barrel. The main body can include a first rib extending radially outward around a perimeter of the main body and at least a second rib also extending radially outward around a perimeter of the main body spaced a distance away from the first rib. The at least second rib is adapted for forming an active seal with the syringe barrel. The main body of the stopper includes an inner surface having a taper adapted for contact with a corresponding taper on the forward end of the plunger rod. These contacting tapers cooperate together so that the stopper applies a radial force to the syringe barrel upon the application of a forward force to the plunger rod. The taper of the inner surface of the main body can be a continuous contour from a side wall portion of the main body to the core member. The main body can include at least one undercut portion extending axially inward from the open rearward end. This undercut portion is adapted for locking the front portion of the plunger rod within the stopper.

BRIEF DESCRIPTION OF THE DRAWINGS

FIG. 4A is a perspective view of a stopper according to a second embodiment of the invention in accordance with an embodiment of the present invention.

FIG. 4B is a cross-sectional side view of the stopper of FIG. 4A taken along line 4B-4B.

FIG. 6D is a cross-sectional side view of a stopper having an exterior design of FIG. 6A taken along line 6B-6B of FIG. 6A and having an interior design as shown in FIG. 6C in combination with an alternative type of attachment portion of a syringe plunger rod.

FIG. 21C is a side view of the plunger rod of FIG. 21B.

FIG. 21D is a side view of the plunger rod of FIG. 21A wherein the reinforcing slug is positioned within a hollow portion of the plunger rod.

FIG. 23A is a side view of the plunger rod according to a second embodiment of the invention.

FIG. 23B is a cross-sectional view of the plunger rod of FIG. 23A taken along line 23B-23B.

FIG. 24A is a side view of the plunger rod according to a third embodiment of the invention.

FIG. 24B is a cross-sectional view of the plunger rod of FIG. 24A taken along line 24B-24B.

FIG. 25 is an exploded side view of the individual components of the plunger rod, which may be separately formed, in accordance with an embodiment of the present invention.

FIG. 30A is a cross-sectional side view of a stopper according to an eighth embodiment of the invention.

DETAILED DESCRIPTION OF THE INVENTION

Figure 1:
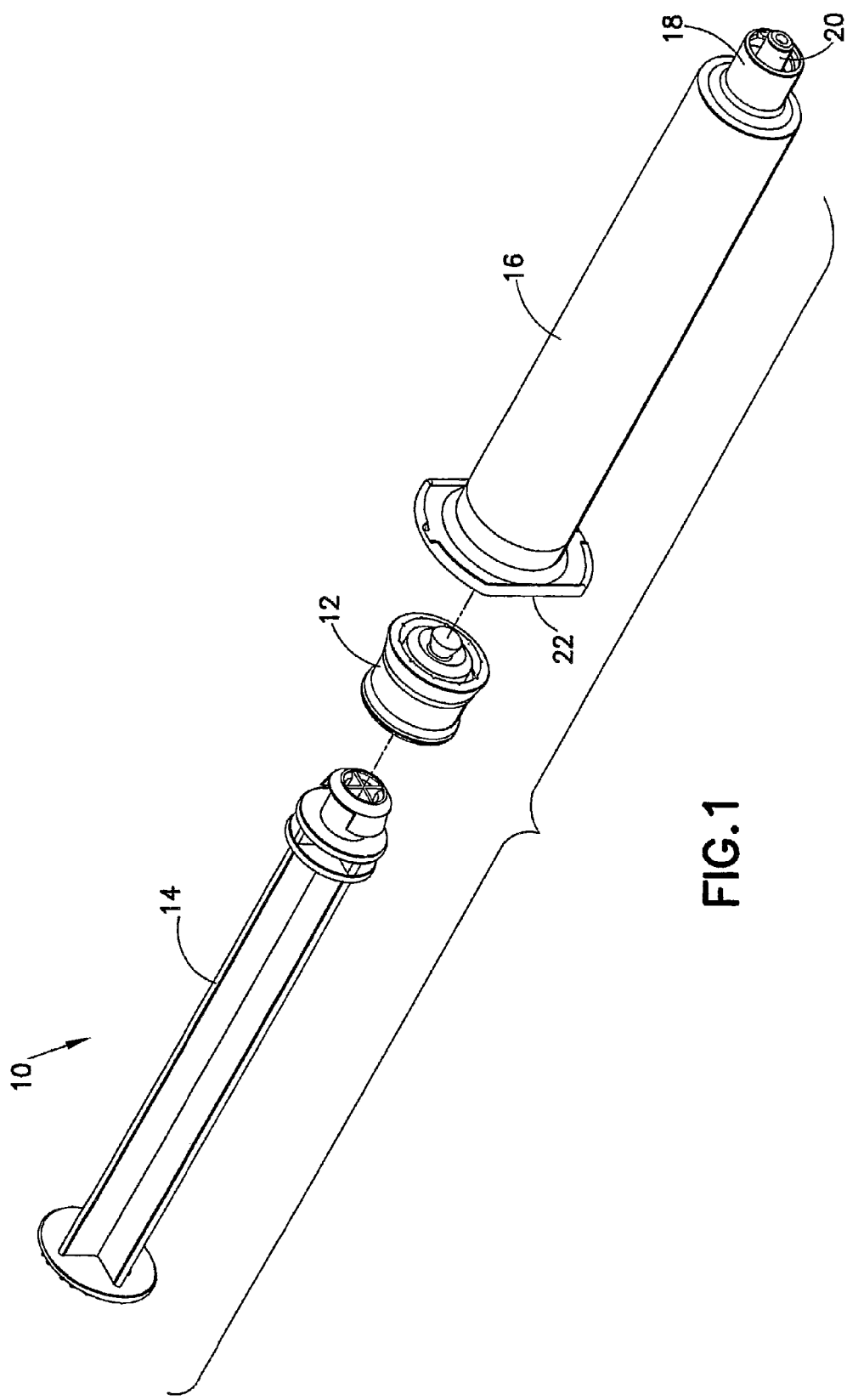
FIG. 1 is an exploded perspective view of a plunger rod, stopper, and syringe barrel in accordance with an embodiment of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Reference is now made to FIG. 1, which shows a perspective view of a syringe, generally indicated as 10. The syringe comprises a stopper 12 and a plunger rod 14. The stopper 12 and plunger rod 14 are adapted for use within a syringe barrel 16. The syringe 10 is preferably of a type that is pre-filled and sterilized for use in flush applications. The syringe barrel 16 includes a distal or frontal end 18 which includes an outlet opening and/or a mechanism for attachment of a separate medical device (such as a catheter), shown in the form of a luer 20, and an open proximal or rearward end 22 for receiving the stopper 12 and plunger rod 14 assembly. While the figures herein depict a separate stopper and plunger assembly, it is contemplated that the stopper features may be integrally formed with a plunger rod 14.

Figure 2B:
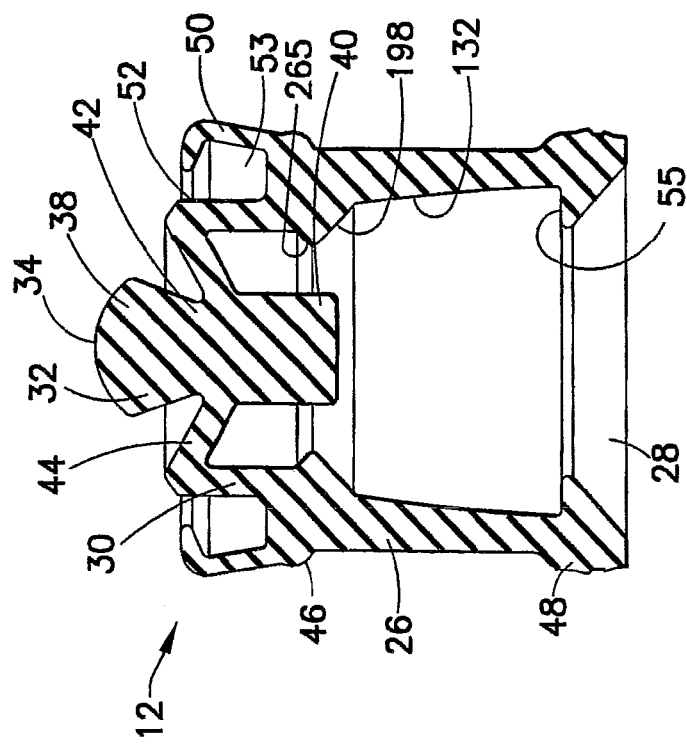
FIG. 2B is a cross-sectional side view of the stopper of FIG. 2A taken along line 2B-2B.
Figure 2A:
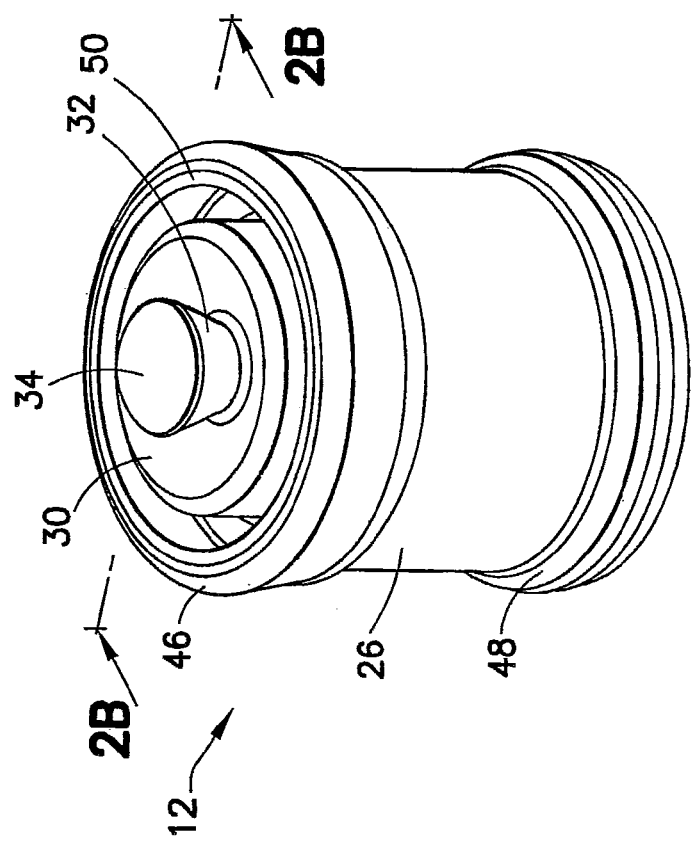
FIG. 2A is a perspective view of a stopper according to a first embodiment of the present invention.
Figure 6A:
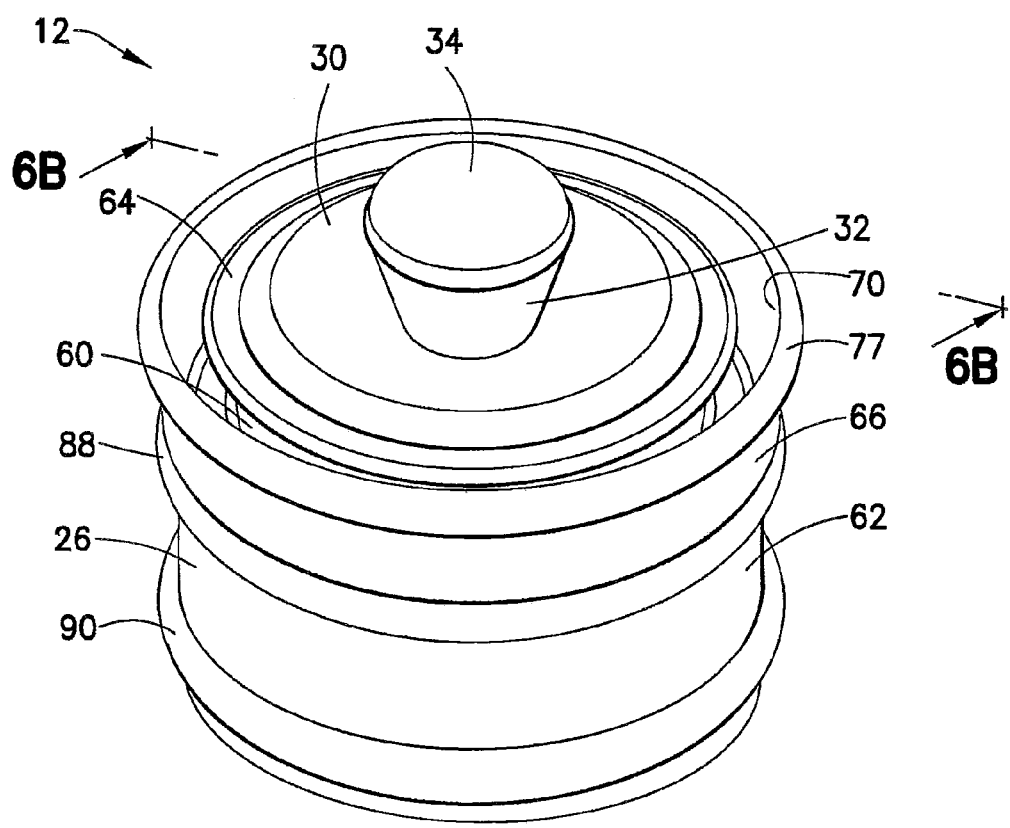
FIG. 6A is a perspective view of a stopper according to a fourth embodiment of the invention in accordance with an embodiment of the present invention.

Reference is now made to FIGS. 2A, 4A, and 6A which show perspective views of the positive displacement stopper 12 according to several different embodiments of the invention. FIGS. 2B, 4B, and 6B-6D show cross-sectional views of the different stopper embodiments in which the details of the positive displacement features of the stopper with respect to the syringe 10 can be readily viewed, wherein like elements are denoted by consistent numbering between the figures. The stopper 12 is adapted for attachment with a plunger rod 14 for use within a syringe barrel 16. The stopper 12 is preferably made of an elastomeric material selected from the group of natural rubber, synthetic rubber, thermoplastic elastomers, or combinations thereof. The stopper 12 of the invention is particularly useful with flush syringes such as those for use in connection with a catheter, as is well known in the art.

The stopper includes a main body 26 defining an open rearward end 28 and a closed front end 30. The open rearward end 28 is adapted to receive the front forward end attachment portion 31 of the plunger rod 14. The front forward end attachment portion 31 can be of any known design which is capable of attachment to the stopper 12; however, the present invention includes several inventive attachment members which are adapted for use with the stopper 12 of the present invention. These inventive attachment members are discussed in further detail below.

Figure 3:
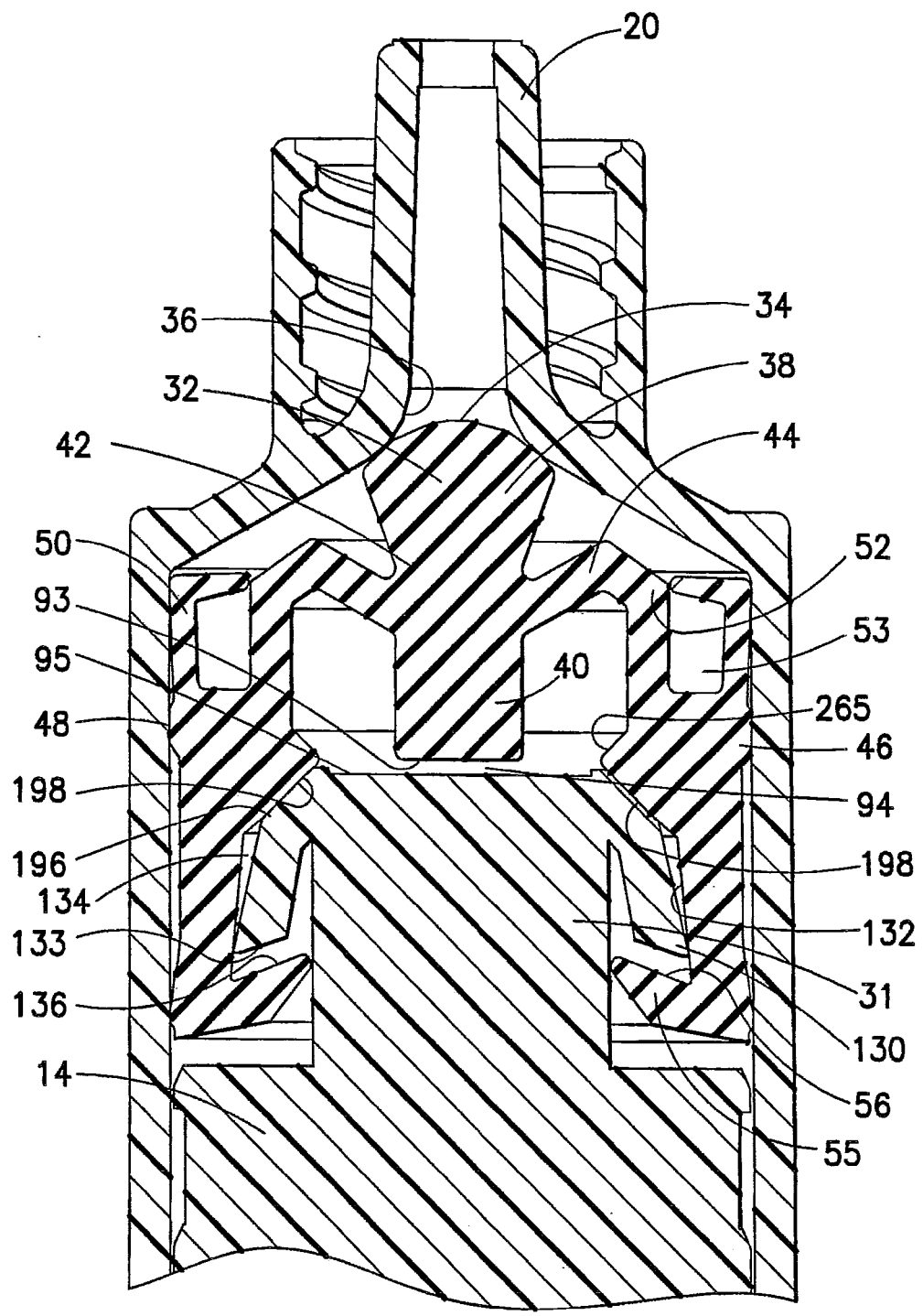
FIG. 3 is a cross-sectional side view of the stopper of FIG. 2A attached to a plunger rod and positioned within a syringe barrel.

The stopper 12 further includes a flexible core member 32 integrally formed with the main body 26 adjacent the closed front end 30. As shown in FIG. 3, the flexible core member 32 includes a nose portion 34 having a profile adapted to be self-centering such that even when the stopper 12 is not centered in the syringe barrel 16, it creates a positive seal with an outlet opening of the syringe barrel 16, such as an interior surface 36 of a luer 20 of the syringe barrel 16. As used herein, the term "positive seal" means that the nose portion 34 of stopper 12 is seated to fully contact against and seal against the interior surface 36 of luer 20. Once the stopper 12 has traveled the full distance through the syringe barrel 16 and contacts the internal surface at the forward wall or interior surface 36 of the luer 20, a positive seal may be formed therewith. In one embodiment, the nose portion 34 has a semi-spherical shape, which is self-centering such that even when the stopper 12 is not centered in the syringe barrel 16, it creates a positive seal with the outlet opening or luer 20 once the stopper 12 is bottomed in the syringe barrel 16. The nose portion 34 of the flexible core member 32 may include other shapes such as substantially conical, cubic, and/or any other volumetric shape capable of self-centering itself with respect to an outlet opening or luer 20 of the syringe barrel 16. This seal prevents excess fluid from being forced out of the syringe 10 once the stopper 12 is bottomed in the syringe barrel 16. Excess fluid expelled at the end of an injection can cause a phenomenon known as "reflux" when the stopper 12 springs back to shape and pulls that excess fluid back into the syringe 10. In the design of the present invention, the seal also allows the buildup of pressure within the fluid trapped between the stopper 12 and the syringe barrel 16, which in turn will lead to positive displacement of the fluid once pressure is released. This positive displacement of the fluid to prevent reflux is discussed in more detail below.

The flexible core member 32 includes a front portion 38, a back portion 40, and a central portion 42, positioned between the front portion 38 and back portion 40. The front portion 38 projects from the main body 26, such as along a longitudinal axis of the main body 26. The flexible core member 32 may be interconnected with the main body 26 via a flexible membrane 44 extending between the flexible core member 32 and the main body 26. The back portion 40 of this flexible core member 32 contacts the front forward end attachment portion 31 of the plunger rod 14. The inventive design of the self-centering nose portion 34 allows for a seal to be made when a small amount of force is applied to the stopper 12 and over the entire tolerance ranges of the stopper 12 and syringe barrel 16.

As discussed above, the sealing surface on the nose portion 34 comes into contact with the interior surface 36 or back surface of the conical luer 20 at the front end of the syringe barrel 16, shown in FIG. 1. Since it is possible that the interior surface 36 of the luer 20 and the nose portion 34 of the stopper 12 will not be perfectly concentric, in one embodiment, the nose portion 34 of the stopper 12 may be capable of moving laterally in order for it to make full contact with the interior surface 36 of the luer 20. In a further embodiment, the flexible core member 32 and the flexible membrane 44 may allow the nose portion 34 to move in a substantially lateral direction. In yet another embodiment, the partially spherical shape of the nose portion 34 assures full contact between the nose portion 34 and the interior surface 36 of the luer 20 even when the nose portion 34 has rotated or shifted prior to making contact.

The inventive design of the stopper 12 of the present invention is an improvement over current stoppers as these current stoppers typically have a conical tip and work to seal only when the stopper and barrel are perfectly concentric. In prior designs, if the two components are not exactly aligned, there will not be a proper seal unless higher forces are applied to the stopper in order to deform it into a shape that will seal with the barrel luer taper.

According to a first embodiment of the stopper 12, as illustrated in FIGS. 2A, 2B, and 3, and a second embodiment of the stopper 12, as illustrated in FIGS. 4A and 4B, the main body 26 includes at least a first rib 46 extending radially outward and substantially around a perimeter of the main body 26. This first rib 46 is adapted for forming an active seal with the syringe barrel 16. As used herein, the phrase "active seal" means that seal pressure increases between the first rib 46 of the stopper and the inside surface of the syringe barrel 16 during increased user applied force to the plunger rod 14. In one embodiment, the main body 26 includes a second rib 48 extending substantially around a perimeter of the main body 26. The first rib 46 and the second rib 48 may be axially spaced apart along the length of the main body 26.

A feature of the stopper design of the first embodiment illustrated in FIGS. 2A, 2B, and 3 is a forward extending skirt 50 extending from the closed front end 30 of the main body 26. Due to the elasticity and/or flexibility of the forward extending skirt 50, the forward extending skirt 50 is capable of deforming by deflecting radially inwardly toward and substantially in contact with an outer portion 52 of the main body 26. Such deflection may occur upon insertion of the stopper 12 within the syringe barrel 16 to form an air pocket 53 to trap an air bubble therein. The air bubble trapped within air pocket 53 assists in the anti-reflux capabilities of the present invention as discussed in detail below. Upon insertion of the stopper 12 into the syringe barrel 16, the forward extending skirt 50 may be adapted to create a positive pressure within the syringe barrel 16.

In one embodiment, the main body 26 includes at least one undercut portion 55 extending axially inward from the open rearward end 28. The undercut portion 55 is adapted to engage the front forward end attachment portion 31 of the plunger rod 14 for locking the front forward end attachment portion 31 of the plunger rod 14 within the stopper 12. According to one embodiment, as shown in FIG. 3, the undercut portion 55 can include a reverse taper 56 adapted for cooperation with at least one deflecting arm 130 associated with the front forward end attachment portion 31 of the plunger rod 14.

The stopper 12 of the present invention may also be adapted to reduce and/or prevent mid-stream reflux. Mid-stream reflux occurs if the flush solution is not fully infused and the clinician does not clamp the line while the stopper is moving. Traditional syringe designs will generate reflux as the friction force on the stopper outer diameter and the plunger rod forces on the stopper center "stretch" the stopper nose. In order to overcome the static and dynamic friction to cause the stopper movement, the plunger rod force must be larger than the friction force, and this force imbalance is offset by the fluid back pressure and the stopper stretching. The difference is small, but measurable. As shown in FIG. 3 of the present application, a gap 94 is provided between a back portion 93 of the flexible core member 32 of the stopper 12 and the face 95 of the front forward end attachment portion 31 of the plunger rod 14. Because of this gap 94 and the flexibility of the flexible membrane 44 attaching the flexible core member 32 to the stopper main body 26, the flexible core member 32 is able to deflect proximally and store potential energy that is released in the form of positive displacement as soon as the plunger rod 14 force is ceased. Accordingly, during use of the syringe 10, due to gap 94, the plunger rod 14 does not directly apply a forward force to the flexible core member 32. Instead, the plunger rod 14 applies a forward force to the interior side portion of the stopper 12 which, in turn, applies a pulling force to the flexible core member 32 via flexible membrane 44. Thus, during the application of pressure to the plunger rod, the flexible core member 32 is slightly retracted into the gap 94. Once the forward force is suspended, the flexible core member 32 continues this forward motion and prevents mid-stream reflux.

According to one aspect of the invention, as depicted in FIGS. 2B, 3, and 4B, the interior portion of the main body 26 includes an inner surface 132 having a taper 198 adapted for contact with a taper 196 on the front forward end attachment portion 31 of the plunger rod 14. These contacting tapers 196, 198 cooperate together such that the stopper 12 applies a radial force to the syringe barrel 16 to form an active seal therewith upon the application of a forward force to the plunger rod 14. The active seal aspect of the invention is discussed in detail below.

In accordance with a second embodiment of the invention, as illustrated in FIGS. 4A and 4B, the flexible membrane 44A may extend from the flexible core member 32 to the sidewall portion 57A of the main body 26 terminating at the first rib 46A. In one arrangement, the flexible membrane 44A, first rib 46A, and sidewall 57A are integrally formed. In a further configuration, the forward extending skirt 50 of the first embodiment is not included.

Figure 5A:
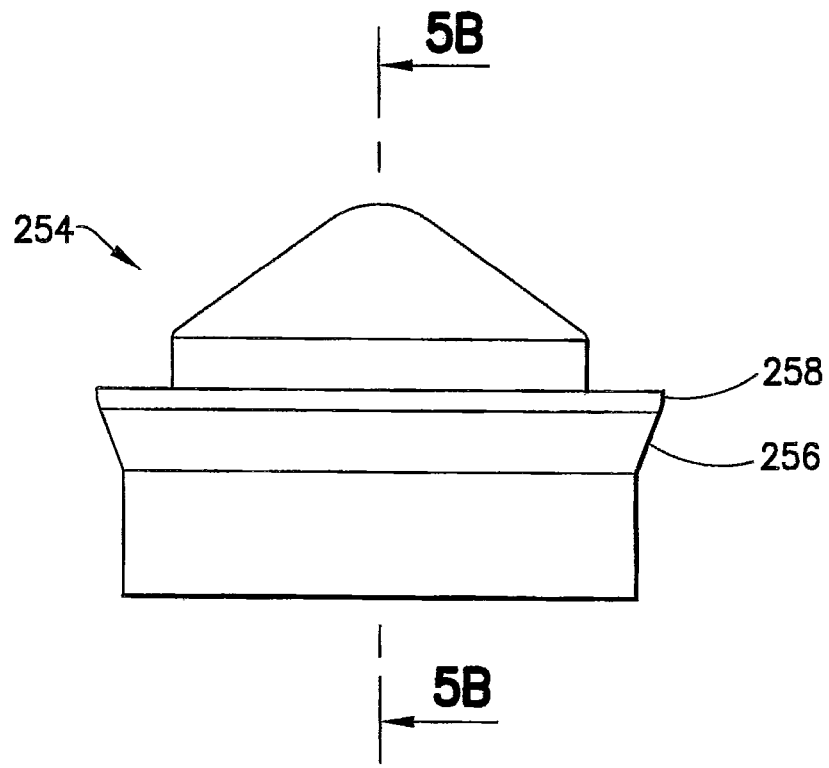
FIG. 5A is a side view of the stopper according to a third embodiment of the invention in accordance with an embodiment of the present invention.
Figure 5B:
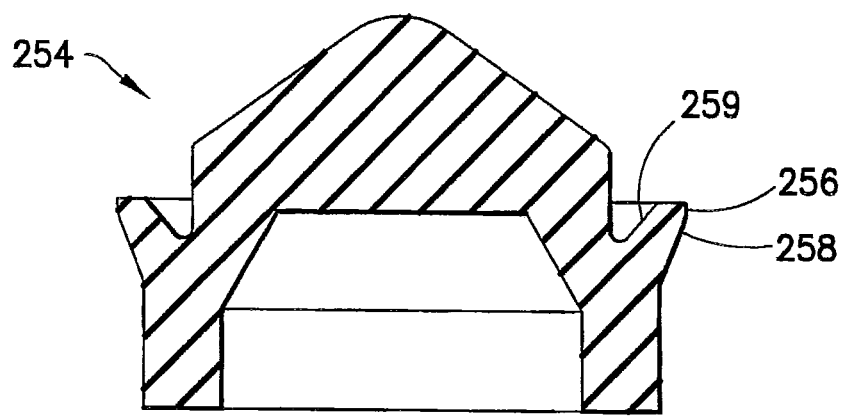
FIG. 5B is a cross-sectional view of the stopper taken along line 5B-5B of FIG. 5A.

According to a third embodiment of the invention, as illustrated in FIGS. 5A and 5B, an active seal achieves the same result as that of the previously discussed embodiments, but with a different mechanism, commonly referred to as a "lip seal" when used in hydraulic applications. The stopper, generally indicated as 254, includes this lip seal. The front seal 256 of the stopper 254 is located on the leading edge of a flexible arm 258. Initial sealing pressure is generated by the interference of the flexible arm 258 with the wall of the syringe barrel 16, as shown in FIG. 1. When the pressure in the syringe barrel 16 increases, this pressure applies an outward radial force to the inside 259 of the flexible arm 258. This outward force will increase the force with which the seal 256 presses against the inside wall of the syringe barrel 16.

Figure 6B:
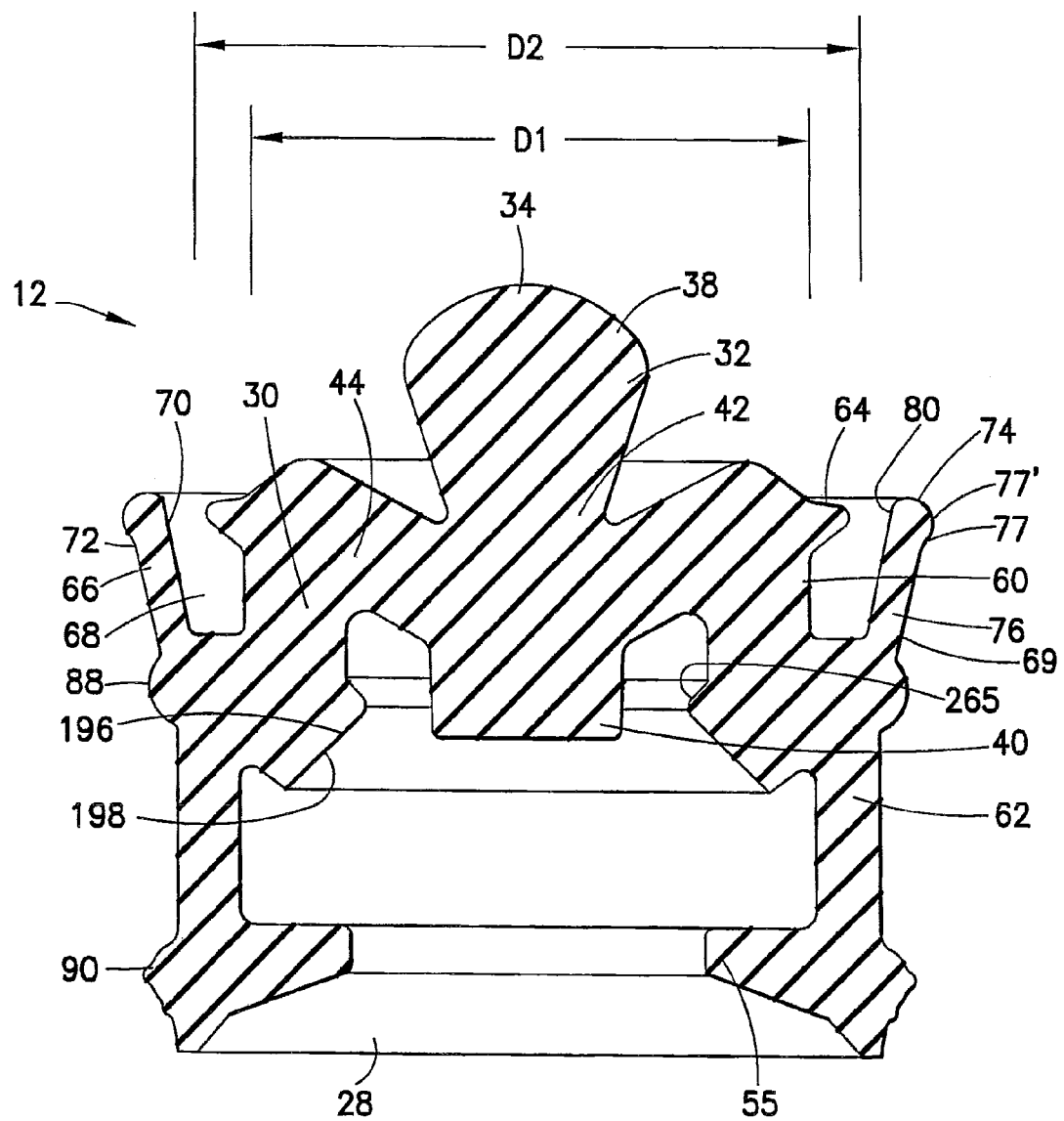
FIG. 6B is a cross-sectional side view of a stopper having an exterior design of FIG. 6A taken along line 6B-6B of FIG. 6A and having an interior design according to the first embodiment of the invention shown in FIG. 2B.

Reference is now made to FIGS. 6A-6F and 7-9 which show the stopper 12 according to a fourth embodiment of the invention. In this embodiment, the stopper 12 includes a main body 26 having a closed front end 30. The main body 26 can include an open rearward end 28 which is adapted to receive a front forward end attachment portion 31 of the plunger rod 14. As stated above, the front forward end attachment portion 31 is capable of attachment to the stopper 12. The main body 26 includes a first body portion 60 having a first diameter D1, as shown in FIG. 6B, and a second body portion 62 having a second diameter D2, as shown in FIG. 6B, which is larger than the first diameter of the first body portion 60. A shoulder 64 extends around a perimeter of the first body portion 60 of the main body 26. Preferably, this shoulder 64 extends in a radially outward direction with respect to the first body portion 60.

As stated above with respect to the description of the first embodiment, a flexible core member 32 is integrally formed with the main body 26 adjacent the closed front end 30. The flexible core member 32 includes a nose portion 34 extending from the closed front end 30 which is adapted for contacting an interior surface 36 of an outlet opening, such as a luer 20 of the syringe barrel 16. The flexible core member 32 may be formed from a flexible material and the nose portion 34 may include a semi-spherical self-centering profile to create a positive seal with the luer 20 at the forward end of the syringe barrel 16.

Figure 7:
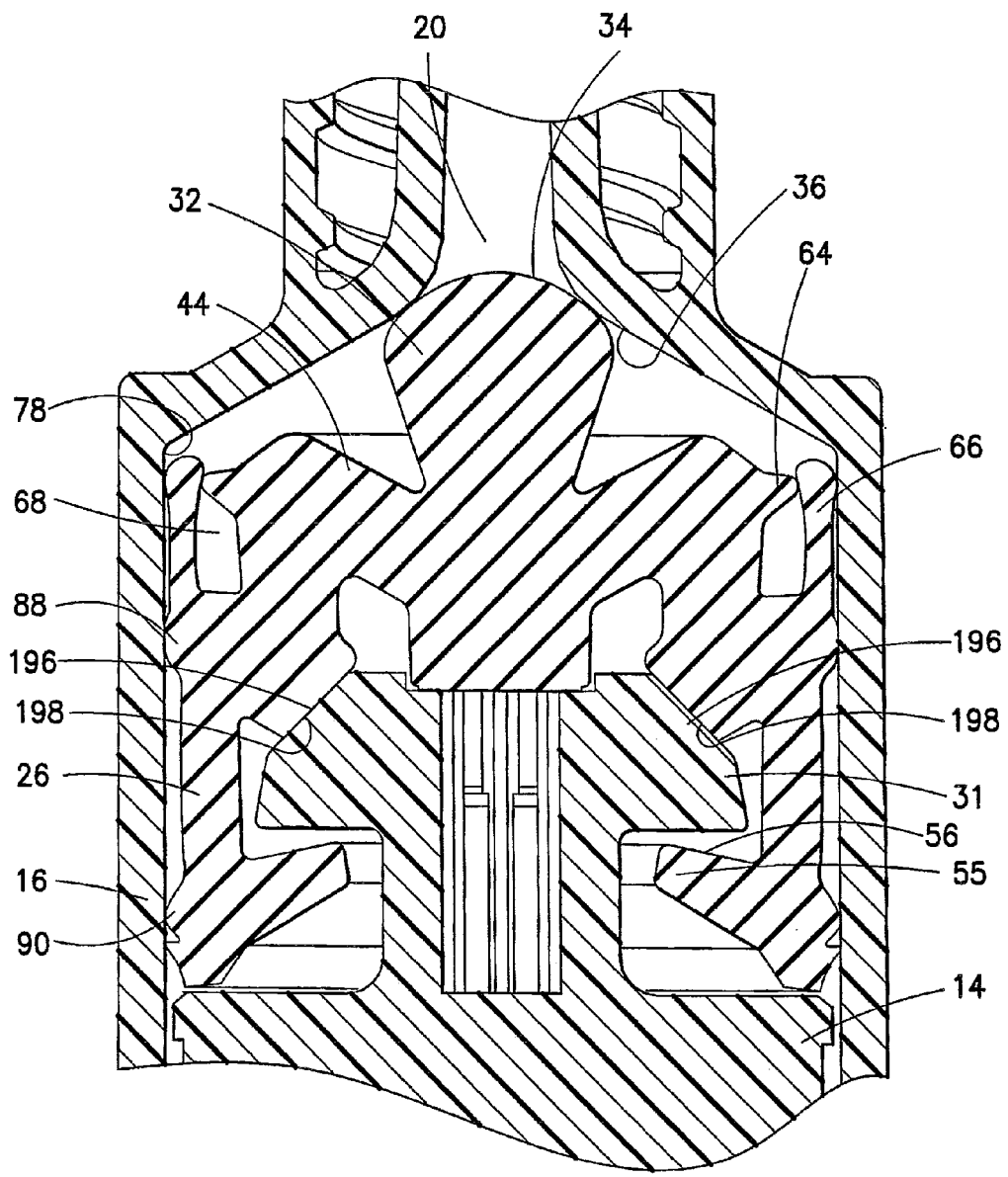
FIG. 7 is a cross-sectional side view of the stopper of FIG. 6B positioned within a syringe barrel.
Figure 8:
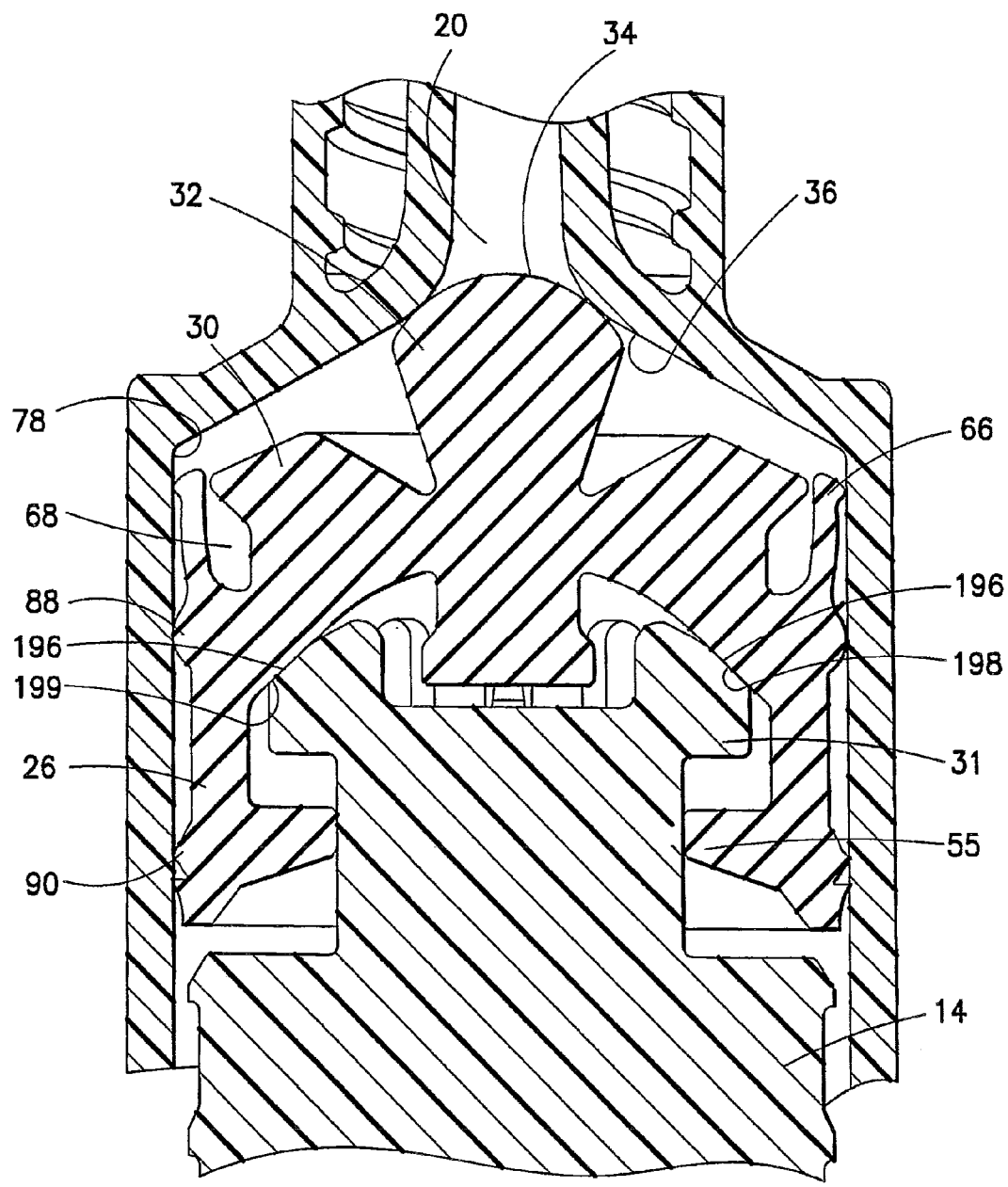
FIG. 8 is a cross-sectional side view of the stopper of FIG. 6C positioned within a syringe barrel.
Figure 9:
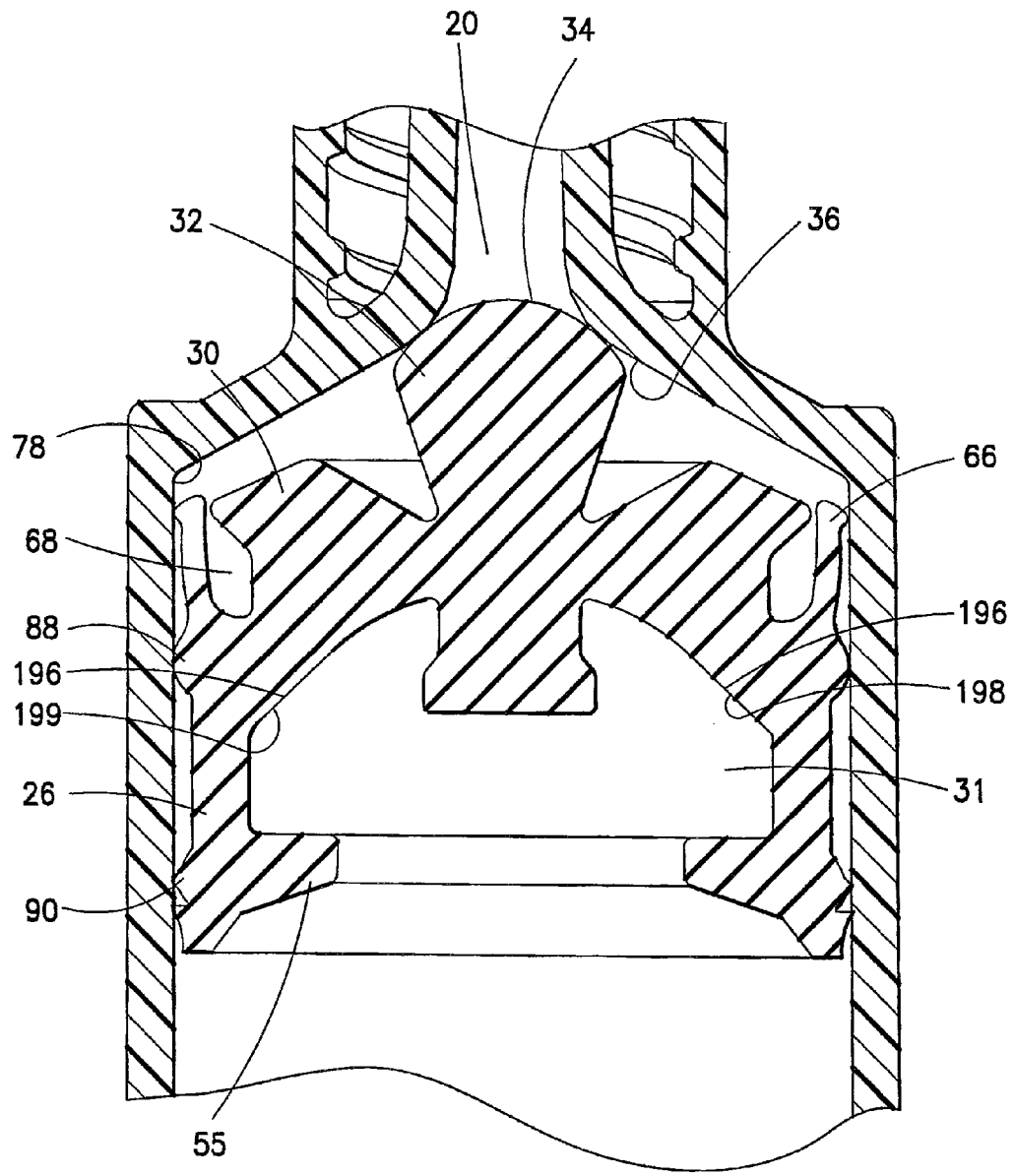
FIG. 9 is a cross-sectional side view of the stopper of FIG. 6D positioned within a syringe barrel.

The stopper 12 of the fourth embodiment, shown in FIGS. 6A-6E, differs from the first embodiment in that the stopper 12 includes at least one perimetrical skirt 66 extending from the second body portion 62 toward the front end 30 of the main body 26. This perimetrical skirt 66 cooperates with the shoulder 64 for trapping air pockets or an air bubble 68 therebetween upon insertion and/or movement of the stopper 12 within and through the syringe barrel 16. In this manner, upon release of a forward force on the plunger rod 14, fluid remaining within the syringe barrel 16 is forced through the luer 20 through positive displacement thereof. As shown in detail in FIGS. 6B-6D, the skirt 66 may include an inner surface 70 and an outer surface 72 and may be formed from a flexible and/or elastic material capable of deflecting radially inward. The inner surface 70 of the perimetrical skirt 66 may substantially contact the shoulder 64 to trap at least one air pocket/bubble 68. In one embodiment, the skirt 66 includes a lip portion 74 and a tail portion 76. The lip portion 74 may include an outwardly extending bump or first rib 77. An outer surface 77' of the first rib 77 may be adapted for contact with an inner surface 78 of the wall of the syringe barrel 16, shown in FIG. 1. This first rib 77 establishes a single line of contact between the perimetrical skirt 66 and the inner surface 78 of the wall of the syringe barrel 16, as shown in FIGS. 7-9. This first rib 77 functions to keep an outer surface 69 of the perimetrical skirt 66 adjacent the tail portion 76, positioned a predetermined distance apart from the inner surface 78 of the wall of the syringe barrel 16. This minimizes the area of contact between the perimetrical skirt 66 and the syringe barrel 16 to reduce break-loose forces and reduce static friction of the perimetrical skirt 66 with respect to the syringe barrel 16. The particular design of the perimetrical skirt 66 may allow for a clearer observation of the dose setting. In one embodiment, the perimetrical skirt 66 has a relatively linear shape and extends in a cylindrical manner about the first body portion 60 of the main body 26. According to another embodiment, the inner surface 70 of the perimetrical skirt 66 does not necessarily contact the main body 26 to form the air pocket or chamber 68, but is close enough to the main body 26 such that surface tension keeps the chamber 68 closed off and traps an air bubble therein.

Figure 6C:
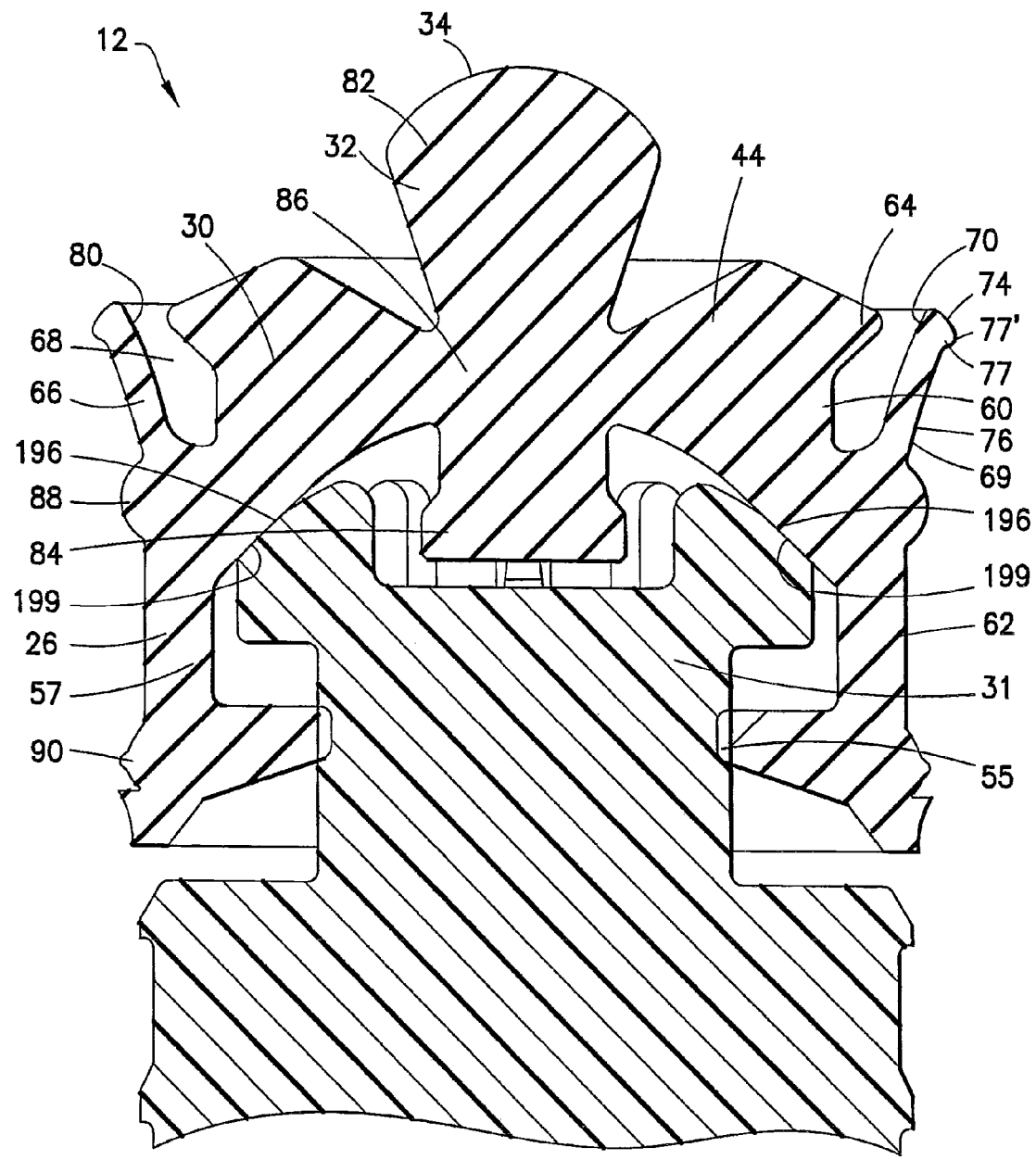
FIG. 6C is a cross-sectional side view of a stopper having an exterior design of FIG. 6A taken along line 6B-6B of FIG. 6A and having an interior design according to the second embodiment of the invention shown in FIG. 4B in combination with one type of an attachment portion of a syringe plunger rod.

As shown in FIGS. 6B-6D, the perimetrical skirt 66 of the stopper 12 is dimensioned to have a predetermined contact area 80 for cooperation with the shoulder 64. The contact area 80 is adapted for forming a predetermined gap sufficient for trapping air and allowing for communication of pressure from an air chamber to a fluid chamber.

Figure 6E:
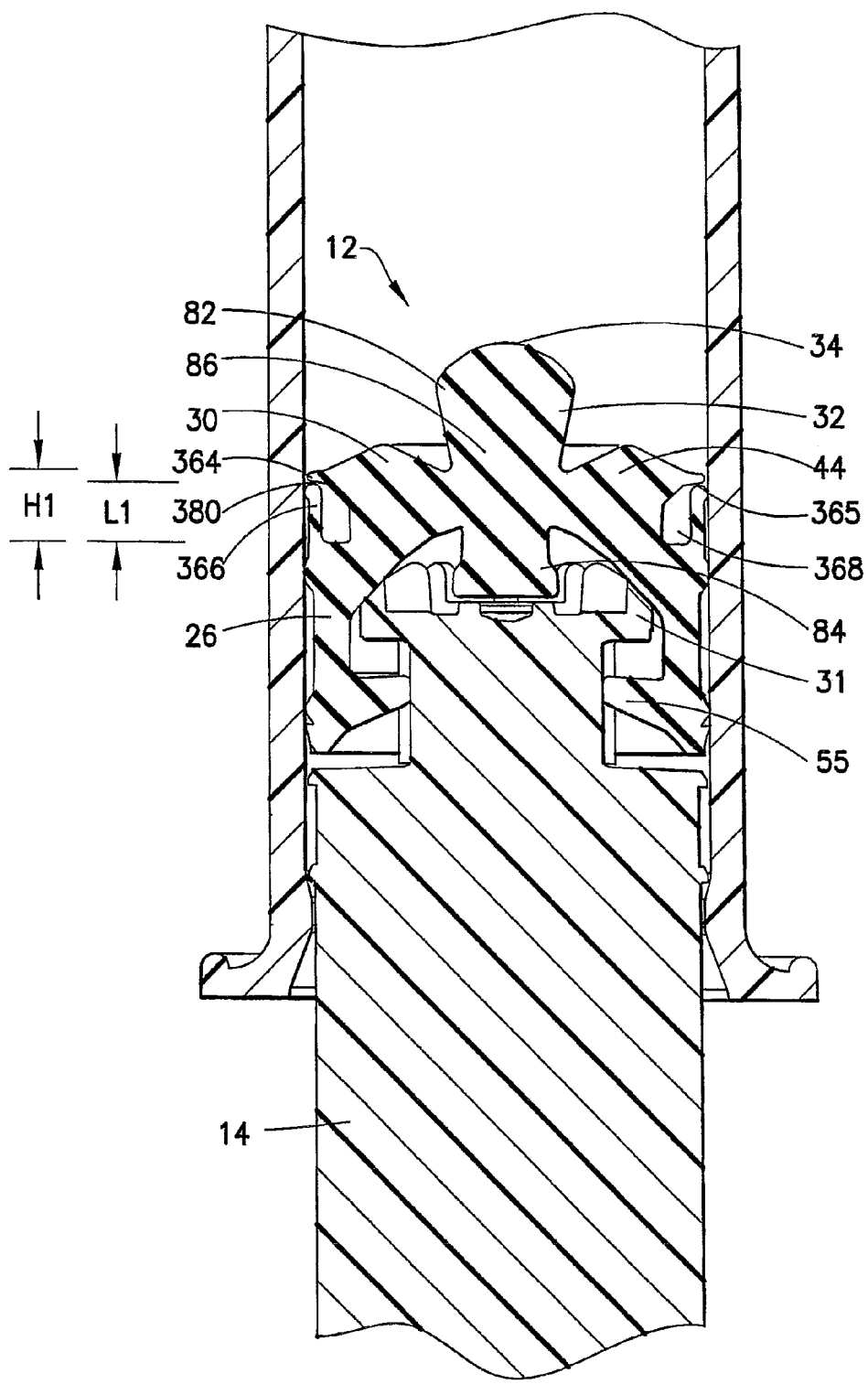
FIG. 6E is a cross-sectional side view of a stopper assembly having a modified skirt in accordance with an embodiment of the present invention.

FIG. 6E shows a modification of the stopper 12 of the fourth embodiment wherein the skirt 366 has a predetermined length L1 which is less than the length L2 of the perimetrical skirt 66 of FIGS. 6B-6D and less than the height H1 of the shoulder 64 such that the predetermined contact area 380 contacts a bottom surface 365 of the shoulder 364 to form the air pressure chamber 368.

Figure 6F:
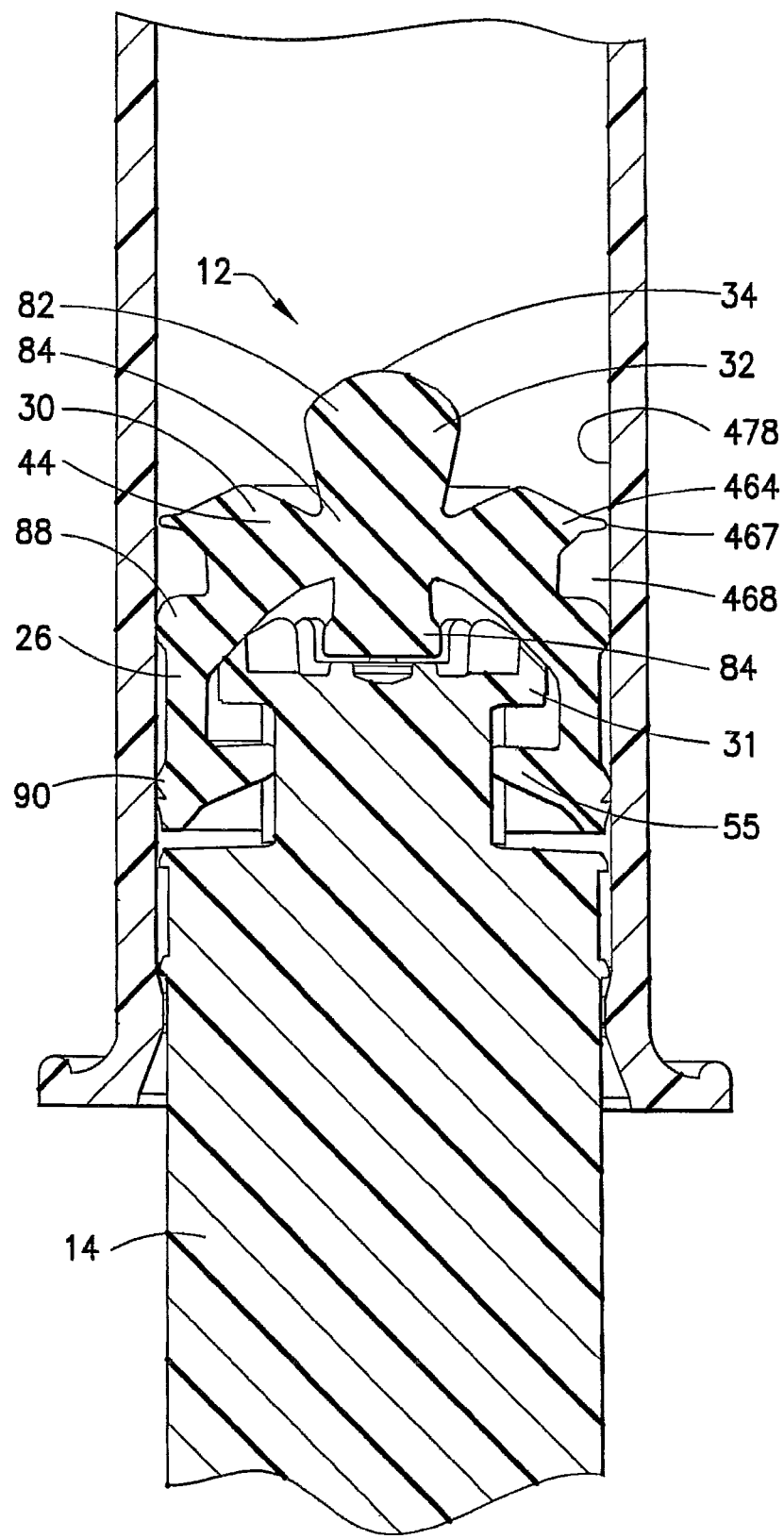
FIG. 6F is a cross-sectional side view of a stopper assembly in which the skirt has been eliminated in accordance with an embodiment of the present invention.

According to another arrangement, as shown in FIG. 6F, an air pressure chamber 468 can be created solely by the cooperation of the radially extending shoulder 464 with the inner surface 478 of the syringe barrel 16. In this configuration, the tip 467 of the shoulder 464 does not have to actually contact the inner surface 478 of the wall of the syringe barrel 16 in order to create the air pressure chamber 468, but rather only needs to be within a certain distance with respect to this inner surface to close off the air pressure chamber 468.

Referring again to FIGS. 6A-6F, the flexible core member 32 of the stopper 12 of the invention includes a front portion 82, extending above the main body 26, a back portion 84, and a central portion 86 positioned between the front portion 82 and back portion 84. The flexible core member 32 is interconnected with the main body 26 and, in particular, with the first body portion 60 thereof via a flexible membrane 44 extending between the central portion 86 of the flexible core member 32 and the first body portion 60 of the main body 26. The inventive design of the self-centering nose portion 34 allows for a seal to be made between the nose portion 34 and the interior surface 36 of an outlet opening or luer 20 when a small amount of force is applied to the stopper 12 and over the entire tolerance ranges of the stopper 12 through the plunger rod 14 and syringe barrel 16. As discussed above in relation to the first embodiment, the partially spherical surface shape of the nose portion 34 of the flexible core member 32 ensures full contact between the nose portion 34 and the interior surface 36 of the luer 20, even when the nose portion 34 has rotated or shifted prior to making contact.

The flexible membrane 44 and the air pocket/bubble 68 are adapted for storing potential energy such that upon release of a positive pressure on the plunger rod 14 and release of the seal between the nose portion 34 of the flexible core member 32 and the interior surface 36 of the luer 20, release of this potential energy forces fluid within the syringe barrel 16 through the luer 20 and any attached catheter.

According to the fourth embodiment of this invention, the main body 26 includes at least a second rib 88 extending substantially radially outward and substantially around a perimeter of the second body portion 62 of the main body 26. This second rib 88 is adapted to form an active seal with the inner surface 78 of the syringe barrel 16. The at least one air pocket/bubble 68 is positioned in a forward position with respect to the second rib 88. The main body 26 may include a third rib 90 such that the second rib 88 and third rib 90 extend radially outward around the perimeter of the outer diameter D2, as shown in FIG. 6B, of the second body portion 62 of the main body 26 and are axially spaced apart along this second body portion 62.

As shown in FIGS. 6B-6F and FIGS. 7-9, the main body 26 of the stopper 12 can include at least one undercut portion 55 extending axially inward of the open rearward end 28. This undercut portion 55 is adapted for locking the front forward end attachment portion 31 of the plunger rod 14 within the stopper 12. According to one aspect, the undercut portion 55 may include a reverse taper 56, as shown, for example in FIG. 7, which is adapted for cooperation with the front forward end attachment portion 31 of the plunger rod 14. Various designs of the front forward end attachment portion 31, according to the present invention, are discussed in detail below.

As shown in FIG. 6B and FIG. 7, the main body 26 may also include an inner surface having a taper 198 adapted for contact with a taper 196 on the front forward end attachment portion 31 of the plunger rod 14. These contacting tapers 196, 198 cooperate together such that the stopper 12 applies a radial force to the syringe barrel 16 to form an active seal therewith upon the application of a forward force to the plunger rod 14.

According to another aspect of the invention, as depicted in FIGS. 6C, 6D, 8, and 9, the taper 199 of the inner surface 132 of the main body 26 may be a continuous contour from a sidewall portion 57 of the main body 26 to the flexible core member 32. This continuous contour taper 199 is adapted for cooperating with taper 196 on the front forward end attachment portion 31 of the plunger rod 14 such that the stopper 12 applies a radial force to the syringe barrel 16 to form an active seal therewith upon the application of a forward force to the plunger rod 14.

An increase in pressure inside the syringe barrel 16 will cause the closed front end 30 of the stopper 12 to have a higher contact pressure with the inner surface 78 of the wall of the syringe barrel 16, thereby preventing leaks at the stopper 12 and syringe barrel 16 seal. The active seal of the present invention solves this problem by using a lower contact pressure between the stopper 12 and syringe barrel 16 when there are low fluid pressures in the syringe barrel 16, but higher contact pressure when the fluid pressure increases, such as during forward movement of the plunger rod 14 and stopper 12 through the syringe barrel 16.

In one embodiment, the active seal is achieved through the interaction of the front forward end attachment portion 31 of the plunger rod 14 and the inside of the stopper 12. According to one embodiment, as shown in FIG. 6B, the front forward end attachment portion 31 of the plunger rod 14 includes a forward leading surface taper 196 and corresponds to a taper 198 on the inside of the stopper 12. During use when the plunger rod 14 is being pushed, a forward leading edge applies force to the inside of the stopper 12. Due to the shape of the taper of the two surfaces 196, 198, the plunger rod 14 imparts a force that pushes the stopper 12 forward in the syringe barrel 16 and a force that pushes substantially outward in a radial direction. The outward force advances the stopper 12 forward of the second rib 88, and into the walls of the syringe barrel 16 which increases the sealing pressure. Likewise, as shown in FIGS. 6C and 6D, the taper 196 on the front forward end attachment portion 31 of the plunger rod 14 imparts a force to the continuous contour taper 199 of the inner surface 132 of the main body 26 such that the stopper 12 applies a radial force to the syringe barrel 16 to form an active seal therewith upon the application of a forward force to the plunger rod 14. High plunger rod forces are caused by high pressure in the syringe barrel 16, such that contact pressure therewith will increase as pressure in the syringe barrel 16 increases.

In a further embodiment, the perimetrical skirt 66 of the stopper 12 also acts as a lip seal. As the fluid pressure increases, increasing the air pressure in the air pocket/bubble 68, the skirt contact pressure at the interface of stopper 12 and syringe barrel 16 is increased, improving the sealing performance. Another advantage of this active seal is due to the application of the force of the plunger rod 14 only on the forward or second rib 88, which allows the back or third rib 90 to be "pulled" forward during injections. The pulling will also stretch the material of the back or third rib 90 reducing the effective force on the syringe barrel 16 and further reducing friction forces.

The stopper design of the present invention is intended to prevent reflux by creating positive displacement of fluid out of the front end of the syringe barrel (and into any attached catheter) after the stopper 12 has been bottomed in the syringe barrel 16 and force is released from the plunger rod 14. The features of the stopper 12 that act to create this positive displacement are the seal at the nose portion 34 of the stopper 12, the flex or relative movement of the stopper 12 between the nose portion 34 and the forward or second sealing rib 88, and potential energy in the form of pressurized fluid captured and stored prior to the release of the force from the plunger rod 14. The relative movement of the second rib 88, with respect to the nose portion 34 of the stopper 12, is achieved by means of the flexible membrane 44 that connects the outer forward or second rib 88 to the flexible core member 32 and nose portion 34. The energy storing is achieved by means of both the flexible membrane 44 and an air bubble or air pocket 68 that is trapped under the perimetrical skirt 66 just forward of the second rib 88.

The particular design of the fourth embodiment of the stopper 12 of the present invention has several advantages. For example, since the perimetrical skirt 66 may be substantially linear, without any radial flanges, wrinkling of the perimetrical skirt 66 is reduced and/or eliminated. In particular, the provision of the shoulder 64 on the first body portion 60 of the stopper main body 26 allows the perimetrical skirt 66 to have a relatively straight shape and the flexibility and/or elasticity of the perimetrical skirt 66 allows for flex in an inward direction to bring a contact area 80 of the perimetrical skirt 66, without deformation of the perimetrical skirt 66 itself, into contact with the shoulder 64. Another advantage of this design is that manufacturing of the stopper 12 is simplified. As only one molding tool plate is required for the bottom of the mold, the cost of the tooling is reduced.

The addition of the outwardly extending portion or bump 77 on the perimetrical skirt 66 minimizes the area of the perimetrical skirt 66 in contact with the inner surface 78 of the syringe barrel 16. This reduced contact area reduces break-loose forces and static friction and also provides a clear indication of the dose setting. Finally, the design of the interference and length of the perimetrical skirt 66 is such to maintain the proper gap to trap air and allow for communication of pressure from the air chamber to the fluid chamber.

An active seal of the stopper 12 within the syringe barrel 16 can be further achieved by the front forward end attachment portion 31 of the plunger rod 14, as described below, in combination with the particular interior design of the stopper 12. The front forward end attachment portion 31 is adapted for use with any of the stopper embodiments previously disclosed herein. The invention is particularly useful in situations wherein the syringe 10 is pre-filled and sterilized and the stopper 12 is inserted into the syringe barrel 16 prior to attachment of the plunger rod 14 to the stopper 12.

Figure 16A:
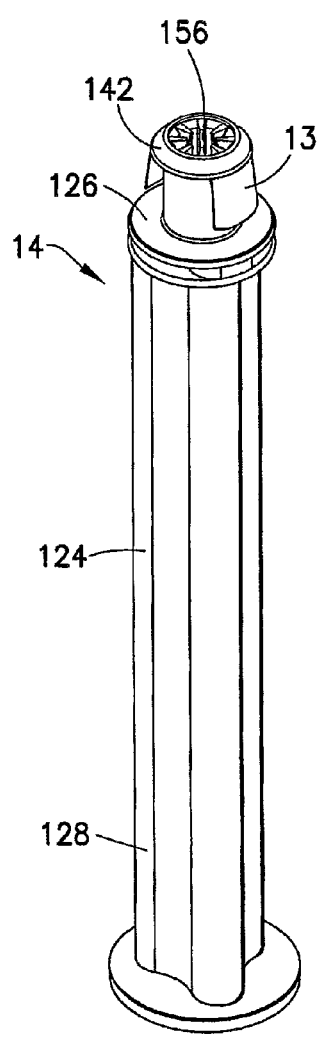
FIG. 16A is a perspective view of the plunger rod of FIG. 1.
Figure 16B:
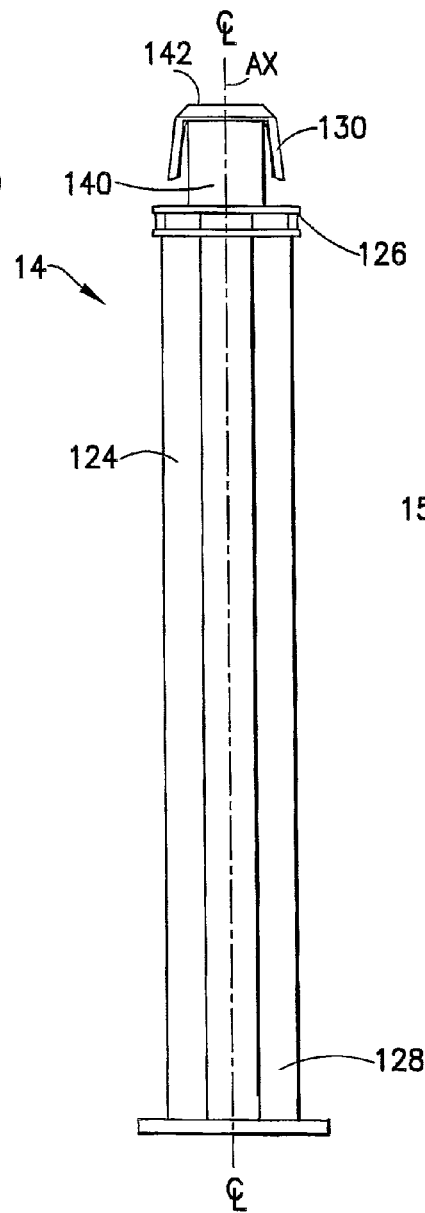
FIG. 16B is a side view of the plunger rod of FIG. 1.
Figure 16C:
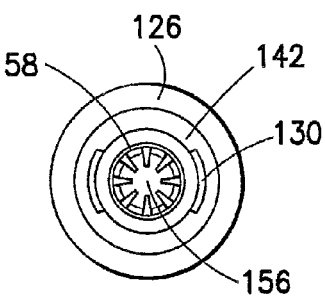
FIG. 16C is a top view of the plunger rod of FIG. 1.

As illustrated in FIGS. 16A-16C, the plunger rod 14 may include an elongated member 124 having a front end 126 and a back end 128 extending along a longitudinal axis AX, as shown in FIG. 16B. At least one deflecting arm 130 may be associated with the front end 126 of the elongated member 124. The deflecting arm 130 may be capable of deflecting radially inward during insertion of the plunger rod 14 into the stopper 12, and deflecting outward into contact with an inner surface 132 of the stopper 12, as shown in FIG. 3, after insertion into the stopper 12 to lock the plunger rod 14 within the stopper 12. FIGS. 16A-16C illustrate two deflecting arms 130, however, any number of deflecting arms 130 can be provided as needed to securely attach the plunger rod 14 within the stopper 12.

Referring back to FIG. 3, when the plunger rod 14 is inserted into the stopper 12, the deflecting arms 130 on the plunger rod 14 deflect and/or the stopper 12 deforms to allow the deflecting arms 130 to move into an undercut space 134 on the inside of the stopper 12. When the deflecting arms 130 enter the undercut space 134, the plunger rod 14 is locked in place and is prevented from separating from the stopper 12. When a user uses the syringe 10 to aspirate, the deflecting arms 130 on the plunger rod 14 will dig into the undercut surface 136 of the stopper 12 and on the inside of the stopper 12, preventing the plunger rod 14 from pulling out of the stopper 12. The bottom surface 133 of the deflecting arm 130 can be tapered to correspond with the shape of the undercut surface 136 of the stopper 12. The deflecting arms 130 can be implemented according to several designs, as discussed in detail below.

Figure 17A:
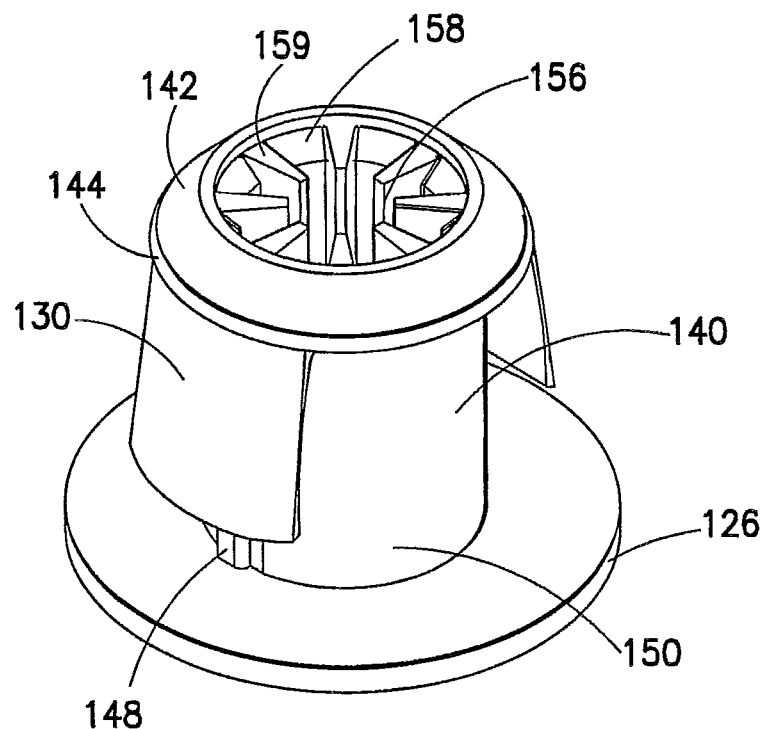
FIG. 17A is an enlarged perspective view of the attachment member for the plunger rod of FIG. 1 according to a first embodiment of the invention.
Figure 17B:
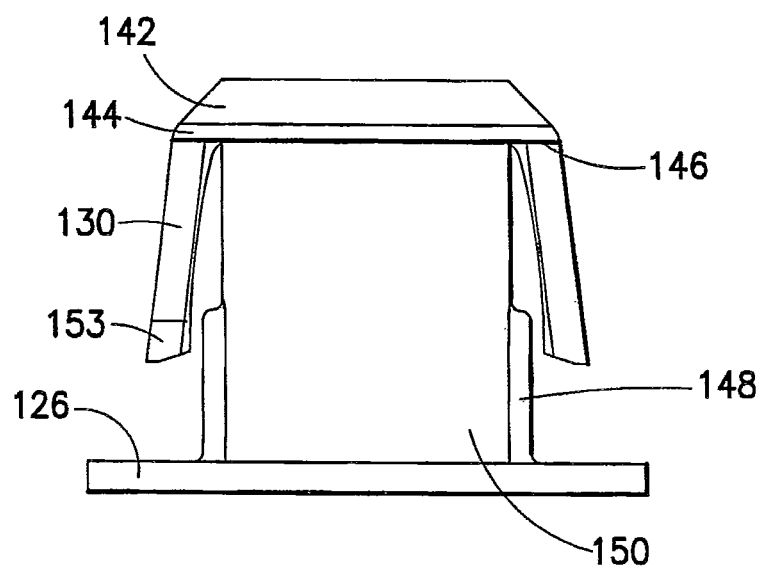
FIG. 17B is a side view of the attachment member of FIG. 17A.

According to a first embodiment, as illustrated in FIGS. 17A-17B, the front end 126 of the elongated member 124 includes a head member 140 extending from a front surface 144 of the front end 126. The head member 140 includes a rim member 142 extending along a front surface 144 thereof. The deflecting arms 130 may extend from a bottom surface 146 of the rim member 142 in a substantially downward direction. At least a first stop member 148 may be provided for limiting deflection of the deflecting arms 130 during insertion of the plunger rod 14 into the stopper 12. This first stop member 148 can be positioned adjacent to a rearward portion 150 of the head member 140.

The rim member 142 is preferably formed from an elastomeric material capable of forming an active seal with an inside surface of the stopper 12, as shown in FIG. 3. A reinforcement material 153 may also be provided at the contact area of the deflecting arms 130. Also, as shown in FIGS. 16A, 16C, and 17A, the rim member 142 and head member 140 may include a hollow portion 156 defined by at least one sidewall 158. The sidewall 158 has a plurality of inwardly extending ribs 159 extending radially inward toward the center of the hollow portion 156. According to one embodiment, this hollow portion 156 can come into contact with a back portion of the flexible core member 32 inside of the stopper 12.

Figure 18A:
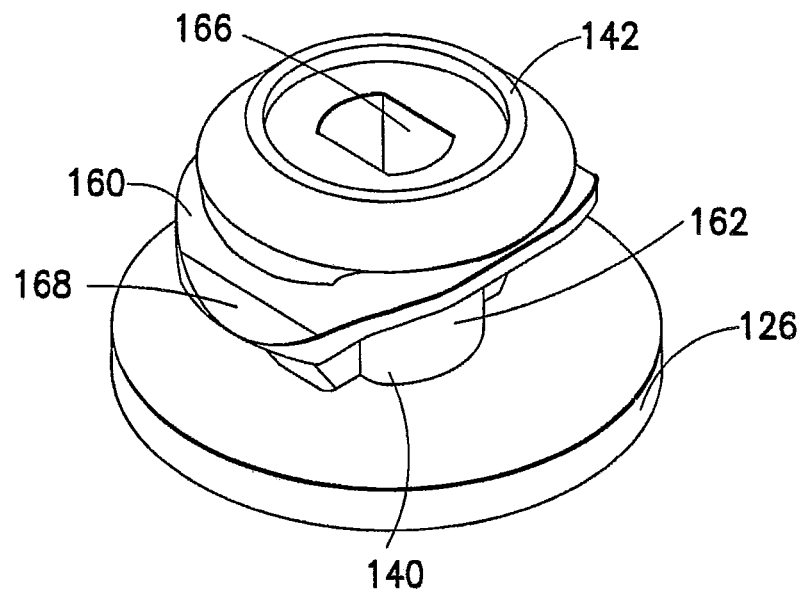
FIG. 18A is an enlarged perspective view of the attachment member for the plunger rod according to a second embodiment of the invention.
Figure 18B:
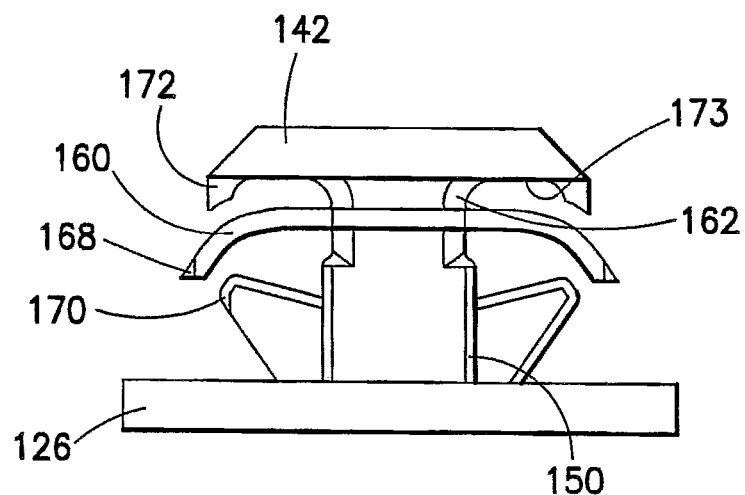
FIG. 18B is a side view of the attachment member of FIG. 18A.

According to a second embodiment, as illustrated in FIGS. 18A-18B, the at least one deflecting arm 160 extends radially outward from a center portion 162 of the head member 140. In this embodiment, the deflecting arm 160 may be a continuous member that extends through an aperture in the center portion 162 of the head member 140. A hollow portion 166 is also provided in the head member 140 and rim member 142 of this embodiment. The edges 168 of the deflecting arm 160 may also be formed from appropriate reinforcement material. A first stop member 170 extends outward from a rearward portion 150 of the head member 140. A second stop member 172 extends rearward from a bottom surface 173 of the rim member 142 to limit arm deflection in an opposite direction, such as during aspiration of the syringe 10.

Figure 19A:
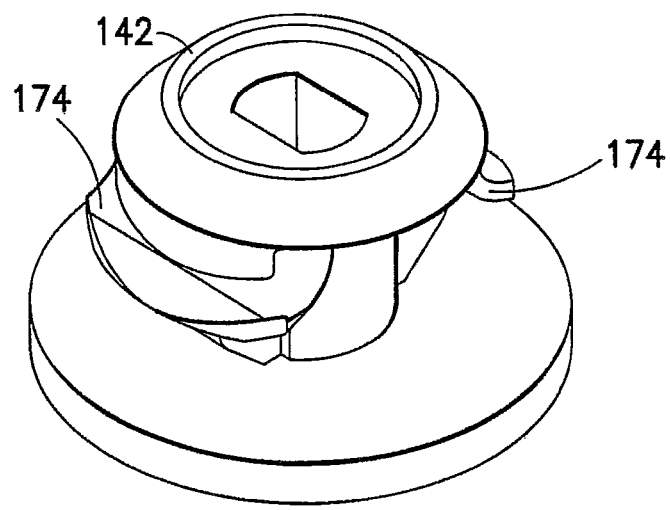
FIG. 19A is an enlarged perspective view of the attachment member for the plunger rod according to a third embodiment of the invention.
Figure 19B:
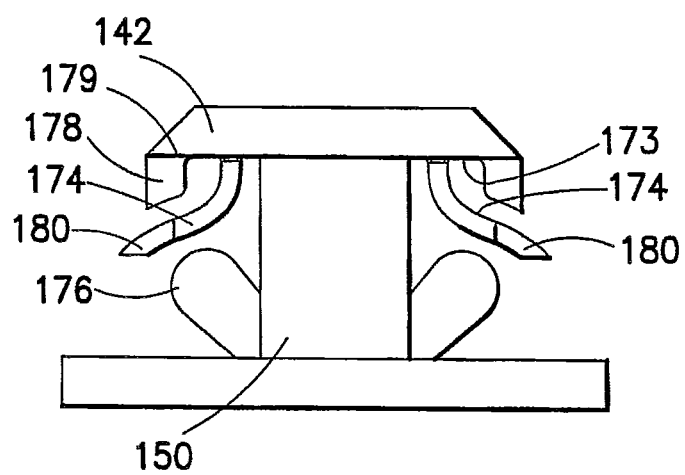
FIG. 19B is a side view of the attachment member of FIG. 19A.

According to a third embodiment, as illustrated in FIGS. 19A-19B, the at least one deflecting arm includes a pair of deflecting arms 174 extending in a downward and radially outward direction from the bottom surface 173 of the rim member 142. In this embodiment, a first stop member 176 extends outward from a rearward portion 150 of the head member 140. A second stop member 178 extends downward from an outer edge 179 of the rim member 142 for limiting deflection of the deflecting arms 174, such as during aspiration. The edges 180 of deflecting arms 174 are formed from appropriate reinforcement material.

Figure 20B:
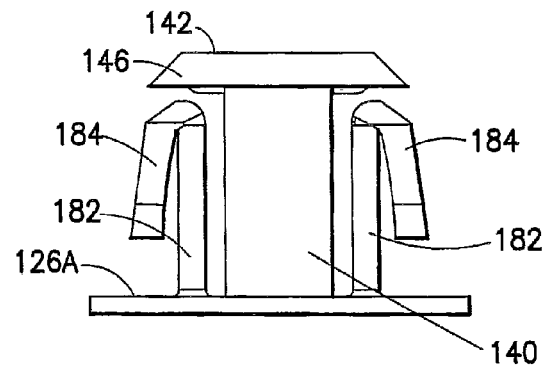
FIG. 20B is a side view of the attachment member of FIG. 20A.
Figure 20A:
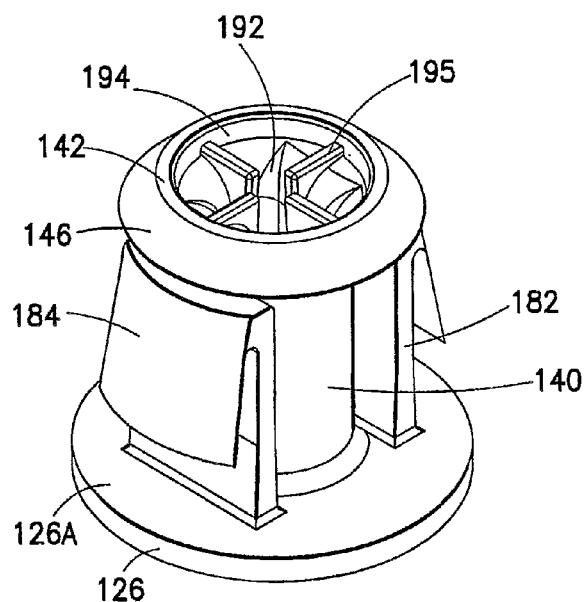
FIG. 20A is an enlarged perspective view of the attachment member for the plunger rod according to a fourth embodiment of the invention.
Figure 20C:
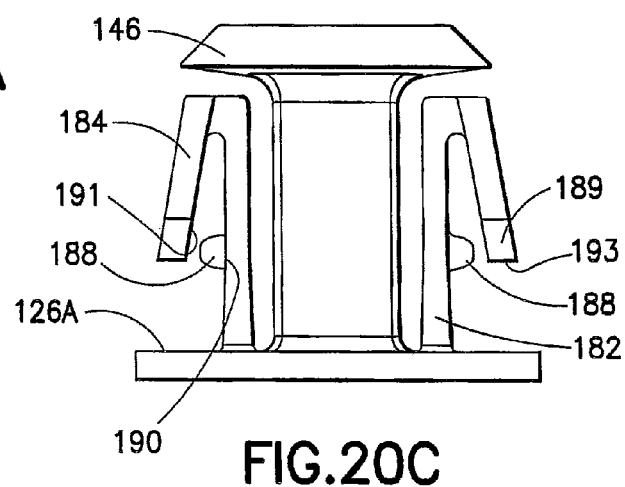
FIG. 20C is a side view of the attachment member of FIG. 20A including stop members.

According to a fourth embodiment, as illustrated in FIGS. 20A-20C, the front end 126 of the elongated member 124 includes a base surface 126A having a head member 140 extending therefrom. The head member 140 includes a rim member 142 extending along a front surface 144 thereof. In this embodiment, the at least one deflecting arm includes a first arm portion 182 extending from the base surface 126A parallel with the head member 140 and a second arm portion 184 attached to a front portion 186 of the first arm portion 182 extending in a rearward and outward direction with respect to the first arm portion 182. A stop member 188, as shown in FIG. 20C, may be provided to limit deflection of the second arm portion 184 during insertion of the plunger rod 14 into the stopper 12. This stop member 188 is positioned adjacent an outer surface 190 of the first arm portion 182 at a location adjacent to an inner surface 191 of the second arm portion 184. Portions of the second arm portion 184 may include a reinforcement material 189, as necessary. Additionally, the bottom surface 193 of the second arm member 184 may be flat or tapered as desired, depending upon the shape of the mating surface undercut portion 136 of the stopper 12.

These double deflecting arm portions 182, 184 can deflect from the base of the front end of the plunger rod 14 and from the top of the arm attached to the base of the front end geometry. During insertion, a normal load is exerted on the outside surface of the second arm portion 184. When the pressure is exerted at the top or front portion 186 of the second arm portion 184, first arm portion 182 deflects inwardly. As the pressure moves down the surface of second arm portion 184, this second arm portion 184 will begin to deflect. Deflection is greatest when both arm portions 182, 184 are at maximum deflection. During aspiration, a compressive and/or torsional load is exerted on the arm portions 182, 184 and the first arm portion 182 will begin to deflect inwards while second arm portion 184 digs into a stopper undercut surface, such as undercut surface 136, as shown in FIG. 3. Deflection, however, is limited by the contact between second arm portion 184 and the inner surface 132 of the wall of the stopper 12. As discussed above, a stop member 188 may be provided for reducing stresses on the arm portions 182, 184 by limiting the deflection of the arm portions 182, 184 where necessary, making deflection independent of the surface pressure during insertion and after the stop member 188 and second arm portion 184 are in contact with each other.

The embodiment shown in FIGS. 20A-20C can also include an opening 192 in the head member 140 and rim member 142. This opening 192 is defined by a circular sidewall 194 and a plurality of ribs 195 extending inwardly from this circular sidewall 194 toward the opening 192.

Figure 21A:
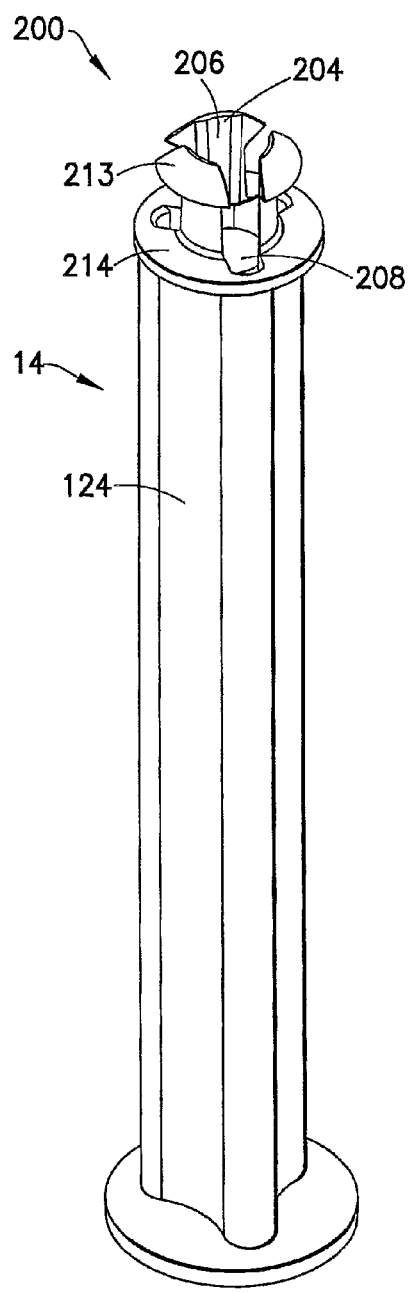
FIG. 21A is a perspective view of the plunger rod including an attachment member according to a fifth embodiment of the invention.
Figure 21B:
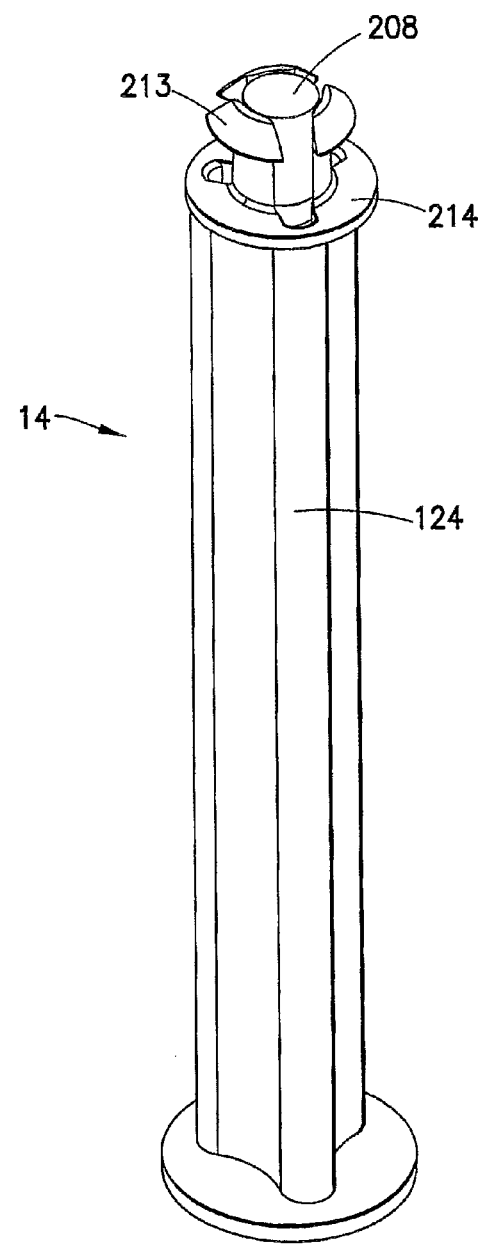
FIG. 21B is a perspective view of the plunger rod of FIG. 21A including a reinforcing slug located within the attachment member.
Figure 21E:
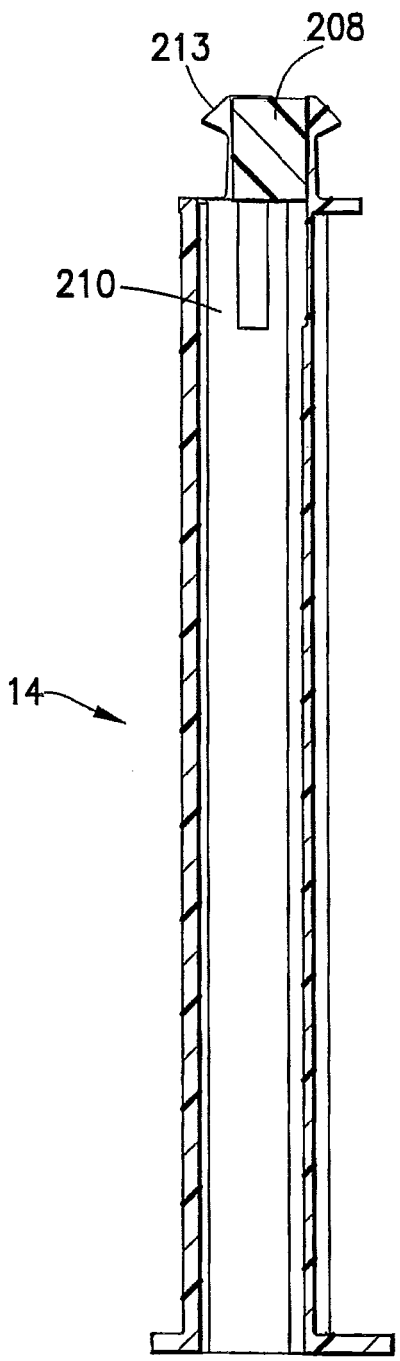
FIG. 21E is a cross-sectional side view taken along line 21E-21E of FIG. 21C.
Figure 21F:
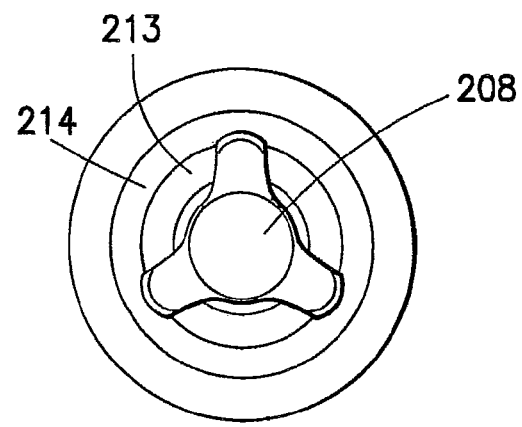
FIG. 21F is a top view of the attachment member of FIG. 21B.

According to a fifth embodiment, as illustrated in FIGS. 21A-21F, the attachment portion, generally indicated as 200, of the plunger rod 14 can include a deflecting arm 204 which can include a single circular deflecting arm or a plurality of deflecting arms extending from the front end 126 of the elongated member 124. This deflecting arm 204 defines a space 206, and during attachment of the plunger rod 14 within the stopper 12, the deflecting arm 204 deflects inwardly toward the space 206. When the deflecting arms 204 have reached maximum deflection and are housed in the undercut space 134 on the inside of the stopper 12, a slug 208 may be inserted into this space 206 to support the deflecting arm 204 and prevent it from collapsing and separating from the stopper during use of the syringe 10. According to one embodiment, as illustrated in FIGS. 21D-21E, the elongated member 124 includes a hollow portion 210 and the slug 208 is pre-molded within this hollow portion 210. After the attachment of the plunger rod 14 to the stopper 12, an application force is applied within the hollow portion 210 to force the slug 208 into the space 206. Alternatively, the slug 208 may be separately molded and subsequently inserted.

Another aspect of the present invention is a new plunger body design as shown in FIGS. 22A-22B, 23A-23B, 24A-24B, and 25. The plunger rod 14 is preferably made of a rigid thermoplastic material. This design, as discussed in detail below, consists of a hollow elongated plunger rod body wherein the hollow portion is defined by a plurality of longitudinally extending lobes, and preferably an odd number of lobes are provided. In traditional solid body four-rib plunger designs, a user may apply a side load during aspiration that may be normal to the edge of a rib, causing minimal side loading deflection, or normal to the region in between the ribs, i.e., 45° from the rib, causing maximum side loading deflections. The present invention introduces a plunger body comprising an elongated body portion 234 having a front end 236, a back end 238, and a sidewall portion 239 extending along a longitudinal axis between the front end 236 and the back end 238. The sidewall portion 239 comprises a plurality of longitudinally extending lobes 240 defining an interior hollow portion 242. An attachment member 244 is secured to the front end 236 and is adapted for attachment of the plunger rod 14 to the stopper 12. A cover member 246 is secured to the back end 238 of the elongated body portion 234 for covering the interior hollow portion 242 and providing a thumb press area 248 for application of a force to the plunger rod 14 during use.

Figures 22A, 22B:
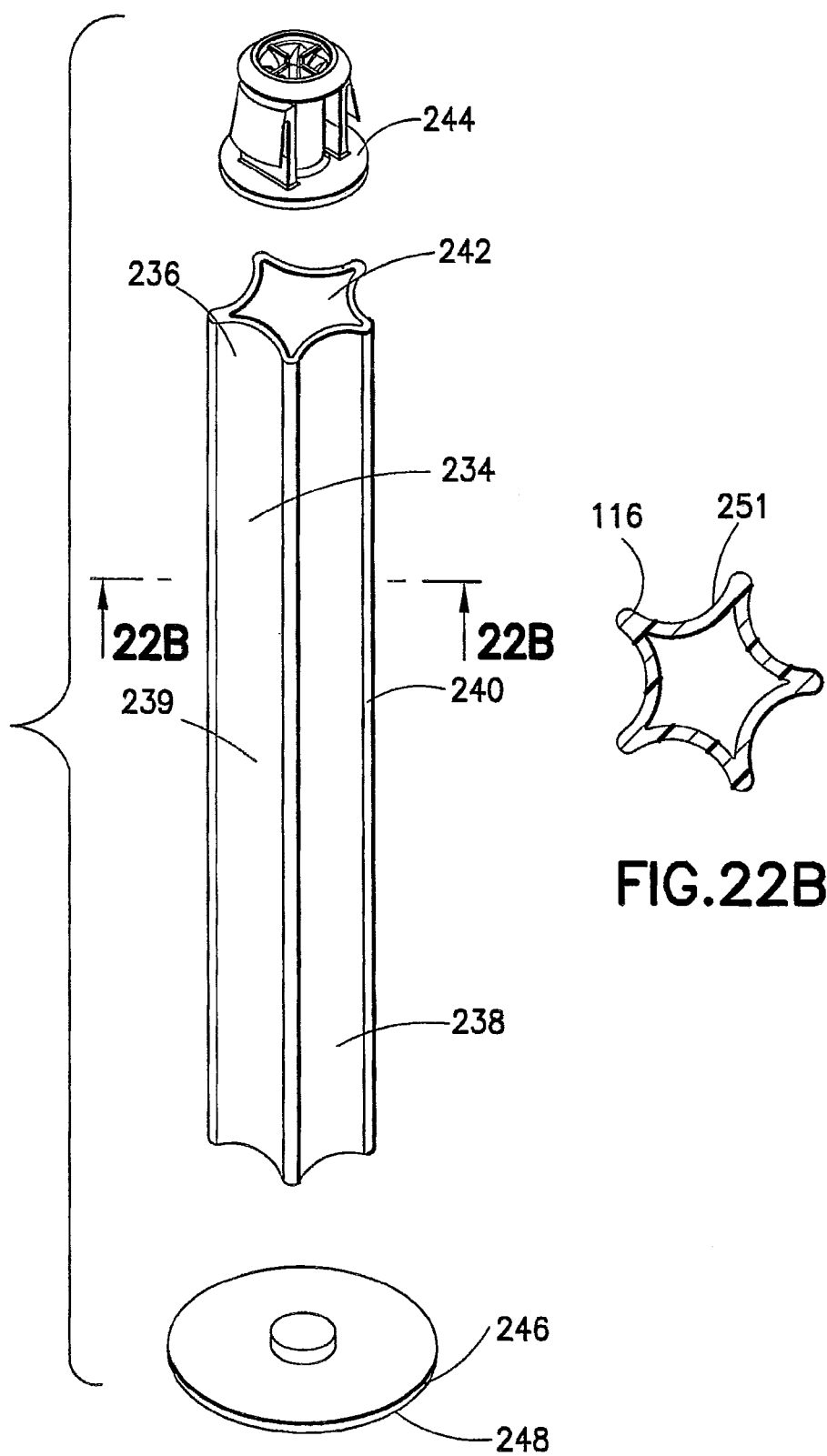
FIG. 22A is an exploded perspective view of the plunger rod according to one embodiment of the invention.
FIG. 22B is a cross-sectional view of the plunger rod of FIG. 21A taken along line 22B-22B.

The longitudinally extending lobes 240 preferably comprise an odd number of lobes spaced substantially equidistant with respect to one another. According to one embodiment, as shown in FIGS. 23A-23B, the plurality of longitudinally extending lobes 240 comprises a three-lobe design 250 positioned at approximately 120° with respect to one another. According to still another embodiment, as shown in FIGS. 22A-22B, the plurality of extending lobes 240 number at five, forming a five-lobe design 251, wherein the lobes 240 are spaced substantially equidistant with respect to one another. The lobes are positioned with respect to one another to form substantially uniform side loading deflection of the plunger rod 14. Providing an odd number of lobes 240 decreases the expected deflection when a load is applied to the region between the lobes 240 by introducing a lobe on the opposite side which supports the reaction load. The present invention also includes four-lobe hollow elongated plunger body designs 252, such as illustrated in FIGS. 24A-24B. Because the body portion of the plunger 14 includes a hollow portion 253, the advantages associated with the hollow design, as discussed above, would also be present in the four-lobe design 252. The hollow design also provides additional stiffness to the body portion 234 of the plunger rod 14 and several improvements, such as reduced product costs, easier manufacturing procedures, and the like as discussed in detail below.

The plunger rod 14 of the invention may be manufactured according to the following processes. In a first process, the elongated body portion 234 and the front end attachment member 244 are integrally molded from the same material. The plunger rod 14 is designed to have an interior hollow portion 242 so that a core pin can be driven up the center of the plunger rod 14 during injection molding. This allows the plunger rod 14 to be molded "standing up", which results in a reduction in cycle time due to additional cooling in the core pin and an increase in volume due to an increase in cavity number. To cover the core pin opening or interior hollow portion 242 on the thumb press side/area 248, a soft-touch surface disk 249 may be attached to the thumb press area 248 for added comfort during injection.

According to a second process, as shown in FIG. 25, the plunger rod 14 can be manufactured in three separate pieces. The attachment member 244 can be injection molded, the elongated body portion 234 of the plunger rod 14 can be extruded or injection molded, and the cover member 246 or thumb press disk 248 can be manufactured by a stamp molding process. The attachment member 244, elongated body portion 234, and thumb press disk 248 can be formed from different materials for improved performance where needed. For example, a more expensive material may be used to mold the front attachment member 244 for improved performance, and a soft-touch elastomer may be used for the thumb press disk 248. Extruding the body portion 234 of the plunger 14 allows for additional cross-section geometries that would provide uniform side loading deflection and allow for ergonomic improvements that would otherwise be limited by parting lines on the mold. Additionally, using an extrusion process for the body portion allows for the production of body portions of different lengths for use with different length syringe barrels 16 from a single extrusion device.

In the attachment arrangements of FIGS. 17A-17B, 18A-18B, 19A-19B, and 20A-20C, each of these embodiments include a head member 140 having a rim member 142 extending along a front surface 144 thereof, wherein the rim member includes a taper 196 adapted for contacting a corresponding taper 198, within the stopper 12, as shown in FIG. 2B for applying a radial force to the stopper 12 upon the application of a forward force to the plunger rod 14. In the arrangement shown in FIGS. 21A-21F, the deflecting arm 204 includes a taper 213 at a forward end 214 thereof adapted for contacting a corresponding taper 198 within the stopper 12 for applying a radial force to the stopper 12 upon the application of a forward force to the plunger rod 14.

The stopper design of the present invention is intended to prevent reflux by creating positive displacement of fluid into the attached catheter after the stopper 12 has been bottomed in the syringe barrel 16 and force is released from the plunger rod 14. The features of the stopper 12 that act to create this positive displacement are the seal at the nose portion 34 of the stopper 12, the flex or relative movement of the stopper 12 between the nose portion 34 and the forward or first sealing rib 46, and a means by which potential energy in the form of pressurized fluid can be captured and stored prior to the release of the force from the plunger rod 14. The relative movement of the first rib 46 with respect to the nose portion 34 of the stopper 12 is achieved by means of the flexible membrane 44 that connects the outer first rib 46 to the flexible core member 32 and nose portion 34. The energy storing is achieved by means of both the flexible membrane 44 and the air bubble or air pocket chamber 53 that is trapped under the folded forward extending skirt 50 just forward of the first rib 46.

Figure 10:
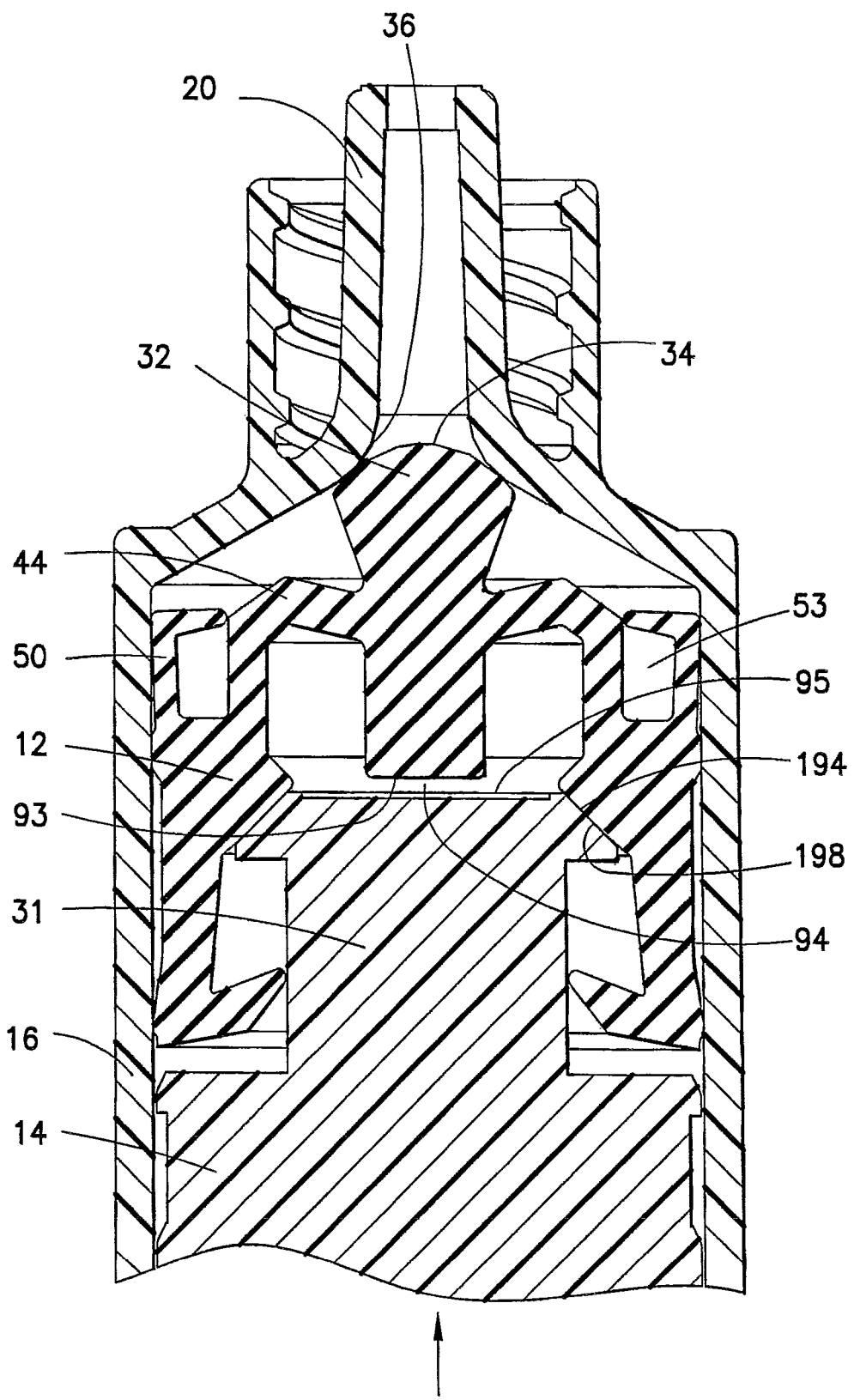
FIG. 10 is a cross-sectional side view of a stopper/plunger arrangement utilizing the stopper of FIG. 2B during a first reflux reduction step of the invention.
Figure 11:
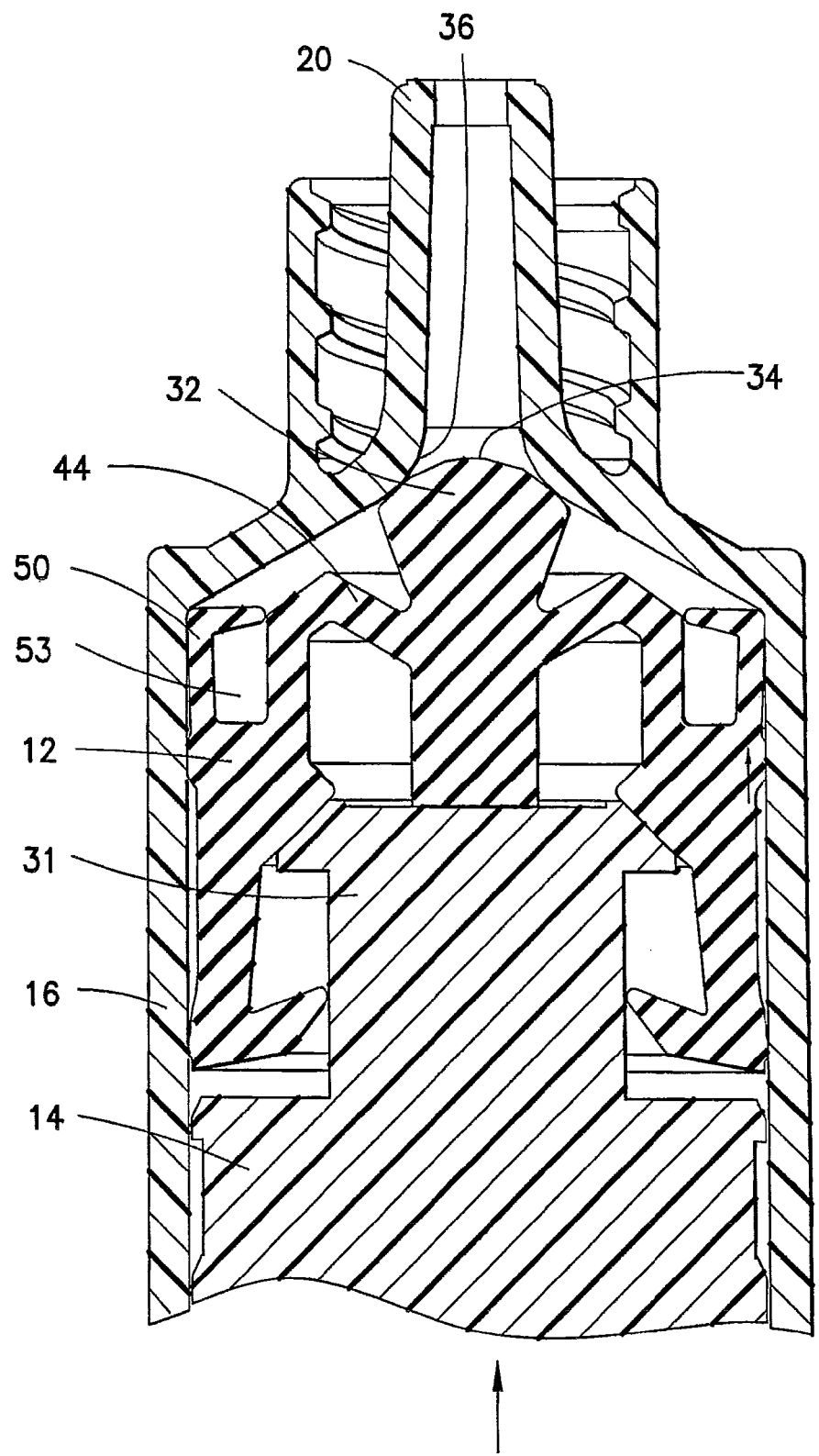
FIG. 11 is a cross-sectional side view of a stopper/plunger arrangement utilizing the stopper of FIG. 2B during a second reflux reduction step of the invention.
Figure 12:
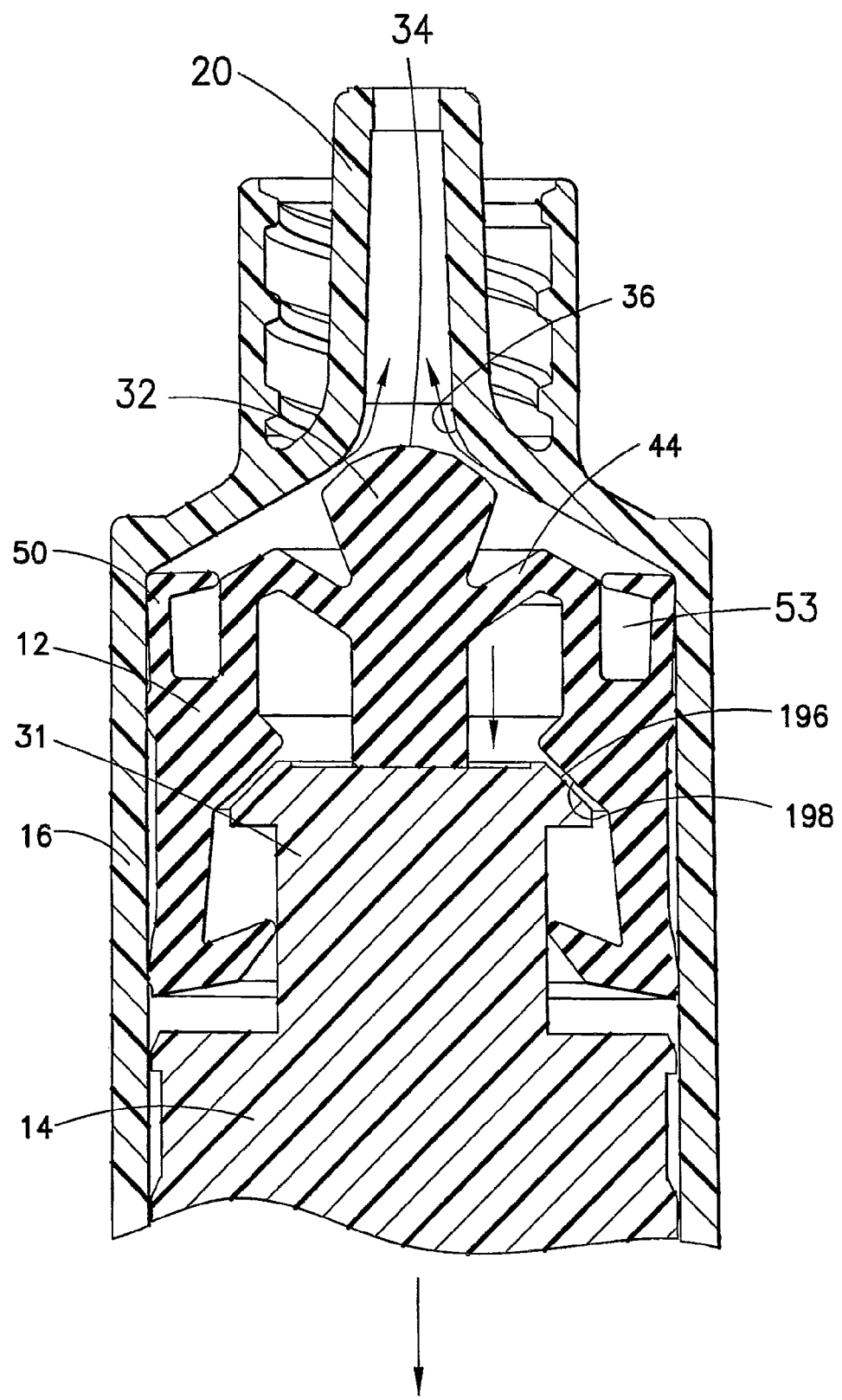
FIG. 12 is a cross-sectional side view of a stopper/plunger arrangement utilizing the stopper of FIG. 2B during a third reflux reduction step of the invention.

As illustrated in FIGS. 10-12, positive displacement or a method of preventing reflux within the syringe barrel includes the following steps. The first step provides a stopper 12 having a main body defining an open rearward end 28 and a closed front end 30. The open rearward end 28 is adapted to receive a front forward end attachment member 31 of a plunger rod 14 therein. A flexible core member 32 is interconnected with the main body 26 via a flexible membrane 44 integrally formed with the main body 26 adjacent the closed front end 30. The flexible core member 32 includes a nose portion 34, preferably having a profile, as discussed above, which is self-centering and adapted to create a positive seal with an interior surface of the luer 20 of the syringe barrel 16. The method further includes the step of inserting the front forward end attachment member 31 of the plunger rod 14 within the open rearward end 28 of the stopper 12. The application of force to the plunger rod 14 advances the stopper 12 into the syringe barrel 16 until the nose portion 34 of the flexible core member 32 contacts the interior surface 36 of the syringe barrel luer 20 forming a seal and trapping fluid from flowing into the luer 20. The application of additional force to the plunger rod 14 to compress the nose portion 34 advances the at least one rib 46 within the syringe barrel 16 and compresses the trapped air to form increased pressure within the air pocket 53. The final step of the method comprises releasing the force on the plunger rod 14 to release the seal between the nose portion 34 and the interior surface 36 of the luer 20, wherein friction force maintains the rib 46 in an advanced position within the syringe barrel 16 such that the increased pressure within the air pocket 53 causes any trapped fluid to be pushed through the luer 20 and any attached catheter.

FIGS. 2A-2B and 3 show a stopper design wherein the stopper 12 includes at least one forward extending skirt 50 extending from a closed front end 30 of the main body 26, and wherein the step of applying a force to advance the stopper 12 into the syringe barrel causes this skirt 50 to deflect inward with respect to the main body 26 of the stopper 12 to substantially contact, or to within a predetermined distance with respect to an outer portion 52 thereof, to form an air pocket 53 for trapping air therein. The step of applying additional force to the plunger rod 14 to compress the nose portion 34 causes the flexible membrane 44 to stretch. The step of releasing the force on the plunger rod 14 thereby releases the force on the flexible membrane 44, causing any trapped fluid to be pushed through an outlet opening or luer 20 and any attached catheter.

FIGS. 4A and 4B show a stopper design which does not rely on a flexible skirt to trap an air bubble to assist in storing energy to force any trapped fluid through the luer 20. Rather, this design only relies on the flexibility of the membrane 44A connecting the flexible core member 32 to the main body 26 of stopper 12 to capture pressure energy and return it once force is released from the plunger rod 14. Additional features that can trap an air bubble include other forms of molded-in pockets or slotted channels in the stopper face.

FIGS. 5A and 5B illustrate yet another design of the stopper 254, according to the invention. This design, discussed in detail above, shows a lip seal for sealing against the barrel. The front seal 256 of the stopper 254 is located on the leading edge of flexible arm 258. The initial sealing pressure is generated by the arm's interference with the barrel wall. When the pressure in the syringe barrel 16 increases, an outward radial force is applied to the inside 259 of the flexible arm 258. This outward push will increase the force with which the seal presses against the barrel wall.

Figure 13:
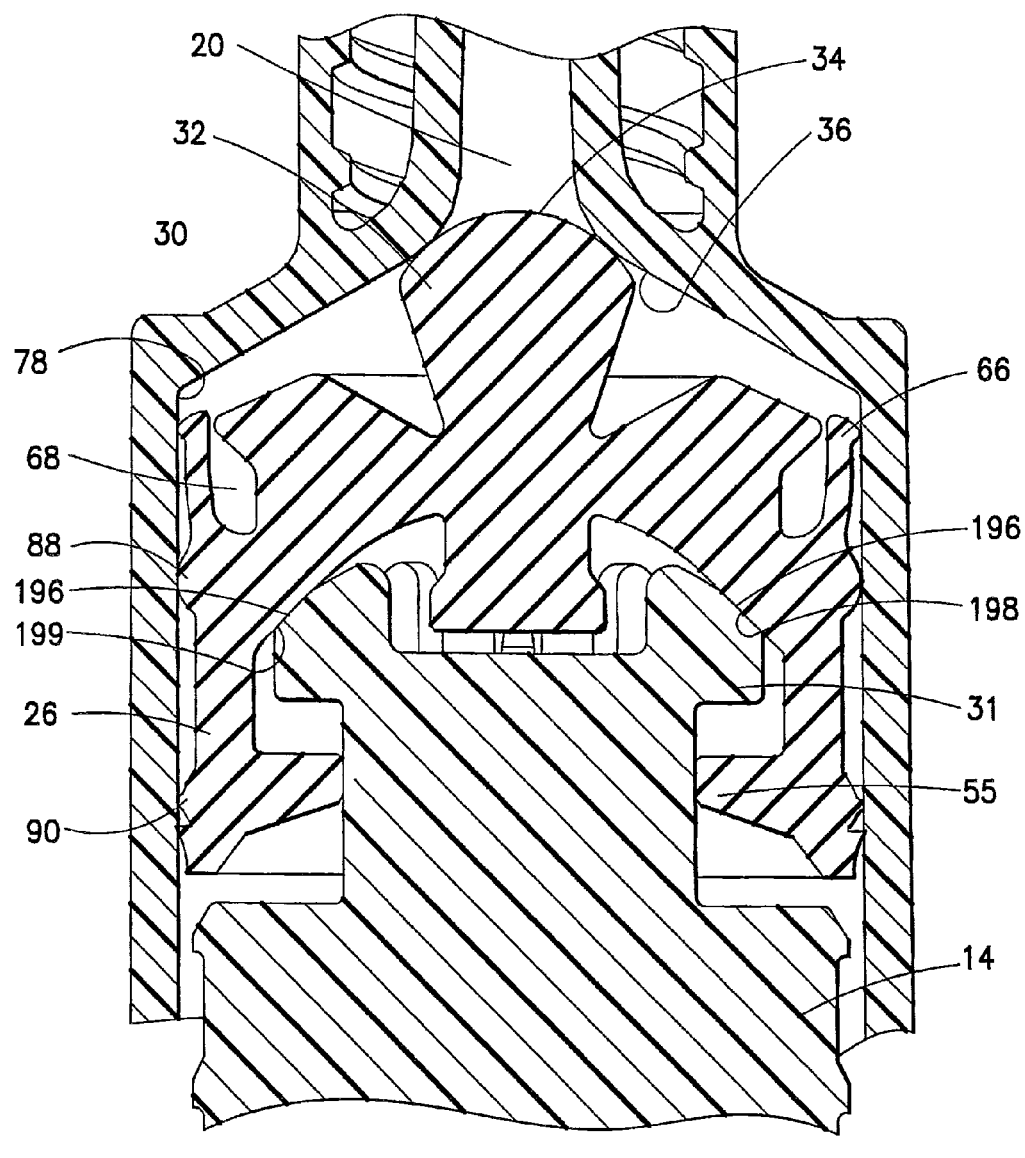
FIG. 13 is a cross-sectional side view of a stopper/plunger arrangement utilizing the stopper embodiment of FIG. 6C during a first reflux reduction step of the invention.
Figure 14:
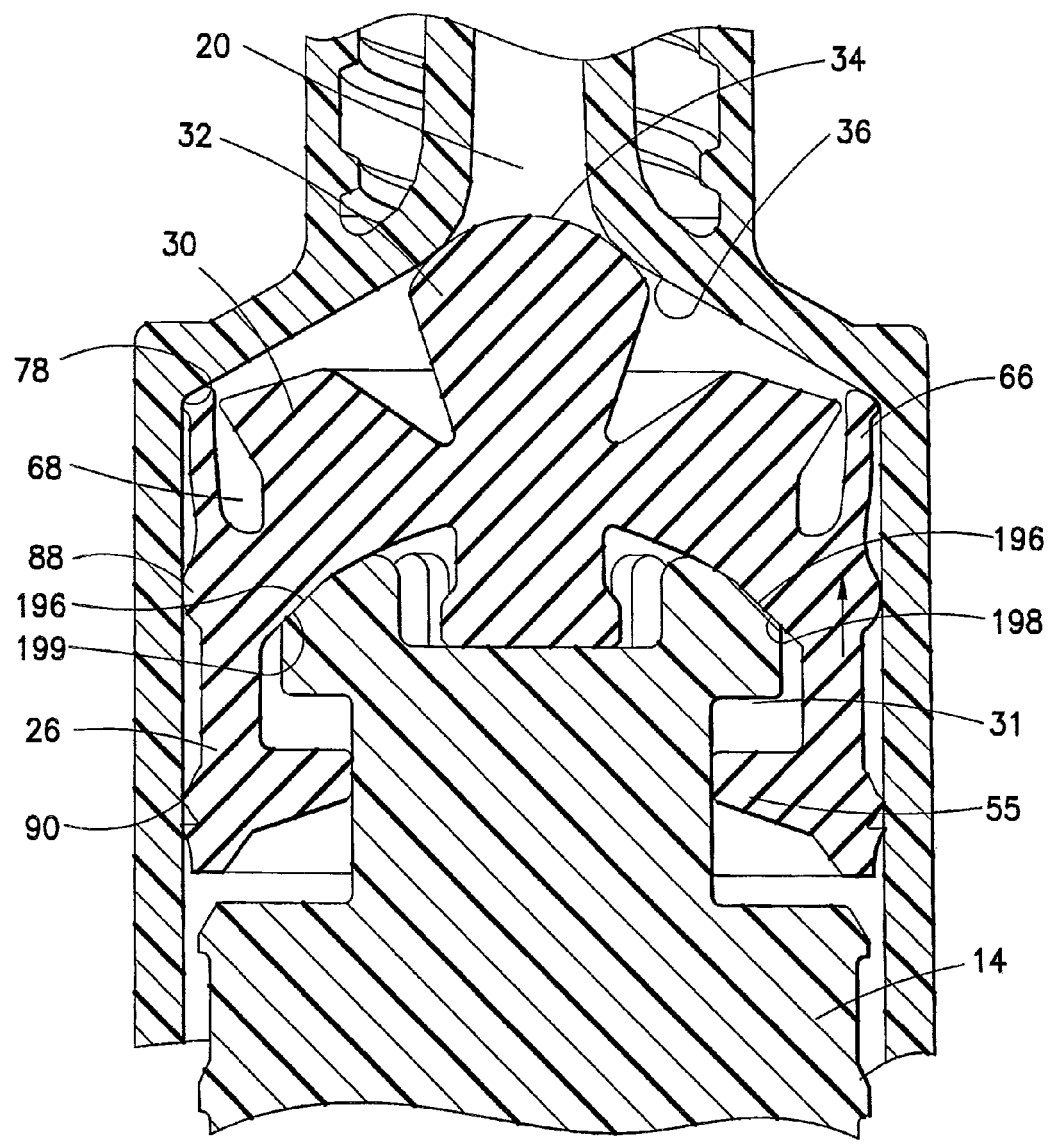
FIG. 14 is a cross-sectional side view of a stopper/plunger arrangement utilizing the stopper embodiment of FIG. 6C during a second reflux reduction step of the invention.
Figure 15:
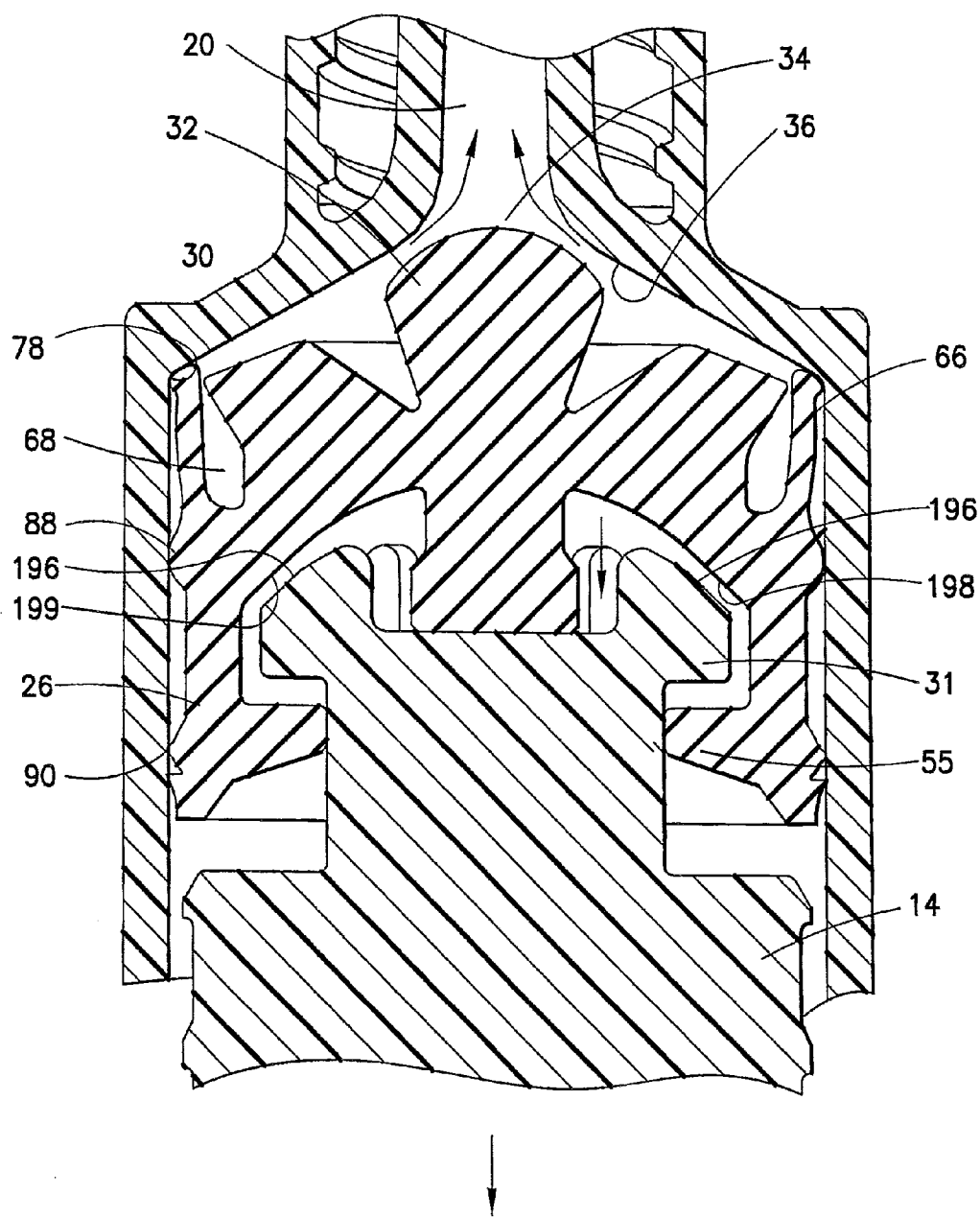
FIG. 15 is a cross-sectional side view of a stopper/plunger arrangement utilizing the stopper embodiment of FIG. 6C during a third reflux reduction step of the invention.

A method of positively displacing fluid and preventing reflux within a syringe barrel utilizing the stopper design of FIG. 6C is also provided by the present invention and is illustrated in FIGS. 13-15. This method comprises the steps of providing a stopper 12 comprising a main body 26 having a closed front end 30. The main body 26 may also include an open rearward end 28 which is adapted to receive a front forward end attachment member 31 of a plunger rod 14 therein. The main body 26 includes a first body portion 60 having a first diameter and a second body portion 62 having a second diameter which is larger than the first diameter of the first body portion 60. A flexible core member 32 is integrally formed with the main body 26 adjacent the closed front end 30. The flexible core member 32 includes a nose portion 34 extending from the front end, a shoulder 64 extending around the first body portion 60 of the main body 26, and at least one perimetrical skirt 66 extending from the second body portion 62 toward the front end 30 of the main body 26. The perimetrical skirt 66 cooperates with the shoulder 64 for trapping at least one air pocket/bubble 68 therein. The perimetrical skirt 66 includes a radially extending bump or first rib 77 along an outer surface lip portion 74. The method further comprises the steps of: providing at least a second rib 88 extending radially outward around a perimeter of an outer diameter portion or second body portion 62 of the main body 26; inserting the front forward end attachment member 31 of a plunger rod 14 within the open rearward end 28 of the stopper 12; applying a force to the plunger rod 14 to advance the stopper 12 into the syringe barrel 16 until the nose portion 34 of the flexible core member 32 contacts the back or interior surface 36 of an outlet opening, such as a luer 20; forming a seal and trapping fluid from flowing into the luer 20; applying additional force to the plunger rod 14 to compress the nose portion 34; advancing the second rib 48 within the syringe barrel 16; and compressing the trapped air to form increased pressure within the air pocket 68. Upon completion of the flushing operation, the method includes the step of releasing the force on the plunger rod 14 to release the seal between the nose portion 34 and the interior surface 36 of the luer 20, wherein friction force maintains the second rib 48 in an advanced position within the syringe barrel 16 such that the increased pressure within the air pocket 68 causes any trapped fluid to be pushed through the luer 20 and any attached catheter. When the seal is lost, the pressure and stored energy in the air pocket/bubble 68 is released. This air pocket/bubble 68 will expand, forcing fluid out from in the front of the stopper 12. This release of pressure pushes outward through the luer 20 causing fluid to be pushed out through any attached catheter.

The nose portion 34 of the flexible core member 32 has a profile adapted to create a positive seal with the interior surface of the luer 20 of the syringe barrel 16. This core member 32 is interconnected with the main body 26 via a flexible and/or elastic membrane 44. The step of applying additional force to the plunger rod 14 to compress the nose portion 34 causes the flexible membrane 44 to stretch, and the step of releasing the force on the plunger rod 14 releases this force on the flexible membrane 44 to cause any trapped fluid to be pushed through the luer 20 and any attached catheter preventing reflux within the syringe barrel 16.

The present invention has numerous advantages over existing plunger rod and stopper designs. In one aspect of the invention, reduced break-loose forces are present when the stopper 12 is first advanced which increases the ease of use of the device and reduces the release that occurs when the stopper 12 is first broken loose. The present designs also improve or reduce the sustaining forces on the stopper 12 due to reduced interference between the stopper 12 and the syringe barrel 16 due to the active seal, which allows the plunger rod 14 and stopper 12 assembly to be used in a wider variety of syringe pump applications. Still another advantage of the inventive assembly is the improved connection between the plunger rod 14 and the stopper 12, especially when the stopper 12 is inserted into the syringe barrel 16 before the plunger rod 14 is attached to the stopper 12. Previous designs, which used a threaded connection, tended to deform the stopper or push it off center, increasing the chance of leakage. Finally, the inventive design achieves a positive displacement of the fluid after the plunger rod 14 is bottomed and the force on the plunger rod 14 is released.

Figure 26:
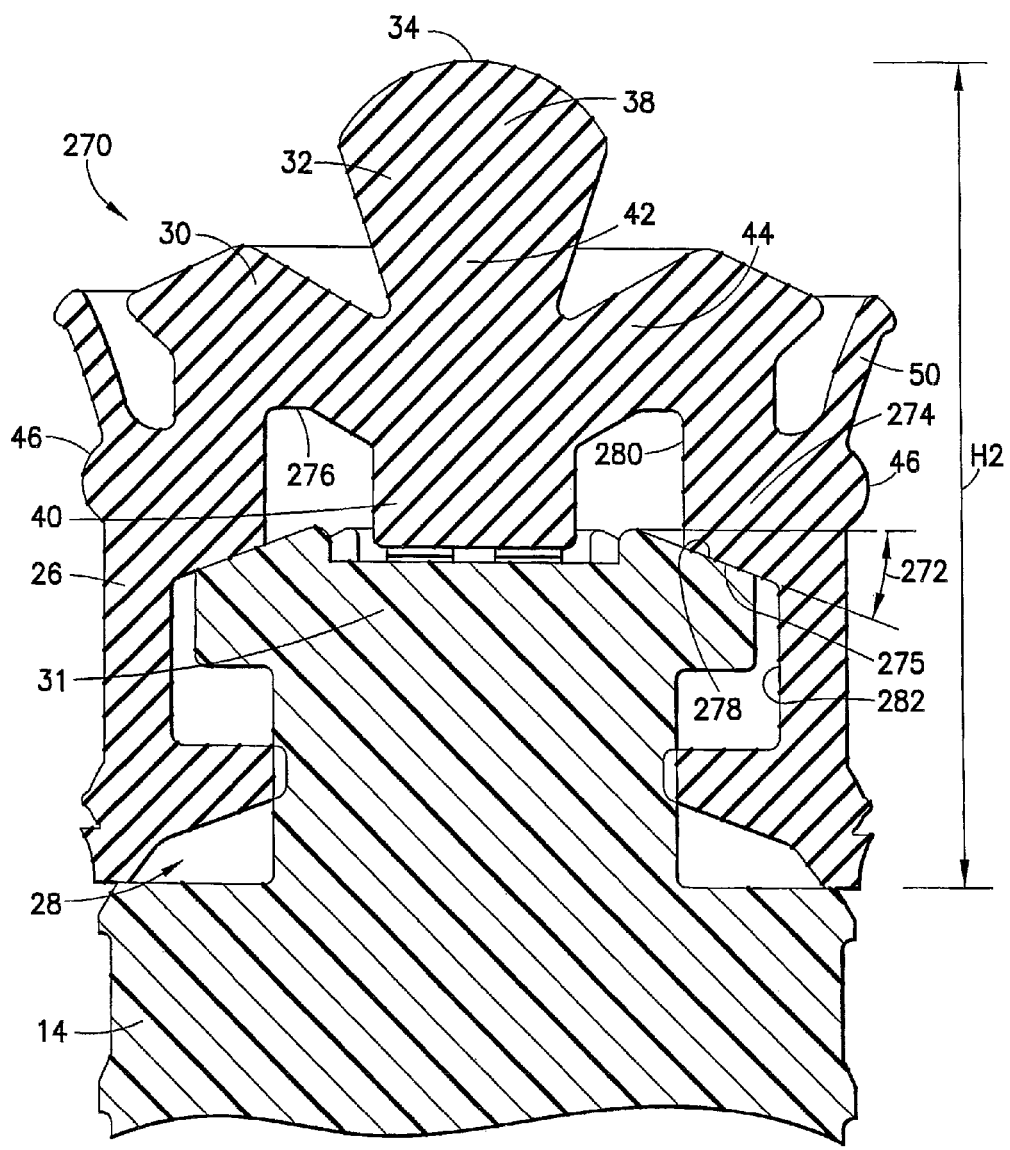
FIG. 26 is a cross-sectional side view of a stopper and plunger rod arrangement according to a fifth embodiment of the invention.

Reference is now made to FIG. 26 which is a cross-sectional view of a stopper, generally indicated as 270, according to a fifth embodiment of the invention wherein the stopper 270 is coupled to a plunger rod 14. This particular embodiment differs from the above described stopper designs in that the active seal angle 272 is shallower and the overall height 112 of the stopper 270 is shorter due to the elimination of an undercut angle 265, as shown in FIGS. 2B, 3, 4B, and 6B, adjacent to the inward shoulder portion 274 of the stopper 12. Referring again to FIG. 26, the core member 32 includes a front portion 38, a back portion 40, and a central portion 42 positioned between the front and back portions 38, 40 wherein the front portion 38 extends beyond the front end 30 of the main body 26 and the central portion 42 is interconnected with the main body 26 via a flexible membrane 44 extending between the core member 32 and the main body 26. The main body 26 includes at least one forward extending skirt 50 extending from a front end of the main body 26. The skirt 50 is adapted for creating a positive pressure chamber therein.

Referring again to FIG. 26, the stopper 270 includes a main body 26 defining an open rearward end 28 and a closed front end 30. The open rearward end 28 is adapted to receive a front forward end attachment portion 31 of a plunger rod 14. The stopper 270 also includes a core member 32 integrally formed with the main body 26 adjacent the closed front end 30. The core member 32 includes a nose portion 34 having a profile adapted to create a positive seal with an outlet opening (not shown) of the syringe barrel (not shown). As previously defined, the term "positive seal" means that the stopper nose portion 34 seats against the outlet opening and seals this opening without deformation of the nose portion 34. The stopper 270 includes at least one rib 46 extending radially outward around a perimeter of the main body 26 for forming an active seal with the syringe barrel.

In this configuration, a shoulder portion 274 having a sloped portion 275 is formed on an inner surface 276 of the main body 26. The inward shoulder portion 274 is adapted for contact with a corresponding taper 278 on the forward end attachment portion 31 of the plunger rod 14. The taper 278 of the plunger rod 14 and the sloped portion 275 of the inward shoulder portion 274 cooperate together to form an active seal angle 272 having a slope such that the stopper 270 applies a radial force to the at least one rib 46 and the syringe barrel 16 upon the application of a forward force to the plunger rod. The inward shoulder portion 274 includes a first cylindrical wall portion 280 extending toward the closed front end 30 of the main body 26 having a substantially flat surface profile that is substantially uniform and non-tapered along the first cylindrical wall portion 280. In this embodiment, the undercut portion 265 shown in FIGS. 2B, 3, 4B, and 6B have been eliminated, and the overall height H2 (shown in the drawings) of the stopper 270 is shorter than the previously described designs. The elimination of the undercut portion 265 also results in an inward shoulder portion 274 including a sloped portion 275 having a smaller or shallower angle than those shown in the stopper designs of FIGS. 2B, 3, 4B, and 6B. This design modification may increase the moldability of the stopper and may reduce the occurrence of "push through" of the taper 278 of the plunger rod 14 past the inward shoulder portion 274 against the front wall or inner surface 276 of the stopper 270. The inward shoulder portion 274 also includes a second cylindrical wall portion 282 extending toward the open rearward end 28 of the main body 26. In one configuration, the sloped portion 275 may extend between the first wall 280 and the second wall 282. The provision of a first wall 280 having a substantially flat surface profile may result in a shorter stopper having an active seal angle 272 which is relatively shallow. As used herein, the term "active seal angle" refers to the angle or slope of the stopper sloped surface 275 that cooperates with the corresponding rod taper 278 wherein forward force on plunger rod 14 causes first rib 46 to form an active seal (as previously defined) with the barrel wall.

Figure 27:
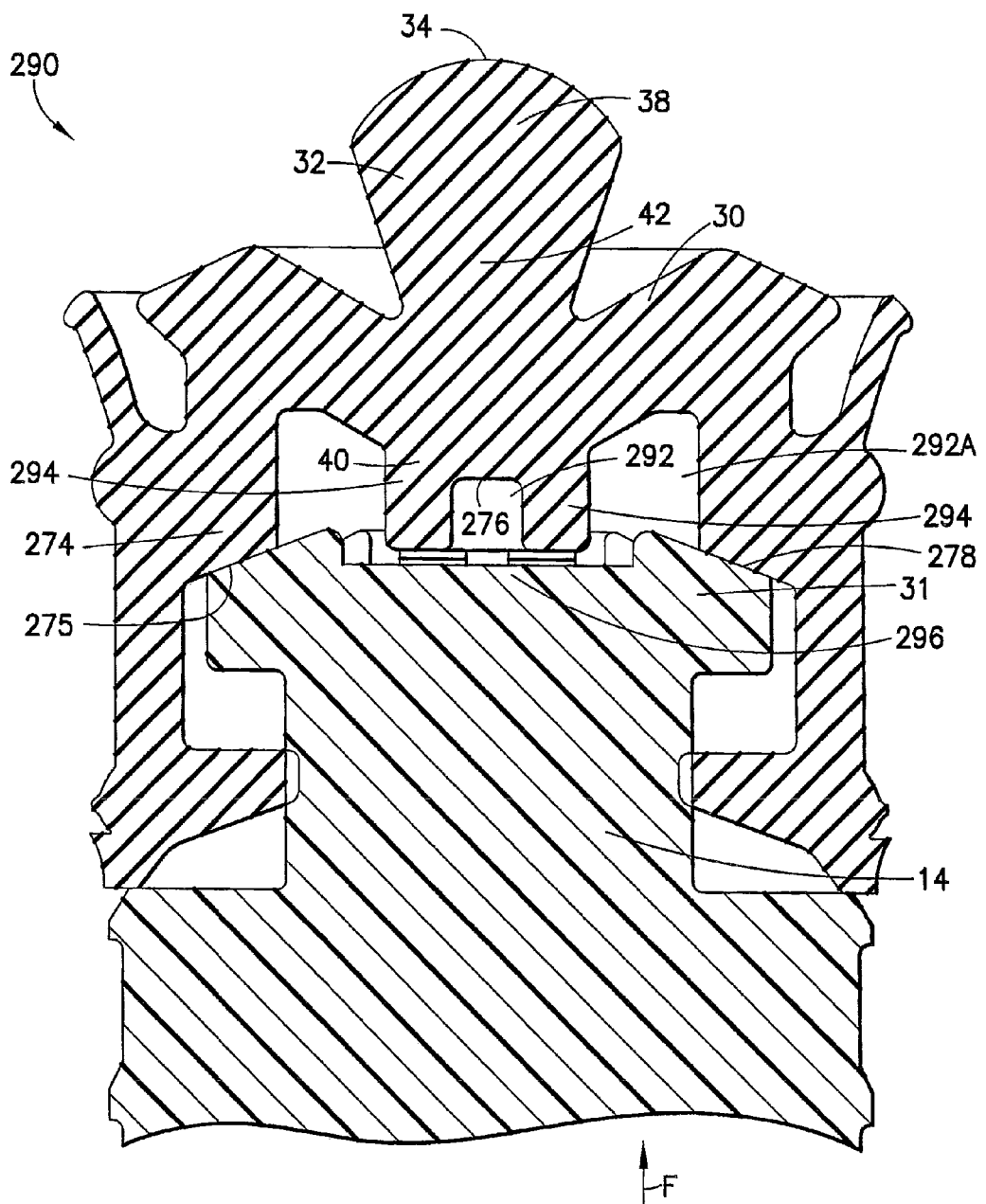
FIG. 27 is a cross-sectional side view of a stopper and plunger rod arrangement according to a sixth embodiment of the invention.
Figure 28:
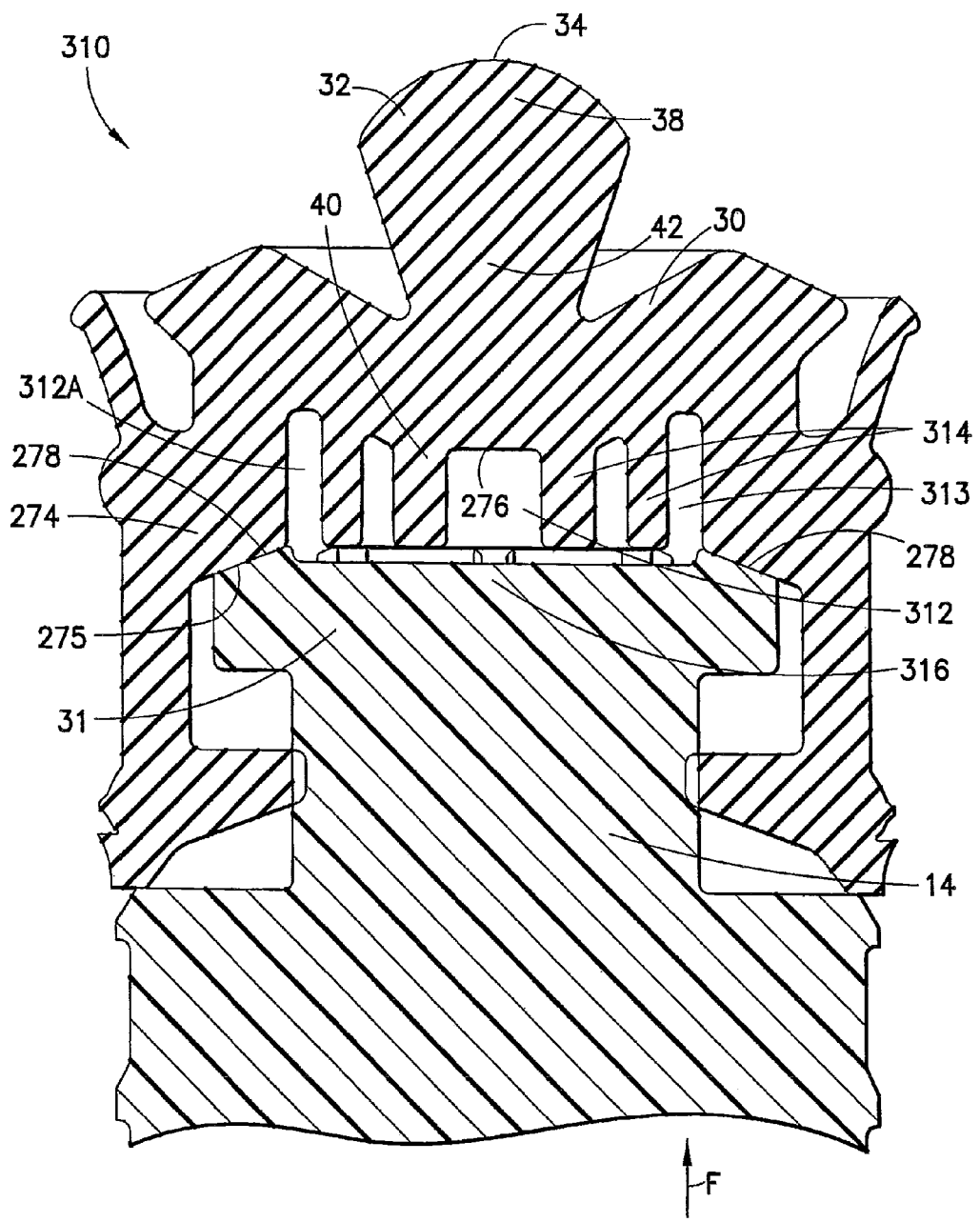
FIG. 28 is a cross-sectional side view of a stopper and plunger rod arrangement according to a seventh embodiment of the invention.

Reference is now made to FIGS. 27 and 28 which show cross-sectional views of a stopper generally indicated as 290 and 310, respectively, according to sixth and seventh embodiments of the invention wherein the stopper 290, 310 is coupled to a plunger rod 14. According to these embodiments, the back portion 40 of the core member 32 and/or an inner surface 276 of the closed front end 30 includes at least one groove 292, 312, 313 formed therein. As shown in FIG. 27, a single groove 292 is provided in the back portion 40 of the core member 32. As shown in FIG. 28, a plurality of grooves 312, 313 are provided, such as concentrically provided, in the back portion 40 of the core member 32 and the inner surface 276 of the closed front end 30. In these embodiments, the groove 292, 312, 313 is defined by at least one protrusion 294, 314 which extends toward the forward end 296, 316 of the front forward end attachment member 31 of the plunger rod 14. The stopper material is adapted for contacting the front forward end 296, 316 of the attachment portion 31 of the plunger rod 14 upon an application of forward force as shown by arrow F to the plunger rod 14. This stopper material 294, 314 prevents the plunger rod 14 and taper 278 of rod 14 from slipping forward into the stopper interior 292A, 312A and reduces the amount of pressure on the back portion 40 and the center 42 of the stopper and the core member 32.

Figure 29:
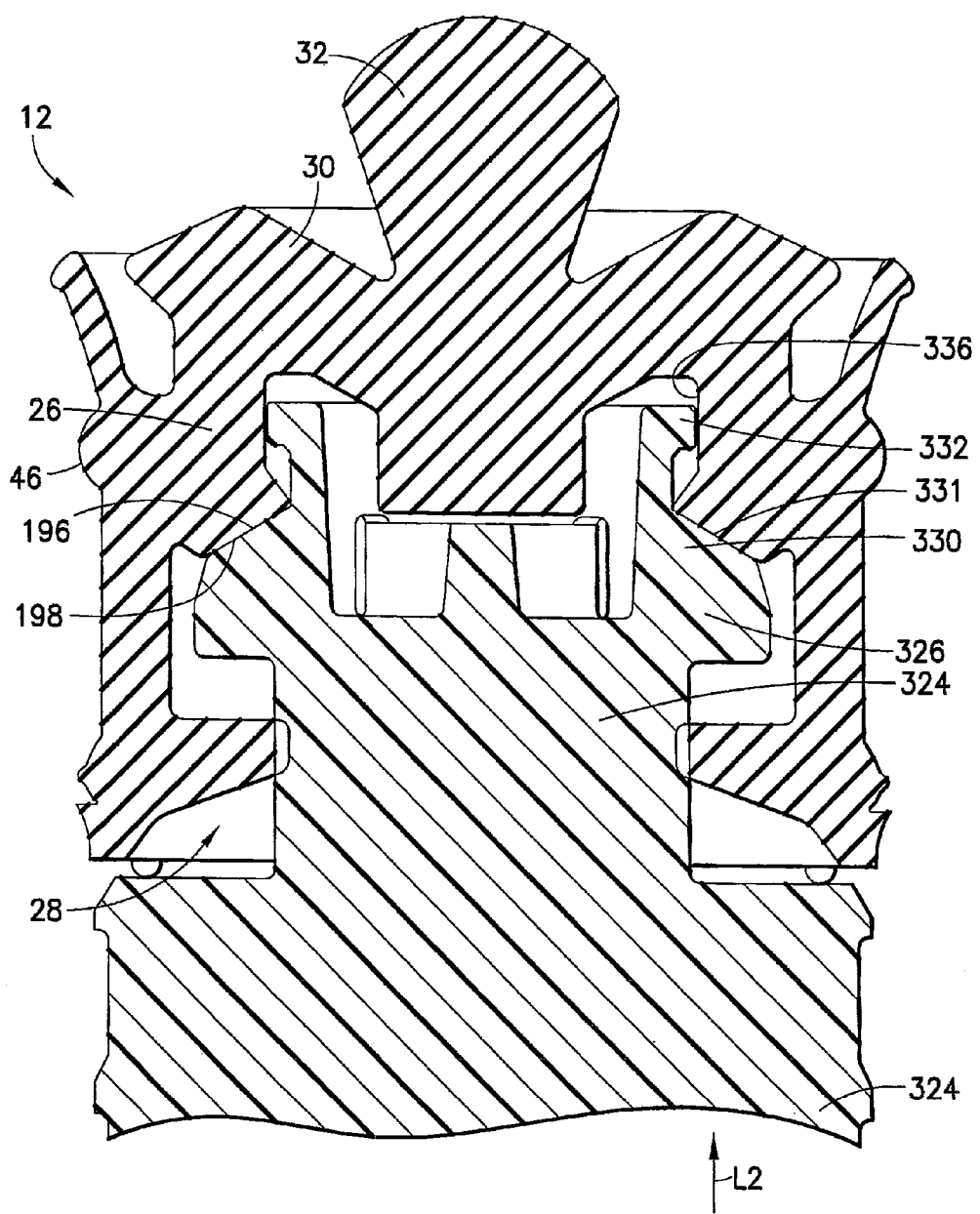
FIG. 29 is a cross-sectional side view of a stopper and plunger rod arrangement according to an alternative design of the invention.

Reference is now made to FIG. 29 which shows a cross-sectional view of a stopper and plunger rod design according to an alternative design of the invention. According to this design, the assembly comprises a plunger rod 324 having a front attachment end 326 and a back end 328 extending along a longitudinal axis. The front attachment end 326 includes a taper 330 and a front flange 332 extending therefrom. The assembly also includes a stopper, generally indicated as 12, having a main body 26 defining an open rearward end 28, a closed front end 30, and a core member 32 integrally formed with the main body 26 adjacent the closed front end 30. The open rearward end 28 is defined by an inside wall surface and is adapted for receiving the front attachment end 326 of the plunger rod 324 and locking the plunger rod 324 within the stopper 12. At least one rib 46 is provided on the stopper 12 that extends radially outward around a perimeter of the main body 26 for forming an active seal with the syringe barrel (not shown). A taper 198 is formed on an inner surface of the main body 26. This taper 198 is adapted for contact with a sloped portion 331 of the taper 330 on the front attachment end 326 of the plunger rod 324. The contacting tapers 198, 330 form an active seal surface for cooperating together such that the stopper 12 applies a radial force to the at least one rib 46 and the syringe barrel upon the application of a forward force to the plunger rod 324. An open space 334 is defined in the stopper 12 by the inner surface 336 of the main body 26, a portion of the core member 32 and the taper 330 on the inner surface 336 of the main body 26. The front flange 332 extending from the front attachment end 326 of the plunger rod 324 extends into this open space 334 to limit the travel of the plunger rod 324 relative to the stopper 12 in a longitudinal direction as shown by arrow L2.

Reference is now made to FIGS. 30A-30E which are directed to a stopper, generally indicated as 340, according to an eighth embodiment of the invention. The stopper 340 is adapted for attachment with a plunger rod 14 shown in FIG. 30C for use within a syringe barrel 16 also shown in FIG. 30C. The stopper 340 comprises a main body 26 defining an open rearward end 28 and a closed front end 30. The open rearward end 28 is adapted to receive a front forward end attachment portion 31 of the plunger rod 14. The stopper 340 further comprises a core member 342 integrally formed with the main body 26 adjacent the closed end 30. The core member 342 includes a back core portion or stopper center post 384 defined by a sidewall portion 385. According to one embodiment, this sidewall portion 385 can be essentially straight along its entire length from a bottom surface 387 of the stopper center post 384 to an intersection 390 where the stopper center post 384 meets the stopper taper 354. This straight sidewall 385 design may allow for a reduction in tooling cost for molding the stopper 340.

The core member 342 includes a nose portion 344 having a conical tip 346 configured for entering an outlet opening 348 of the syringe barrel 16. As stated above, according to one embodiment, the core member 342 can further include a solid or hollow stopper center post 384, protruding from the interior 342A of the core member 342 toward the open rearward end 28. The center post 384 may be adapted for contact with the front forward end attachment portion 31 of the plunger rod 14. According to one embodiment, the main body 26 can include at least a first rib 349 extending radially outward around a perimeter of the main body 26. The main body 26 can also include at least a second rib 350 extending radially outward around a perimeter of the main body 26 and spaced apart from the first rib 349. This first rib 349 and the second rib 350 are adapted for forming an active seal 352 with the syringe barrel 16. The main body 26 can also include a third rib 351 spaced apart from the first rib 349 and second rib 350. The first rib 349, second rib 350, and third rib 351 extend radially outward around a perimeter of the main body 26 and may be axially spaced apart along the main body 26. The main body 26 includes at least one undercut portion 55 extending axially inward of the open rearward end 28. This undercut portion 55 is adapted for locking the front forward end attachment portion 31 of the plunger rod 14 within the stopper 340. The undercut portion 55 may be continuous or segmented. The main body 26 includes an inner surface having a taper 353 adapted for contact with a corresponding taper 354 on the front forward end attachment portion 31 of the plunger rod 14. The contacting tapers 353, 354 cooperate together such that the stopper 340 applies a radial force to the syringe barrel 16 upon the application of a forward force to the plunger rod 14. According to one embodiment, as shown in FIGS. 30A and 30C, the taper 353 of the inner surface of the main body 26 can be a continuous contour having a curvature from a side wall portion 57 of the main body 26 to the core member 342. The main body includes a sidewall 57 having a first diameter for containment within a syringe barrel having a first internal diameter wall portion 360, and the conical tip 346 has a second diameter for contacting the barrel outlet opening 348 having a second internal diameter wall portion 362. The closed front portion 364 of the stopper 340 has a profile configured to cooperate with an internal barrel wall 360 having a tapered wall portion 367 extending between the first and second barrel internal diameter wall portions 360, 362 which allows for a reduction in head space and is shown in FIG. 30C. One embodiment of the stopper 340 includes a closed front portion 364 that has a first slope 369 extending from the nose portion 344 to the first rib 349 which is slightly steeper than a second slope 370 of the tapered wall portion of the syringe barrel 16 extending from the outlet opening 348 of the barrel 16 to a top sidewall portion 372 of the syringe barrel 16.

Figure 30B:
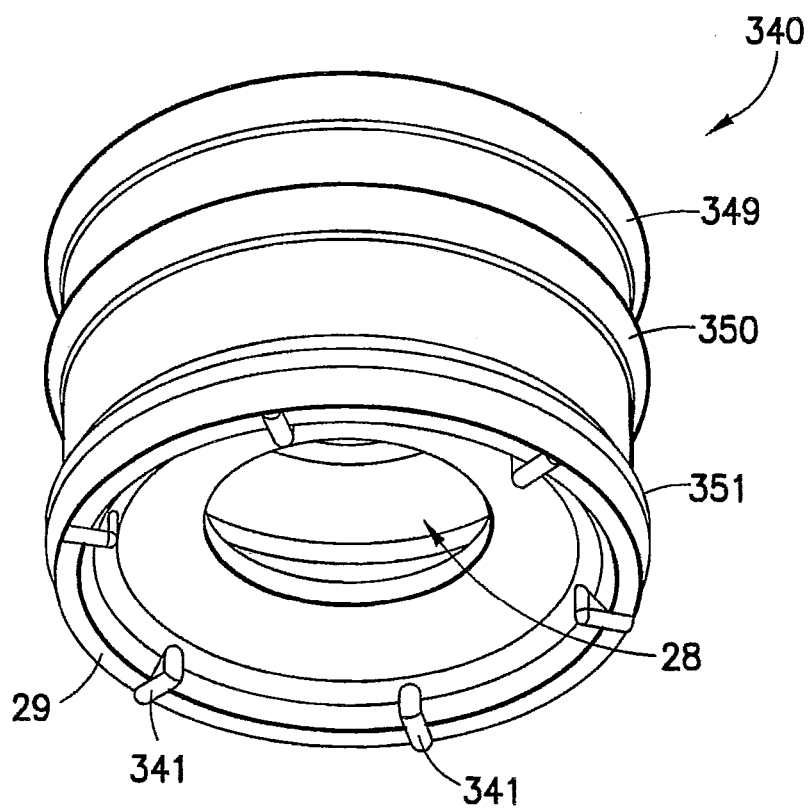
FIG. 30B is a bottom perspective view of the stopper of FIG. 30A.
Figure 30C:
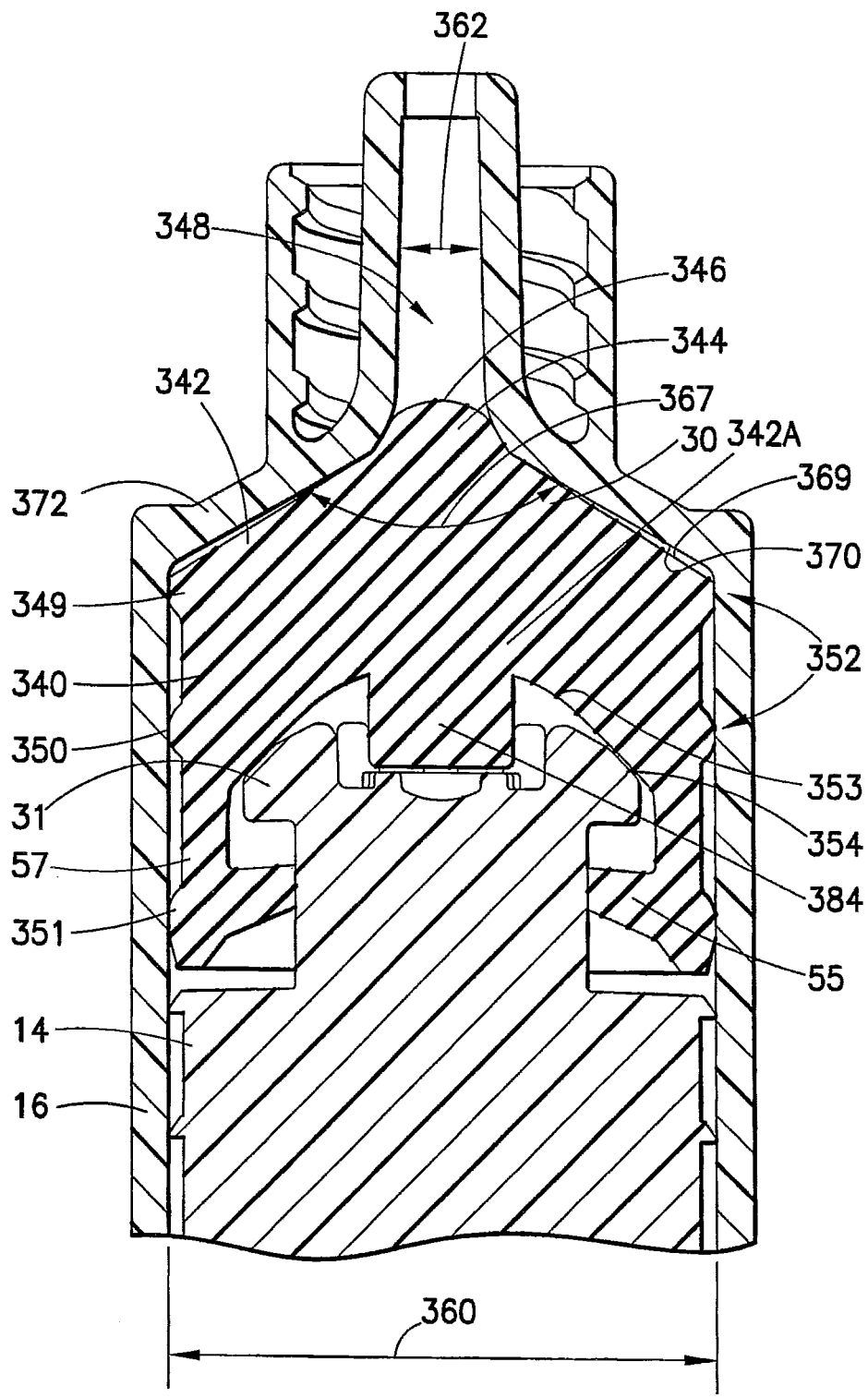
FIG. 30C is a cross-sectional side view of the stopper of FIG. 30A in combination with a plunger rod and positioned within a syringe barrel in accordance with an embodiment of the invention.

In the above described embodiment shown in FIGS. 30A-30E and especially shown in FIG. 30B, the stopper 340 includes an open rearward end 28 defined by an edge portion 29. This edge portion 29 is featured with a plurality of protrusions 341 along the outer perimeter thereof. In a further embodiment, six protrusions 341 may be evenly spaced about the edge portion 29. When the stoppers are bulk-packed during storage and transportation, or in the process of washing and lubrication, there is a chance that the open rearward end 28 and outer edge portion 29 may sit on top of the closed front end 30 of another stopper. The two stoppers may stick to each other and cause errors in the downstream process due to a vacuum in the open chamber of open rearward end 28 or due to lubricant adhesion. The small protrusions 341 of the present invention generate space between the stoppers 340 and thus prevent them from sticking together.

Figure 30D:
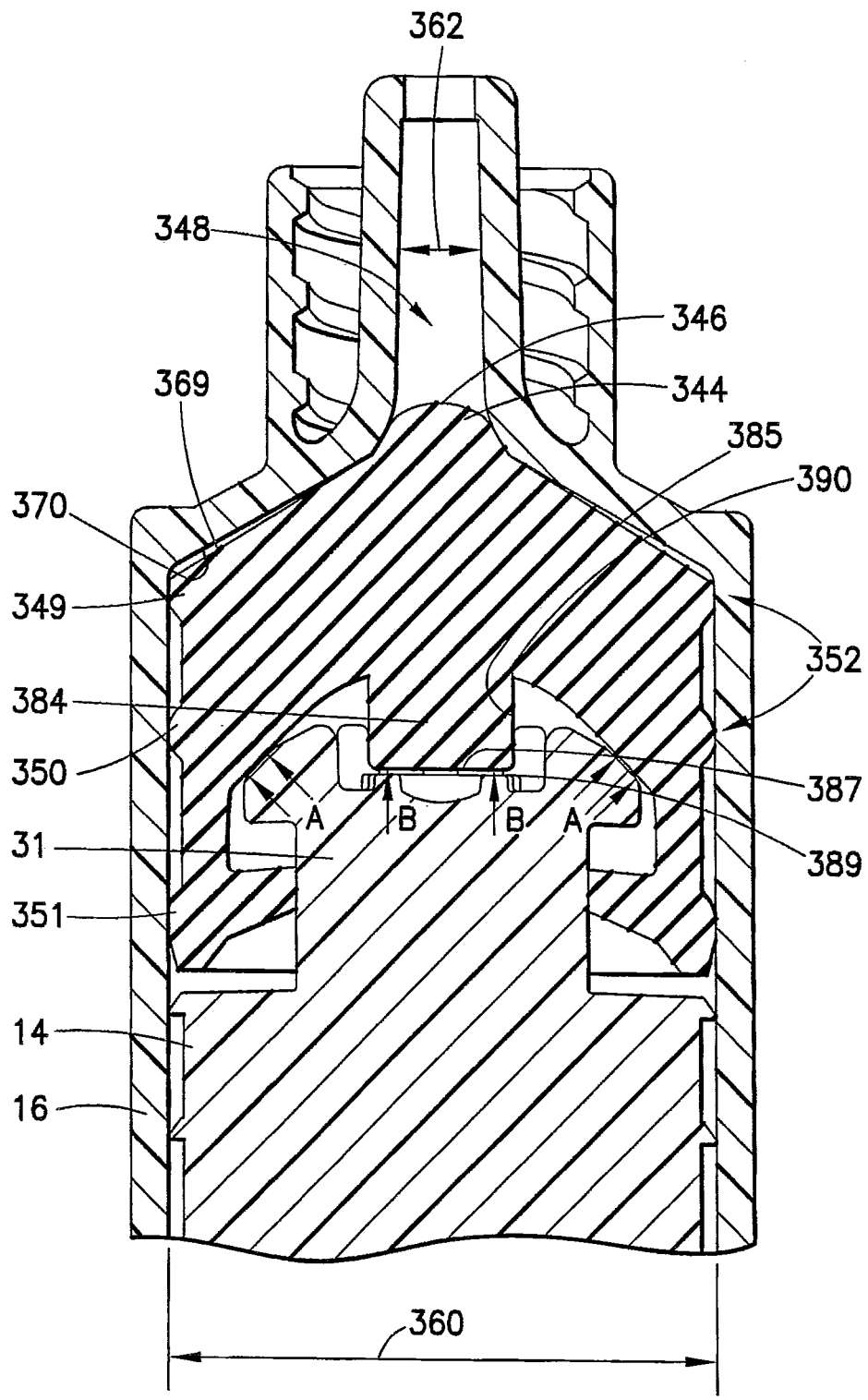
FIG. 30D is a cross-sectional side view of FIG. 30C including directional arrows illustrating the application of force of the plunger rod to the stopper upon the application of a forward force to the plunger rod.
Figure 30E:
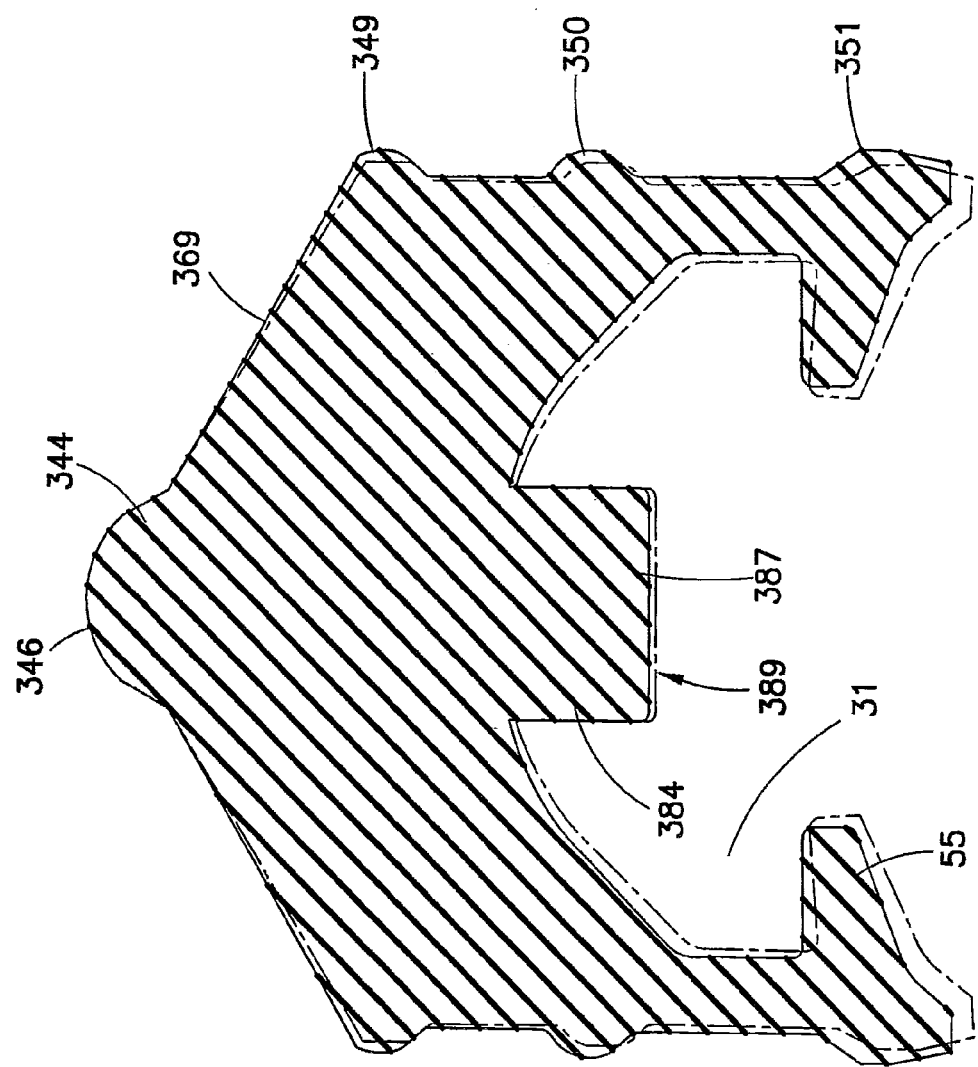
FIG. 30E is a cross-sectional view of the stopper of FIG. 30A illustrating the longitudinal extension and angular change of the stopper face or slope upon the application of radial compression by the syringe barrel wall.

The above described invention, shown in FIGS. 30A-30E, is directed to a syringe having low dead space and essentially zero reflux. As used herein, the phrase "essentially zero" means that the displacement of the barrel contents into the luer opening, once force is removed from the plunger rod 14, is essentially zero which minimizes or results in essentially zero reflux. To prevent reflux, the stopper conical tip 346 is designed to contact the barrel outlet opening 348 at the second internal diameter wall portion 362 and form a seal. The included angle 369 on the stopper face may be less than the barrel included angle 370, such as approximately 1° less than the barrel included angle 370. As shown in FIGS. 30D and 30E, the stopper first slope 369 is squeezed approximately 2.8° steeper due to the nominal interference with the barrel 16 at the first rib 349, second rib 350, and third rib 351. The negative difference between the stopper slope 369 and barrel second slope 370 accounts for the product tolerance on both stopper 340 and barrel 16 such that the conical tip 346 of the stopper always contacts the barrel outlet opening 348 preventing reflux, and the dead space is minimized.

As illustrated in FIGS. 30C-30E, when injection force is applied to the plunger rod 14, the front forward end attachment portion 31 of the plunger rod 14 contacts the center post 384 and through it, pushes the nose portion 344 forward to generate a seal at the area where the conical tip 346 of the stopper contacts the barrel opening 362, overcoming the increasing pressure in the barrel due to plunger rod force. When the contact taper 354 starts to contact the front forward end attachment portion 31 of the plunger rod 14, the center post 384 forms a gap 389 between the bottom surface 387 of the center post 384, as shown in FIGS. 30C and 30D, and the front forward end attachment portion 31. The interaction between the stopper center post 384 and the front forward end attachment portion 31 of the plunger rod adjusts the distribution of the force applied to plunger rod 14 on the stopper conical tip 346 and the active seal 352 at the contact taper 354.

Until the gap 389 is closed, the force is applied to the contact taper 354, as shown by arrows "A" in FIG. 30D, improving the seal at ribs 349 and 350 by at least partially deforming the ribs 349, 350 against the barrel 16. As the force is increased, it is applied to the conical tip 346 through the center post 384, as shown by arrows "B" in FIG. 30D. In one embodiment, the gap was chosen to be 0.008"+/−0.007", such that the active seal 352 is always activated to seal at the first rib 349 and second rib 350 and is larger than the internal pressure in the barrel.

The present invention is able to minimize the occurrence and/or severity of reflux. In one embodiment, the present invention achieves minimal or "essentially zero" reflux while still satisfying the ISO standard for dead space. In the present invention, shown in the design of FIGS. 30A-30E, a dead space of less than 100 such as less than 75 μl or even less than 70 μl, has been realized. In a further embodiment, a dead space of less than 50 μl, such as about 48 has been realized. The ISO standard requirement for dead space for a 3 ml syringe is 70 μl, for a 5 ml syringe is 75 μl, and for a 10 ml syringe is 100 μl. Accordingly, a dead space volume of 48 μl is well within these standards.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

The invention claimed is:

1. A stopper adapted for attachment with a plunger rod for use within a syringe barrel, said stopper comprising:
   (a) a main body defining an open rearward end and a closed front end, said open rearward end adapted to receive a front forward end attachment portion of such plunger rod, said main body including an inner surface;
   (b) a core member integrally formed with said main body adjacent said closed front end, said core member including a nose portion having a conical tip configured for entering an outlet opening of the syringe barrel, said core member including a stopper center post protruding from an interior of the core member toward the open rearward end, said stopper center post including a back core portion adapted for contact with said front forward end attachment portion of the plunger rod;
   (c) at least a first rib extending radially outward around a perimeter of said main body; and
   (d) a taper provided on said inner surface of said main body, said taper adapted for contact with a corresponding taper on the front forward end attachment portion of the plunger rod, said taper and corresponding taper cooperating together to cause the stopper to apply a radial force to the syringe barrel upon the application of a forward force to the plunger rod.

2. The stopper of claim 1, including at least a second rib extending radially outward around a perimeter of said main body, said second rib adapted for forming an active seal with such syringe barrel; and
   wherein the main body includes a sidewall having a first diameter for containment within a syringe barrel having a first internal diameter wall portion, the conical tip has a second diameter for contacting the barrel outlet having a second internal diameter wall portion, and the closed front end has a tapered wall profile configured for cooperating with a tapered wall portion of the internal barrel wall extending between the first and second barrel internal diameter wall portions for preventing reflux which reduces dead space between the stopper and the internal barrel wall.

3. The stopper of claim 2, wherein said main body includes at least a third rib and wherein said first, second, and third ribs extend radially outward around a perimeter of said main body and are axially spaced apart along said main body.

4. The stopper of claim 2, wherein said closed front end has a first slope extending from the nose portion to the first rib and the taper of the syringe barrel extending from the outlet opening of the barrel to a top sidewall portion of the syringe barrel has a second slope and wherein the first slope is steeper than the second slope.

5. The stopper of claim 4, wherein upon the application of a forward force to the plunger rod, the nose portion of the stopper contacts the barrel outlet to prevent reflux and the cooperation of the first and second slopes and radial pressure of the internal barrel wall with respect to at least the first rib causes longitudinal extension of the stopper such that the nose portion extends into the barrel outlet preventing reflux.

6. The stopper of claim 5, wherein an angle of the first slope is approximately 1° less than an angle of the second slope.

7. The stopper of claim 6, wherein the longitudinal expansion of the stopper upon application of a forward force to the plunger rod results in an angle increase of approximately 2.8° of the first slope.

8. The stopper of claim 1, wherein said main body includes at least one undercut portion extending axially inward of said open rearward end, said undercut portion adapted for locking such front forward end attachment portion of such plunger rod within said stopper.

9. The stopper of claim 1, wherein said taper of said inner surface of said main body is a continuous contour from a side wall portion of said main body to said core member.

10. The stopper of claim 1, wherein the open rearward end is defined by a perimetrical edge portion and wherein an outer surface of the edge portion includes at least one protrusion extending therefrom.

11. The stopper of claim 1, wherein the core member includes a back core portion defined by a sidewall portion extending from a bottom core surface to a taper surface of the stopper and wherein the sidewall portion is essentially straight substantially along its entire length.

12. A syringe comprising:
   (a) a cylindrical barrel including a proximal end, a distal end, and a sidewall having a first internal diameter extending between the proximal and distal end, said distal end terminating in an outlet opening having a second internal diameter which is less than said first internal diameter, said cylindrical barrel including a second sloped surface extending between the outlet opening and the barrel sidewall;
   (b) a plunger rod extendable into said barrel through an opening in the proximal end of the barrel, said plunger rod including a front forward attachment portion; and
   (c) a stopper having a main body having an open rearward end, a closed front end, and a sidewall portion extending between said open rearward end and said closed front end, said open rearward end adapted to receive said front forward attachment portion of such plunger rod, a core member integrally formed with said main body adjacent said closed front end, said core member including a nose portion having a conical tip configured for entering the outlet opening of the syringe barrel, said core member including a stopper center post protruding from an interior of the core member toward the open rearward end, said stopper center post including a back core portion adapted for contact with said front forward attachment portion of the plunger rod, said closed front end including a first sloped surface extending from said conical tip to said stopper sidewall portion, wherein said first sloped surface of said stopper is steeper than the second sloped surface of the cylindrical barrel such that an application of a forward force to said plunger rod causes the conical tip of the stopper to enter into the outlet opening to result in essentially zero reflux and wherein the first and second slopes cooperate together to reduce dead space within the barrel, and wherein said main body includes an inner surface having a taper adapted for contact with a corresponding taper on the front forward end attachment portion of the plunger rod, said taper and corresponding taper cooperating together so that said stopper applies a radial force to the syringe barrel upon the application of a forward force to the plunger rod.

13. The syringe of claim 12, wherein said main body includes a first rib extending radially outward around a perimeter of said main body, and at least a second rib extending radially outward around a perimeter of said main body spaced a distance away from said first rib, the at least said second rib adapted for forming an active seal with the syringe barrel.

14. The syringe of claim 12, wherein said taper of said inner surface of said main body is a continuous contour from a side wall portion of said main body to said core member.

15. The syringe of claim 12, wherein said main body includes at least one undercut portion extending axially inward from said open rearward end, said undercut portion adapted for locking the front portion of such plunger rod within said stopper.

16. The syringe of claim 12, wherein upon the application of a forward force to the plunger rod, the nose portion of the stopper contacts the barrel outlet to prevent reflux and the cooperation of the first and second slopes and radial pressure of the internal barrel wall with respect to at least the first rib causes longitudinal extension of the stopper such that the nose portion extends into the barrel outlet preventing reflux.

17. The syringe of claim 16, wherein an angle of the first slope is at least 1° less than the angle of the second slope and wherein the longitudinal expansion of the stopper upon application of a forward force to the plunger rod results in an angle increase of approximately 2.8° of the first slope.

18. A stopper adapted for attachment with a plunger rod for use within a syringe barrel, said stopper comprising:
(a) a main body defining an open rearward end and a closed front end, said open rearward end adapted to receive a front forward end attachment portion of such plunger rod;
(b) a core member integrally formed with said main body adjacent said closed front end, said core member including a nose portion, said core member including a stopper center post protruding from an interior of the core member toward the open rearward end, said stopper center post including a back core portion adapted for contact with said front forward end attachment portion of the plunger rod, said nose portion having a profile adapted to create a positive seal with an outlet opening of such syringe barrel;
(c) at least one rib extending radially outward around a perimeter of said main body for forming an active seal with such syringe barrel; and
(d) an inward shoulder portion on an inner surface of said main body, said inward shoulder portion adapted for contact with a taper on the forward end of the plunger rod, wherein contact of said inward shoulder portion with said taper causes the stopper to apply a radial force to said at least one rib and the syringe barrel upon the application of a forward force to the plunger rod, and wherein said inward shoulder portion includes a first cylindrical wall portion extending from the closed front end of said main body, said first wall portion having a substantially flat surface profile, said inward shoulder portion further including a second cylindrical wall portion extending toward the open rearward end of said main body, and a sloped portion extending between the first wall and the second wall.

19. The stopper of claim 18, wherein said core member includes a front portion, a back portion, and a central portion positioned between said front and back portion, said front portion extending beyond the front end of said main body and said central portion is interconnected with said main body via a flexible membrane extending between said core member and said main body.

20. The stopper of claim 18, wherein said main body includes at least one forward extending skirt extending from a front end of said main body wherein said skirt is adapted for creating a positive pressure chamber therein.

21. The stopper of claim 18, wherein said core member includes a back portion and wherein at least one of said back portion of said core member and an inner surface of said closed front end includes at least one concentric groove formed therein.

22. The stopper of claim 21, wherein at least one of said back portion of said core member and said inner surface of said closed front wall includes stopper material adapted for contacting the front forward end attachment portion of the plunger rod upon an application of forward force to the plunger rod.

23. A plunger rod and stopper assembly adapted for use with a syringe barrel, said assembly comprising:
(a) a plunger rod having a front attachment end and a back end and extending along a longitudinal axis, said front attachment end including a taper and a front flange extending therefrom;
(b) a stopper having a main body defining an open rearward end, a closed front end, and a core member integrally formed with said main body adjacent said closed front end, said core member including a stopper center post protruding from an interior of the core member toward the open rearward end, said stopper center post including a back core portion adapted for contact with said front attachment end of the plunger rod, said open rearward end defined by an inside wall surface, said open end adapted for receiving said front attachment end of said plunger rod and locking said plunger rod within said stopper;
(c) at least one rib extending radially outward around a perimeter of said main body for forming an active seal with the syringe barrel;
(d) a taper formed on an inner surface of said main body, said taper having a sloped portion adapted for contact with said taper on the front attachment end of such plunger rod, said contacting tapers forming an active seal surface for cooperating together causing said stopper to apply a radial force to said at least one rib and the syringe barrel upon the application of a forward force to the plunger rod; and
(e) an open space defined by the inner surface of the main body, a portion of said core member, and said taper on the inner surface of said main body, wherein said front flange extending from said front attachment end of said plunger rod extends into said open space.

\* \* \* \* \*